(12) United States Patent
Ebright et al.

(10) Patent No.: US 11,447,502 B2
(45) Date of Patent: Sep. 20, 2022

(54) ANTIBACTERIAL AGENTS: DUAL-TARGETED RNA POLYMERASE INHIBITORS

(71) Applicant: RUTGERS, THE STATE UNIVERSITY OF NEW JERSEY, New Brunswick, NJ (US)

(72) Inventors: Richard H. Ebright, New Brunswick, NJ (US); Yon W. Ebright, New Brunswick, NJ (US); Chih-Tsung Lin, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 17/058,589

(22) PCT Filed: May 23, 2019

(86) PCT No.: PCT/US2019/033788
§ 371 (c)(1),
(2) Date: Nov. 24, 2020

(87) PCT Pub. No.: WO2019/226915
PCT Pub. Date: Nov. 28, 2019

(65) Prior Publication Data
US 2021/0198279 A1 Jul. 1, 2021

Related U.S. Application Data

(60) Provisional application No. 62/677,596, filed on May 29, 2018, provisional application No. 62/676,805, filed on May 25, 2018.

(51) Int. Cl.
*C07D 498/08* (2006.01)
*A61P 31/06* (2006.01)

(52) U.S. Cl.
CPC ............ *C07D 498/08* (2013.01); *A61P 31/06* (2018.01)

(58) Field of Classification Search
CPC ............................... C07D 498/08; A61P 31/06
See application file for complete search history.

(56) References Cited

U.S. PATENT DOCUMENTS

| | | | |
|---|---|---|---|
| 8,372,839 B2 * | 2/2013 | Ebright ................ | C07D 498/08 514/258.1 |
| 9,243,039 B2 | 1/2016 | Ebright et al. | |
| 9,415,112 B2 | 8/2016 | Ebright et al. | |
| 9,919,998 B2 | 3/2018 | Ebright et al. | |
| 10,010,619 B2 | 7/2018 | Ebright et al. | |
| 2004/0063718 A1 | 4/2004 | Michaelis et al. | |
| 2005/0187409 A1 | 8/2005 | Powers et al. | |
| 2009/0137467 A1 | 5/2009 | Ebright et al. | |
| 2016/0347708 A1 | 12/2016 | Ebright et al. | |
| 2017/0056512 A1 | 3/2017 | Ebright et al. | |

FOREIGN PATENT DOCUMENTS

| | | |
|---|---|---|
| WO | 2007089310 A1 | 8/2007 |
| WO | 2012177770 A1 | 12/2012 |
| WO | 2015120320 A1 | 8/2015 |

OTHER PUBLICATIONS

Agarwal, A., et al., "Synthesis of de novo designed small-molecule inhibitors of bacterial RNA polymerase", Tetrahedron 64, 10049-10054 (2008).
Artsimovitch, I., et al., "Allosteric Modulation of the RNA Polymerase Catalytic Reaction Is an Essential Component of Transcription Control by Rifamycins", Cell 122, 351-363 (2005).
Belogurov, et al., "Transcription inactivation through local refolding of the RNA polymerase structure", Nature 457(7227), 332-335 (2009).
Binder, et al., "Emerging infectious diseases: public health issues for the 21st century", Science 284, 1311-1313 (1999).
Borukhov, S., et al., "RNA polymerase holoenzyme: structure, function and biological implications", Curr Opin Microbiol 6, 93-100 (2003).
Bushnell, et al., "Structural basis of transcription: α-Amanitin-RNA polymerase II cocrystal at 2.8 Å resolution", Proc. Natl. Acad. Sci. U.S.A. 99, 1218-1222 (2002).
Campbell, E., et al., "Structural Mechanism for Rifampicin Inhibition of Bacterial RNA Polymerase", Cell 104, 901-912 (2001).
Campbell, et al., "Structural, functional, and genetic analysis of sorangicin inhibition of bacterial RNA polymerase", Embo J. 24, 674-682 (2005).
Chopra, I., "Bacterial RNA polymerase: a promising target for the discovery of new antimicrobial agents", Curr. Opin. Investig. Drugs 8, 600-607 (2007).
Cramer P., et al., "Architecture of RNA Polymerase II and Implications for the Transcription Mechanism", Science 288, 640-649 (2000).
Cramer, P., et al., "Multisubunit RNA polymerases", Current Opinion in Structural Biology 12(1), 89-97 (2002).
Cramer, P., "RNA polymerase II structure: from core to functional complexes", Current Opinion in Genetics & Development 14(2), 218-226 (2004).
Cramer, P., et al., "Structural Basis of Transcription: RNA Polymerase II at 2.8 Ångstrom Resolution", Science 292, 1863-1876 (2001).
Cramer, P., et al., "Structure of Eukaryotic RNA Polymerases", Annual Review of Biophysics 37, 337-352 (2008).
Darst, S., "Bacterial RNA polymerase", Curr Opin Structl Biol 11, 155-162 (2001).

(Continued)

*Primary Examiner* — Timothy R Rozof
(74) *Attorney, Agent, or Firm* — Viksnins Harris Padys Malen LLP

(57) ABSTRACT

The invention provides bipartite, dual-targeted inhibitors of bacterial RNA polymerase having the general structural formula (I): X-α-Y (I) wherein X is an moiety that binds to the Rif target of a bacterial RNA polymerase; Y is a moiety that binds to the bridge-helix N-terminus target of a bacterial RNA polymerase; and is a covalent bond or a linker. The invention also provides compositions comprising such compounds, methods of making such compounds, and methods of using said compounds. The invention has applications in control of bacterial gene expression, control of bacterial growth, antibacterial chemistry, and antibacterial therapy.

18 Claims, 5 Drawing Sheets

(56) References Cited

OTHER PUBLICATIONS

Darst, S. , "New inhibitors targeting bacterial RNA polymerase", Trends Biochem. Sci. 29, 159-162 (2004).
Dye, C. , et al., "Worldwide Incidence of Multidrug-Resistant Tuberculosis", J. Infect. Dis. 185, 1197-1202 (2002).
Ebright, R , "RNA polymerase: structural similarities between bacterial RNA polymerase and eukaryotic RNA polymerase II", J Mol Biol 304, 687-698 (2000).
Feklistov, A. , et al., "Rifamycins do not function by allosteric modulation of binding of Mg2+ to the RNA polymerase active center", Proc. Natl. Acad. Sci. USA 105(39), 14820-14825 (2008).
Floss, H , et al., "Rifamycin—Mode of Action, Resistance, and Biosynthesis", Chem Rev 15, 621-632 (2005).
Gnatt, A. , et al., "Structural Basis of Transcription: An RNA Polymerase II Elongation Complex at 3.3 Å Resolution", Science 292, 1876-1882 (2001).
Hahn, S. , "Structure and Mechanism of the RNA Polymerase II Transcription Machinery", Nat. Struct. Mol. Biol. 11(5), 394-403 (2004).
Hirata, A. , et al., "Archaeal RNA polymerase", Curr. Opin. Structl. Biol. 19, 724-731 (2009).
Ho , et al., "Structures of RNA polymerase-antibiotic complexes", Curr. Opin. Struct. Biol. 19, 715-723 (2009).
Jun, S. , et al., "Archaeal RNA polymerase and transcription regulation", Crit. Rev. Bhiochem. Mol. Biol. 46, 27-40 (2011).
Kettenberger, H. , et al., "Complete RNA Polymerase II Elongation Complex Structure and Its Interactions with NTP and TFIIS", Mol. Cell 16, 955-965 (2004).
Kettenberger , et al., "Structure of an RNA polymerase II—RNA inhibitor complex elucidates transcription regulation by noncoding RNAs", Natl. Structl. Mol. Biol. 13, 44-48 (2005).
Kornberg, R. , "The molecular basis of eukaryotic transcription", Proc. Natl. Acad. Sci. USA 104, 12955-12961 (2007).
Lane , et al., "Molecular evolution of multisubunit RNA polymerases: sequence analysis", J. Mol. Biol. 395, 671-685 (2010).
Lane W., et al., "Molecular Evolution of Multi-subunit RNA Polymerases: Structural Analysis", J. Mol. Biol. 395(4), 686-704 (2010).
Lebedeva, S , et al., "Various properties of RifR mutants of the plague agent", Antibiot. Khimioter. 36, 19-22 (1991).
Levy, S , "The Challenge of Antibiotic Resistance", Scientific American 46-53 (Mar. 1998).
Lin, W , et al., "Structural Basis of *Mycobacterium tuberculosis* Transcription and Transcription Inhibition", Molecular Cell 66(2), 169-179 (2017).
Marianelli, C. , et al., "Genetic Bases of the Rifampin Resistance Phenotype in*Brucella*spp", J. Clin. Microbiol. 42, 5439-5443 (2004).
Mariani , et al., "Antibiotics GE23077, novel inhibitors of bacterial RNA polymerase. Part 3: Chemical derivatization", Bioorganic & Medicinal Chemistry Letters, vol. 15 (16), 3748-3752 (2005).
Mariani, R , et al., "Bacterial RNA Polymerase Inhibitors: An Organized Overview of their Structure, Derivatives, Biological Activity and Current Clinical Development Status", Current Medicinal Chemistry 16, 430-454 (2009).
Mitchison, D. A. , "Role of individual drugs in the chemotherapy of tuberculosis", Int. J. Tuberc. Lung Dis. 4, 796-806 (2000).
Mukhopadhyay , et al., "The RNA polymerase "switch region" is a target for inhibitors", Cell 135, 295-307 (2008).
Murakami, K , et al., "Bacterial RNA polymerases: the wholo story", Curr Opin Structl Biol 13, 31-39 (2003).
Obst, G. , et al., "Rifampin activity against *Staphylococcus epidermidis* biofilms", ASAIO Trans. 34, 782-784 (1988).
Obst, G. , et al., "The Activity of Rifampin and Analogs against *Staphylococcus epidermidis* Biofilms in a CAPD Environment Model", Am. J. Nephrol. 9, 414-420 (1989). [Abstract].

Patent Cooperation Treaty , International Searching Authority, Search Report and Written Opinion for PCT/US2019/033788, 9 pages, dated Aug. 16, 2019.
Pomerantsev, A , et al., "Characterization of a Rif-R population of Bacillus anthracis", Antibiot. Khimioter. 38, 34-38 (1993). [Abstract].
Pubchem , CID 2955118, 11 pages, Create Date Jul. 29, 2005.
Pubchem , CID 7325930, 10 pages, Create date Jul. 29, 2006.
Pubchem , CID 970466, 10 pages, Create Date Jul. 9, 2005.
Raviglione , et al., "The burden of drug-resistant tuberculosis and mechanisms for its control", Ann NY Acad Sci 953, 88-97 (2001).
Sarubbi , et al., "Mode of action of the microbial metabolite GE23077, a novel potent and selective inhibitor of bacterial RNA polymerase", Eur J Biochem 271, 3146-3154 (2004).
Schluger, N , "The impact of drug resistance on the global tuberculosis epidemic", Int J Tuberculosis Lung Disease 4, S71-S75 (2000).
Srivastava , et al., "New Target for inhibition of bacterial RNA polymerase: switch region", Curr. Opini. Microbiol. 14, 532-543 (2011).
Temiaov , et al., "Structural Basis of Transcription Inhibition by Antibiotic Streptolydigin", Mol. Cell 19, 655-666 (2005).
Tuske , et al., "Inhibition of Bacterial Rna Polymerase by Streptolydigin: Stabilizaiton of a Straight-Bridge-Helix Active-Center Conformation", Cell, vol. 122 (4), 541-552 (2005).
Vannini A., et al., "Conservation between the RNA Polymerase I, II, and III Transcription Initiation Machineries", Molecular Cell Review 45, 439-446 (2012).
Vassylyev , et al., "Structural basis for substrate loading in bacterial RNA polymerase", Nature 448, 163-168 (2007).
Vassylyev D., et al., "Structural basis for transcription elongation by bacterial RNA polymerase", Nature 448, 157-162 (2007).
Villain-Guillot , et al., "In Vitro Activities of Different Inhibitors of Bacterial Transcription against *Staphylococcus epidermidis* Biofilm", Antimicrob. Agents Chemother. 51, 3117-3121 (2007).
Villain-Guillot , et al., "Progress in targeting bacterial transcription", Drug Discov. Today 12 (5/6), 200-208 (2007).
Volger, A. , et al., "Molecular Analysis of Rifampin Resistance in Bacillus anthracis and Bacillus cereus", Antimicrob. Agents Chemother. 46, 511-513 (2002).
Walsh, C , "Molecular mechanisms that confer antibacterial drug resistance", Nature 406, 775-781 (2000).
Werner, F. , et al., "Evolution of multisubunit RNA polymerases in the three domains of life", Nature Rev. Microbiol. 9, 85-98 (2011).
Werner, F. , et al., "Structure and function of archaeal RNA polymerases", Molecular Microbiology 65(6), 1395-1404 (2007).
Westover, K. , et al., "Structural Basis of Transcription: Nucleotide Selection by Rotation in the RNA Polymerase II Active Center", Cell 119, 481-489 (2004).
Westover K., et al., "Structural Basis of Transcription: Separation of RNA from DNA by RNA Polymerase II", Science 303, 1014-1016 (2004).
World Health Organization , "Anti-tuberculosis drug resistance in the world : third global report / the WHO/IUATLD Global Project on Anti-Tuberculosis Drug Resistance Surveillance, 1999-2002", WHO/IUATLD Global Project on Anti-Tuberculosis Drug Resistance Surveillance, World Health Organization & World Health Organization. (2004).
Zhang G., et al., "Crystal Structure of Thermus aquaticus Core RNA Polymerase at 3.3 A° Resolution", Cell 98, 811-824 (1999).
Zumia, A. , et al., "Multidrug-resistant tuberculosis—can the tide be turned?", Lancet Infect. Dis. 1, 199-202 (2001).
Feng, Y , et al., "Structural Basis of Transcription Inhibition by CBR Hydroxamidines and CBR Pyrazoles", Structure 23, 1470-1481 (2015).

* cited by examiner

FIG. 1 fork loop 2     region D     region D/E spacer

βa8

| | | 475 (550) | 477 (552) | 480 (555) | | | 562 (637) | 566 (640) | 568 (642) | | |
|---|---|---|---|---|---|---|---|---|---|---|---|
| RPOB_MYCTU | (471) | E V R D M H P S H Y G R M | | | (559) | V L V R R K A G E M E Y V | | | | } | Mycrobacterial Gram-positive bacterial RNAP |
| RPOB_MYCA1 | (471) | E V R D M H P S H Y G R M | | | (559) | V L V R R K A G E M E Y V | | | | | |
| RPOB_MYCA9 | (467) | E V R D M H P S H Y G R M | | | (555) | I L V R R K G G E M E F V | | | | | |
| RPOB_MYCSM | (462) | E V R D M H P S H Y G R M | | | (550) | V M V R K K G G E M E F V | | | | | |
| RPOB_ECOLI | (546) | E V R D M H P S H Y G R V | | | (634) | V T C R S K - G E S S L F | | | | } | Gram-negative bacterial RNAP |
| RPOB_SALTY | (546) | E V R D M H P T H Y G R V | | | (634) | V T C R S K - G E S S L F | | | | | |
| RPOB_KLEP7 | (546) | E V R D M H P T H Y G R V | | | (634) | V T C R S K - G E S S L F | | | | | |
| RPOB_ENTCC | (546) | E V R D M H P T H Y G R V | | | (634) | V T C R S K - G E S S L F | | | | | |
| RPOB_HAEIN | (546) | E V R D M H N T H Y G R L | | | (634) | V T A R G E R G E S G L Y | | | | | |
| RPOB_NEIG1 | (573) | E V R D M H P T H Y G R V | | | (661) | V T C R E K - G E T I M A | | | | | |
| RPOB_STPMP | (574) | E V R D M H P T H Y G R V | | | (662) | V P C R F Q - G E S L L K | | | | | |
| RPOB_MORCA | (556) | E V R D M H T T H Y G R V | | | (644) | V S V R H D - G E F V R M | | | | | |
| RPOB_ACIBC | (555) | E V R D M H Q T H Y G R V | | | (643) | V S V R H Q - G E F V R M | | | | | |
| RPOB_PSEAE | (551) | E V R D M H P T H Y G R V | | | (639) | V A V R H L - N E F T V K | | | | | |
| RPOB_STAAU | (501) | E V R D M H Y S H Y G R M | | | (591) | V V C R F R - G N N T V M | | | | } | Non-Mycrobacterial Gram-positive bacterial RNAP |
| RPOB_STAEQ | (501) | E V R D M H Y S H Y G R M | | | (591) | V V C R F R - G N N T V M | | | | | |
| RPOB_ENTFA | (509) | E V R D M H Y S H Y G R M | | | (599) | V M A R L Q - S E N L E V | | | | | |
| RPOB_STRP1 | (506) | E V R D M H Y T H Y G R M | | | (596) | V M G R H Q - G N N Q E F | | | | | |
| RPOB_STRP2 | (506) | E V R D M H Y T H Y G R M | | | (596) | V M G R H Q - G V N Q E Y | | | | | |
| RPOB_CDIFF | (522) | E V R D M H H S H Y G R M | | | (612) | V V C R T V N G A M E M V | | | | | |
| RPOB_THEAQ | (426) | D V R D M H R T H Y G R I | | | (513) | V V A R R K - G E P V I V | | | | } | Thermus-Deniococcus bacterial RNAP |
| RPOB_TTHER | (426) | D V R D M H R T H Y G R I | | | (513) | V V A R R K - G E P V I V | | | | | |
| RPOB_DEIRA | (475) | D V R D M H R T H Y G R I | | | (563) | V L A R R K - G D P L L Y | | | | | |
| RPA2_HUMAN | (429) | T V R R L L P E S W G F L | | | (578) | I G T M E Q I F M N V A I | | | | } | Human RNAP I,II,III |
| RPB2_HUMAN | (497) | K P R Q L H N T L W G M V | | | (665) | I D T L E E E T V M L A M | | | | | |
| RPC2_HUMAN | (467) | G P R S L Q P S Q W G M L | | | (633) | L D V N E E N D C N I A L | | | | | |

FIG. 3A

ANTIBACTERIAL AGENTS: DUAL-TARGETED RNA POLYMERASE INHIBITORS

CROSS-REFERENCE TO RELATED APPLICATION(S)

This application is a 35 U.S.C. § 371 application of International Application No. PCT/US2019/033788, filed May 23, 2019, which claims priority to U.S. Provisional Application No. 62/677,596, filed May 29, 2018 and U.S. Provisional Application No. 62/676,805, filed May 25, 2018.

GOVERNMENT SUPPORT

The invention described herein was made with United States Government support under Grant Number U19-AI109713 awarded by the National Institutes of Health. The United States Government has certain rights in the invention.

BACKGROUND ART

Bacterial infections remain among the most common and deadly causes of human disease. Infectious diseases are the third leading cause of death in the United States and the leading cause of death worldwide (Binder et al. (1999) Science 284, 1311-1313). Multi-drug-resistant bacteria now cause infections that pose a grave and growing threat to public health. It has been shown that bacterial pathogens can acquire resistance to first-line and even second-line antibiotics (Stuart B. Levy, The Challenge of Antibiotic Resistance, in Scientific American, 46-53 (March, 1998); Walsh, C. (2000) Nature 406, 775-781; Schluger, N. (2000) Int. J. Tuberculosis Lung Disease 4, S71-S75; Raviglione et al., (2001) Ann. NY Acad. Sci. 953, 88-97). New approaches to drug development are necessary to combat the ever-increasing number of antibiotic-resistant pathogens.

RNA polymerase (RNAP) is the molecular machine responsible for transcription and is the target, directly or indirectly, of most regulation of gene expression (Ebright, R. (2000) J. Mol. Biol. 304, 687-698; Darst, S. (2001) Curr. Opin. Structl. Biol. 11, 155-162; Murakami, K. and Darst, S. (2003) Curr. Opin. Structl. Biol. 13, 31-39; Borukhov, S. and Nudler, E. (2003) Curr. Opin. Microbiol. 6, 93-100; Werner, F. (2007) Mol. Microbiol. 65, 1395-1404; Hirata, A. and Murakami, K. (2009) Curr. Opin. Structl. Biol. 19, 724-731; Jun, S., Reichlen, M., Tajiri, M. and Murakami, K. (2011) Crit. Rev. Biochem. Mol. Biol. 46, 27-40; Cramer, P. (2002) Curr. Opin. Struct. Biol. 12, 89-97; Cramer, P. (2004) Curr. Opin. Genet. Dev. 14, 218-226; Hahn, S. (2004) Nature Struct. Mol. Biol. 11, 394-403; Kornberg, R. (2007) Proc. Natl. Acad. Sci. USA 104, 12955-12961; Cramer, P., Armache, K., Baumli, S., Benkert, S., Brueckner, F., Buchen, C., Damsma, G., Dengl, S., Geiger, S., Jasiak, A., Jawhari, A., Jennebach, S., Kamenski, T., Kettenberger, Kuhn, C., Lehmann, E., Leike, K., Sydow, J. and Vannini, A. (2008) Annu. Rev. Biophys. 37, 337-352; Lane, W. and Darst, S. (2010) J. Mol. Biol. 395, 671-685; Lane, W. and Darst, S. (2010) J. Mol. Biol. 395, 686-704; Werner, F. and Grohmann, D. (2011) Nature Rev. Microbiol. 9, 85-98; Vannini, A. and Cramer, P. (2012) Mol. Cell 45, 439-446). Bacterial RNAP core enzyme has a molecular mass of ~380,000 Da and consists of one β' subunit, one β subunit, two α subunits, and one ω subunit; bacterial RNAP holoenzyme has a molecular mass of ~450,000 Da and consists of bacterial RNAP core enzyme in complex with the transcription initiation factor σ (Ebright, R. (2000) J. Mol. Biol. 304, 687-698; Darst, S. (2001) Curr. Opin. Structl. Biol. 11, 155-162; Cramer, P. (2002) Curr. Opin. Structl. Biol. 12, 89-97; Murakami and Darst (2003) Curr. Opin. Structl. Biol. 13, 31-39; Borukhov and Nudler (2003) Curr. Opin. Microbiol. 6, 93-100). Bacterial RNAP core subunit sequences are conserved across Gram-positive and Gram-negative bacterial species (Ebright, R. (2000) J. Mol. Biol. 304, 687-698; Darst, S. (2001) Curr. Opin. Structl. Biol. 11, 155-162; Lane, W. and Darst, S. (2010) J. Mol. Biol. 395, 671-685; Lane, W. and Darst, S. (2010) J. Mol. Biol. 395, 686-704;). Eukaryotic RNAP I, RNAP II, and RNAP III contain counterparts of all bacterial RNAP core subunits, but eukaryotic-subunit sequences and bacterial-subunit sequences exhibit only limited conservation (Ebright, R. (2000) J. Mol. Biol. 304, 687-698; Darst, S. (2001) Curr. Opin. Structl. Biol. 11, 155-162; Cramer, P. (2002) Curr. Opin. Structl. Biol. 12, 89-97; Cramer, P. (2004) Curr. Opin. Genet. Dev. 14, 218-226; Lane, W. and Darst, S. (2010) J. Mol. Biol. 395, 671-685; Lane, W. and Darst, S. (2010) J. Mol. Biol. 395, 686-704).

Crystal structures have been determined for bacterial RNAP and eukaryotic RNAP II (Zhang et al., (1999) Cell 98, 811-824; Cramer et al., (2000) Science 288, 640-649; Cramer et al., (2001) Science 292, 1863-1876).

Structures also have been determined for RNAP complexes with nucleic acids, nucleotides and inhibitors (Campbell, et al. (2001) Cell 104, 901-912; Artsimovitch, et al. (2005) Cell 122, 351-363; Campbell, et al. (2005) EMBO J. 24, 674-682; Tuske, et al. (2005) Cell 122, 541-522; Temiaov, et al. (2005) Mol. Cell 19, 655-666; Mukhopadhyay, J., Das, K., Ismail, S., Koppstein, D., Jang, M., Hudson, B., Sarafianos, S., Tuske, S., Patel, J., Jansen, R., Irschik, H., Arnold, E., and Ebright, R. (2008) Cell 135, 295-307; Belogurov, G., Vassylyeva, M., Sevostyanova, A., Appleman, J., Xiang, A., Lira, R., Webber, S., Klyuyev, S., Nudler, E., Artsimovitch, I., and Vassylyev, D. (2009) Nature. 45, 332-335; Vassylyev, D., Vassylyeva, M., Perederina, A., Tahirov, T. and Artsimovitch, I. (2007) Nature 448, 157-162; Vassylyev, D., Vassylyeva, M., Zhang, J., Palangat, M., Artsimovitch, I. and Landick, R. (2007) Nature 448, 163-168; Gnatt, et al. (2001) Science 292, 1876-1882; Westover, et al. (2004a) Science 303, 1014-1016; Westover, et al. (2004b) Cell 119, 481-489; Ketenberger, et al. (2004) Mol. Cell 16, 955-965; Bushnell, et al. (2002) Proc. Natl. Acad. Sci. U.S. A. 99, 1218-1222; Kettenberger, et al. (2005) Natl. Structl. Mol. Biol. 13, 44-48; Ho, M., Hudson, B., Das, K., Arnold, E. and Ebright, R. (2009) Curr. Opin. Structl. Biol. 19, 715-723).

Bacterial RNAP is a proven target for antibacterial therapy (Darst, S. (2004) Trends Biochem. Sci. 29, 159-162; Chopra, I. (2007) Curr. Opin. Investig. Drugs 8, 600-607; Villain-Guillot, P., Bastide, L., Gualtieri, M. and Leonetti, J. (2007) Drug Discov. Today 12, 200-208; Mariani, R. and Maffioli, S. (2009) Curr. Med. Chem. 16, 430-454; Ho, M., Hudson, B., Das, K., Arnold, E. and Ebright, R. (2009) Curr. Opin. Structl. Biol. 19, 715-723; Srivastava, A., Talaue, M., Liu, S., Degen, D., Ebright, R. Y., Sineva, E., Chakraborty, A., Druzhinin, S., Chatterjee, S., Mukhopadhyay, J., Ebright, Y., Zozula, A., Shen, J., Sengupta, S., Niedfeldt, R., Xin, C., Kaneko, T., Irschik, H., Jansen, R., Donadio, S., Connell, N. and Ebright, R. H. (2011) Curr. Opin. Microbiol. 14, 532-543). The suitability of bacterial RNAP as a target for antibacterial therapy follows from the fact that bacterial RNAP is an essential enzyme (permitting efficacy), the fact that bacterial RNAP subunit sequences are conserved (providing a basis for broad-spectrum activity), and the fact that bacterial RNAP subunit sequences are only weakly conserved in eukaryotic RNAP I, RNAP II, and RNAP III (providing a basis for therapeutic selectivity).

The rifamycin antibacterial agents—notably rifampin, rifapentine, and rifabutin—function by binding to and inhibiting bacterial RNAP (Darst, S. (2004) *Trends Biochem. Sci.* 29, 159-162; Ho, M., Hudson, B., Das, K., Arnold, E. and Ebright, R. (2009) *Curr. Opin. Structl. Biol.* 19, 715-723; Floss and Yu (2005) *Chem. Rev.* 105, 621-632; Campbell, et al. (2001) *Cell* 104, 901-912; Artsimovitch, et al. (2005) *Cell* 122, 351-363; Feklistov, A., Mekler, V., Jiang, Q., Westblade, L., Irschik, H., Jansen, R., Mustaev, A., Darst, S., and Ebright, R. (2008) *Proc. Natl. Acad. Sci. USA* 105, 14820-14825). The rifamycins bind to a site on bacterial RNAP adjacent to the RNAP active center and prevent the extension of RNA chains beyond a length of 2-3 nt.

The rifamycins are in current clinical use in treatment of Gram-positive and Gram-negative bacterial infections (Darst, S. (2004) *Trends Biochem. Sci.* 29, 159-162; Ho, M., Hudson, B., Das, K., Arnold, E. and Ebright, R. (2009) *Curr. Opin. Structl. Biol.* 19, 715-723; Floss and Yu (2005) *Chem. Rev.* 105, 621-632; Campbell, et al. (2001) *Cell* 104, 901-912). The rifamycins are first-line treatments for tuberculosis and are the only current first-line treatments for tuberculosis able to kill non-replicating tuberculosis bacteria, to clear infection, and to prevent relapse (Mitchison, D. (2000) *Int. J. Tuberc. Lung Dis.* 4, 796-806). The rifamycins also are first-line treatments for biofilm-associated infections of catheters and implanted medical devices and are among the very few current antibacterial drugs able to kill non-replicating biofilm-associated bacteria (Obst, G., Gagnon, R. F., Prentis, J. and Richards, G. K. (1988) *ASAIO Trans.* 34, 782-784; Obst, G., Gagnon, R. F., Harris, A., Prentis, J. and Richards, G. K. (1989)*Am. J. Nephrol.* 9, 414-420; Villain-Guillot, P., Gualtieri, M., Bastide, L. and Leonetti, J. P. (2007) *Antimicrob. Agents Chemother.* 51, 3117-3121.

The clinical utility of the rifamycin antibacterial agents is threatened by the emergence and spread of bacterial strains resistant to known rifamycins (Darst, S. (2004) *Trends Biochem. Sci.* 29, 159-162; Ho, M., Hudson, B., Das, K., Arnold, E. and Ebright, R. (2009) *Curr. Opin. Structl. Biol.* 19, 715-723; Floss and Yu (2005) *Chem. Rev.* 105, 621-632; Campbell, et al. (2001) *Cell* 104, 901-912). Resistance to rifamycins typically involves substitution of residues in or immediately adjacent to the rifamycin binding site on bacterial RNAP—i.e., substitutions that directly decrease binding of rifamycins. A significant and increasing percentage of cases of tuberculosis are resistant to rifampicin (1.4% of new cases, 8.7% of previously treated cases, and 100% of cases designated multidrug-resistant, in 1999-2002; Schluger, N. (2000) *Int. J. Tuberc. Lung Dis.* 4, S71-S75; Raviglione, et al. (2001) *Ann. N.Y. Acad. Sci.* 953, 88-97; Zumia, et al. (2001) *Lancet Infect. Dis.* 1, 199-202; Dye, et al. (2002) *J. Infect. Dis.* 185, 1197-1202; WHO/IUATLD (2003) *Anti-tuberculosis drug resistance in the world: third global report* (WHO, Geneva)). Strains of bacterial bioweapons agents resistant to rifampicin can be, and have been, constructed (Lebedeva, et al. (1991) *Antibiot. Khimioter.* 36, 19-22; Pomerantsev, et al. (1993) *Antibiot. Khimioter.* 38, 34-38; Volger, et al. (2002) *Antimicrob. Agents Chemother.* 46, 511-513; Marianelli, et al. (204) *J. Clin. Microbiol.* 42, 5439-5443).

In view of the public-health threat posed by rifamycin-resistant bacterial infections, there is an urgent need for new antibacterial agents that target bacterial RNAP and an especially urgent need for new antibacterial agents that target bacterial RNAP derivatives resistant to known rifamycins.

(See Darst, S. (2004) *Trends Biochem. Sci.* 29, 159-162; Chopra, I. (2007) *Curr. Opin. Investig. Drugs* 8, 600-607; Villain-Guillot, P., Bastide, L., Gualtieri, M. and Leonetti, J. (2007) *Drug Discov. Today* 12, 200-208; Mariani, R. and Maffioli, S. (2009) *Curr. Med. Chem.* 16, 430-454; Ho, M., Hudson, B., Das, K., Arnold, E. and Ebright, R. (2009) *Curr. Opin. Structl. Biol.* 19, 715-723; Srivastava, A., Talaue, M., Liu, S., Degen, D., Ebright, R. Y., Sineva, E., Chakraborty, A., Druzhinin, S., Chatterjee, S., Mukhopadhyay, J., Ebright, Y., Zozula, A., Shen, J., Sengupta, S., Niedfeldt, R., Xin, C., Kaneko, T., Irschik, H., Jansen, R., Donadio, S., Connell, N. and Ebright, R. H. (2011) *Curr. Opin. Microbiol.* 14, 532-543.)

SUMMARY OF THE INVENTION

Applicant has identified compounds that inhibit bacterial RNA polymerase (RNAP) and inhibit bacterial growth. Accordingly, in one embodiment the invention provides a compound of formula (I):

$$X\text{-}\alpha\text{-}Y \qquad (I)$$

or a salt thereof, wherein:

X is a moiety that binds to the Rif target of a bacterial RNAP;

Y is a moiety that binds to the bridge-helix N-terminus target of a bacterial RNAP; and α is a covalent bond or a linker.

The invention also provides a method for making a compound of formula I, wherein the compound is prepared from precursors X-α' and 'α-Y, where α' and 'α are moieties that can react to form α.

The invention also provides a use of a compound of the invention to bind to a bacterial RNAP.

The invention also provides a use of a compound of the invention to inhibit a bacterial RNAP.

The invention also provides a use of a compound of the invention to inhibit bacterial gene expression.

The invention also provides a use of a compound of the invention to inhibit bacterial growth.

The invention also provides a use of a compound of the invention to inhibit a bacterial infection.

The invention also provides a composition comprising a compound of the invention or a pharmaceutically acceptable salt thereof and a pharmaceutically acceptable vehicle.

The invention also provides a method for inhibiting the growth of bacteria comprising contacting the bacteria with a compound of the invention or a salt thereof.

The invention also provides a method for inhibiting a bacterial RNA polymerase comprising contacting the bacterial RNA polymerase with a compound of the invention or a salt thereof.

The invention also provides a method for treating a bacterial infection in a mammal, e.g., a human, comprising administering to the mammal an effective amount of a compound of the invention or a pharmaceutically acceptable salt thereof.

The invention also provides a compound of the invention or a pharmaceutically acceptable salt thereof for use in the prophylactic or therapeutic treatment of a bacterial infection.

The invention also provides the use of a compound of the invention or a pharmaceutically acceptable salt thereof for the preparation of a medicament for treating a bacterial infection in a mammal, e.g., a human.

The invention also provides a compound of the invention or a pharmaceutically acceptable salt thereof for use in medical treatment.

The invention provides a new class of inhibitors of bacterial RNAP. Importantly, the invention provides inhibitors that can exhibit potencies higher than those of known inhibitors. Especially importantly, the invention provides inhibitors that can inhibit bacterial RNAP derivatives resistant to known inhibitors.

The invention provides new compositions of matter that inhibit a bacterial RNA polymerase and inhibit bacterial growth. The compounds are anticipated to have applications in analysis of RNAP structure and function, control of bacterial gene expression, control of bacterial growth, antibacterial prophylaxis, antibacterial therapy, and drug discovery.

Compounds of this invention consist of a rifamycin RNAP inhibitor (an entity that inhibits a bacterial RNAP by binding to the RNAP Rif pocket) linked to an Nα-aroyl-N-aryl-phenylalaninamide (AAP; an entity that inhibits bacterial RNAP by binding to the RNAP bridge-helix N-terminus).

Certain compounds of this invention inhibit a bacterial RNAP and inhibit growth of bacteria more potently than a rifamycin or an AAP.

Certain compounds of this invention may inhibit a rifamycin-resistant bacterial RNAP and inhibit growth of rifamycin-resistant bacteria much more potently than a rifamycin.

Certain compounds of this invention inhibit a MP-resistant bacterial RNAP and inhibit growth of rifamycin-resistant bacteria much more potently than an AAP.

Compounds of this invention have particularly potent effects against drug-sensitive and drug-resistant RNAP from Mycobacteria, including *Mycobacterium tuberculosis*, *Mycobacterium avium*, and *Mycobacterium abscessus*.

Certain compounds of this invention have particularly potent effects against growth of drug-sensitive and drug-resistant Mycobacteria, including *Mycobacterium tuberculosis*, *Mycobacterium avium*, and *Mycobacterium abscessus*.

The invention provides bipartite, dual-targeted inhibitors of bacterial RNAP that contain: (i) a first moiety, X, that binds to the rifamycin binding site ("Rif target"; also known as "Rif/Sor target") of bacterial RNAP; (ii) a second moiety, Y, that binds to the bridge-helix N-terminus target of a bacterial RNAP; and (iii) a linker α connecting said first and second moieties.

The invention provides bipartite, dual-targeted inhibitors that interact with bacterial RNAP through alternative interactions of X with the Rif target or Y with the bridge-helix N-terminus target of a bacterial RNAP. The ability of the bipartite inhibitors to interact with a bacterial RNAP alternatively through two moieties, X or Y, can result in simultaneous interactions of two molecules of bipartite inhibitor with RNAP, conferring an additive or super-additive inhibitory effects. The ability of the bipartite inhibitors to interact with RNAP alternatively through two moieties, X and Y, also can confer an ability to interact with a bacterial RNAP derivative resistant to X or Y.

The bipartite, dual-targeted inhibitors have applications in control of bacterial gene expression, control of bacterial growth, antibacterial chemistry, and antibacterial therapy.

The invention also provides intermediates and processes useful for preparing compounds of the invention.

The invention provides a method for preparing a compound that contains: (i) a first moiety, X, that binds to the rifamycin binding site ("Rif target"; also known as Rif/Sor target") of bacterial RNAP; (ii) a second moiety, Y, that binds to the bridge-helix N-terminus target of a bacterial RNAP; and (iii) a linker, α, connecting said first and second moieties. The method includes providing precursors X-α' and 'α-Y, and reacting moieties α' and 'α to form α. For example, one precursor may contain an aldehyde, a ketone, a protected aldehyde, or a protected ketone, and the other precursor contain a hydrazide or an amine. One precursor may contain an activated ester, an imidazolide, or an anhydride, and the other precursor contain an amine. One precursor may contain a halogen, and the other precursor contain an amine. One precursor may contain a halogen, and the other precursor contain a sulfhydryl. One precursor may contain an azide and the other precursor contain an alkyne. One precursor may contain an azide, and the other precursor contain a phosphine. One precursor may contain a boronic acid, and the other precursor contain a substituted phenol. One precursor may contain a phenylboronic acid, and the other precursor contain salicylhydroxamic acid.

These and other aspects of the present invention will be better appreciated by reference to the following drawings and Detailed Description.

BRIEF DESCRIPTION OF THE DRAWINGS

FIG. 1 shows a sequence alignment defining the Rif target of bacterial RNAP. The sequence alignment shows amino acid residues 146, 148, 507-509, 511-513, 516, 518, 522-523, 525-526, 529, 531-534, 568, 572, 574, and 687 of the β subunit of RNAP from *Escherichia coli*; and corresponding residues of the β subunits of *Haemophilus influenzae*, *Vibrio cholerae*, *Pseudomonas aeruginosa*, *Treponema pallidum*, *Borrelia burgdorferi*, *Xylella fastidiosa*, *Campylobacter jejuni*, *Neisseria meningitides*, *Rickettsia prowazekii*, *Thermotoga maritime*, *Chlamydia trachomatis*, *Mycoplasma pneumoniae*, *Bacillus subtilis*, *Staphylococcus aureus*, *Mycobacterium tuberculosis*, *Synechocystis* sp., *Aquifex aeolicus*, *Deinococcus radiodurans*, *Thermus thermophilus*, and *Thermus aquaticus* (collectively, the "Rif target"); and corresponding residues of the second-largest subunits of human RNAP I, RNAP II and RNAP III.

FIGS. 3A-3B show a sequence alignment defining the bridge-helix N-terminus target of bacterial RNAP. The sequence alignment shows amino acid residues 550, 552, 555, 637, 640 and 642 of the β subunit and (FIG. 3A) 749, 750, 755, and 757 of theβ' subunit (FIG. 3B) of RNAP from *Escherichia coli* (ECOLI), and corresponding residues of the β and β' subunits of *Mycobacterium tuberculosis* (MYCTU), *Mycobacterium avium* (MYCA1), *Mycobacterium abscessus* (MYCA9), *Mycobacterium smegmatis* (MYCSM), *Salmonella typhimurium* (SALTY), *Klebsiella pneumoniae* (KLEP7), *Enterococcus cloacae* (ENTCC), *Vibrio* cholerae (VIBCH), Haemophilus influenzae (HAEIN), Neisseria gonorrhoeae (NEIG1), Stenotrophomonas maltophilia (STPMP), Moraxella catarrhalis (MORCA), Acinetobacter baumannii (ACIBC), Pseudomonas aeruginosa (PSEAE), Staphylococcus aureus (STAAU), Staphylococcus epidermidis (STAEQ), Enterococcus faecalis (ENTFA), Streptococcus pyogenes (STRP1), Streptococcus pneumoniae (STRP2), Clostridium difficile (CDIFF), Thermus thermophilus (THETH), Thermus aquaticus (THEAQ), and Deinococcus radiodurans (DEIRA) (collectively, the "bridge-helix N-terminus target"); and corresponding residues of the second-largest subunits of human RNAP I, RNAP II, and RNAP III. Defining residues of the bridge-helix N-terminus target are boxed and are numbered at top as in Escherichia coli RNAP (in parentheses) and as in Mycobacterium tuberculosis RNAP.

Figure 4:
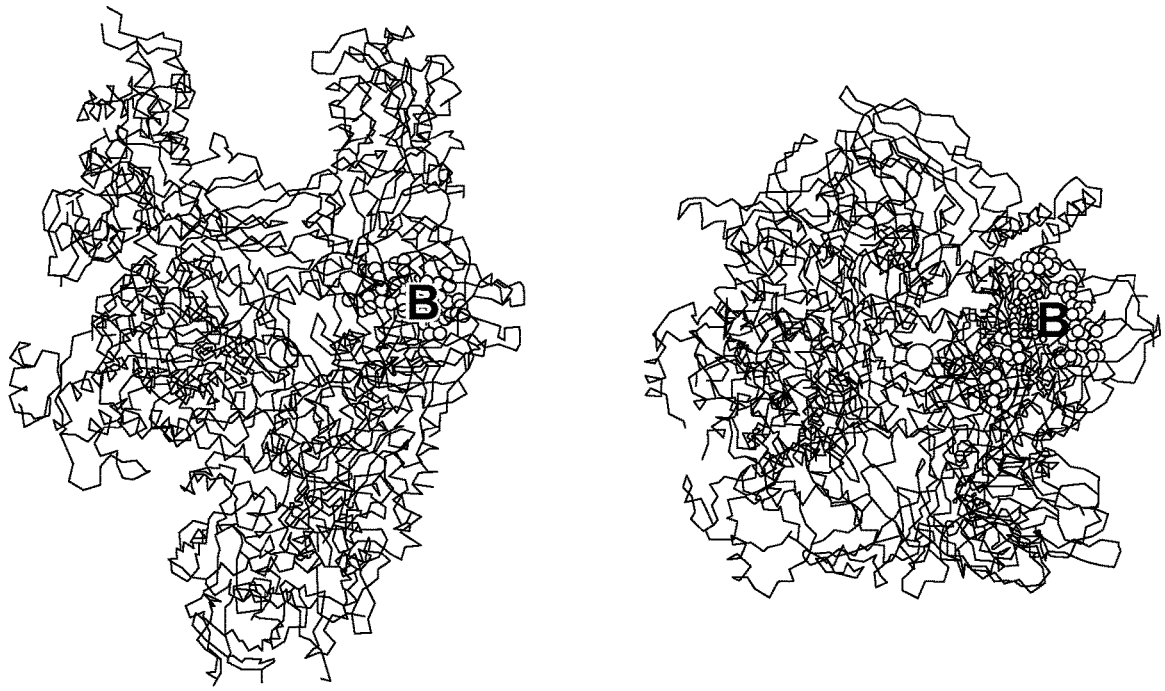

FIG. 4 shows the position of the bridge-helix N-terminus within the three-dimensional structure of bacterial RNAP (two orthogonal views). Sites of amino acid substitutions that confer AAP-resistance and/or CBR-resistance are shown as a dark gray solid surface (labelled B; Artsimovitch, I., Chu, C., Lynch, A. S., and Landick, R. (2003). Science 302, 650-654; Feng, Y., Degen, D., Wang, X., Gigliotti, M., Liu, S., Zhang, Y., Das, D., Michalchuk, T., Ebright, Y. W., Talaue, M., Connell, N., and Ebright, R. H. (2015). Structure 23, 1470-1481; Bae, B., Nayak, D., Ray, A., Mustaev, A., Landick, R., and Darst, S. A. (2015). Proc. Natl. Acad. Sci. USA 112, E4178-E4187; Ebright, R. H., Ebright, Y., Mandal, S., Wilde, R., and Li, S. (2015) WO2015/120320; Lin, W., Mandal, S., Degen, D., Liu, Y., Ebright, Y. W., Li, S., Feng, Y., Zhang, Y., Mandal, S., Jiang, Y., Liu, S., Gigliotti, M., Talaue, M., Connell, N., Das, K., Arnold, E., and Ebright, R. H. (2017) Mol. Cell 66, 169-179). RNAP backbone atoms are shown in a Cα representation. The RNAP active-center Mg2+ is shown as a sphere.

Figure 5:
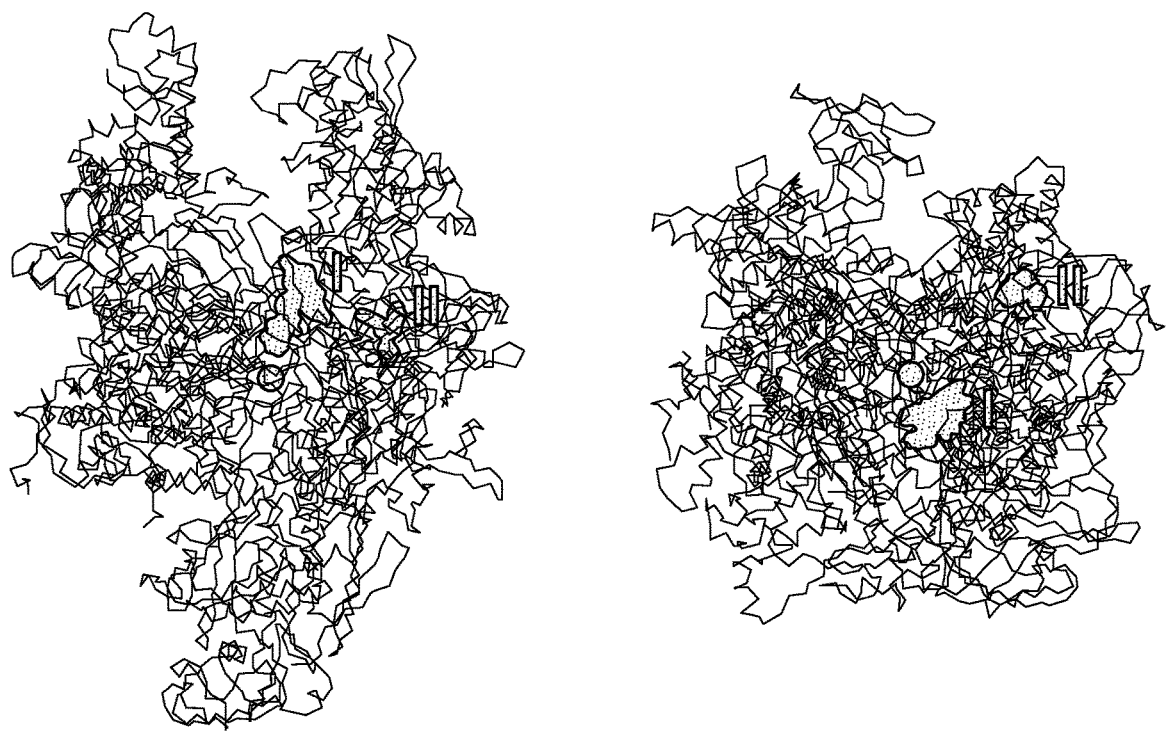

FIG. 5 shows a crystal structure of IX-404a bound to a Mycobacterium tuberculosis transcription initiation complex. Two molecules of IX-404a bind simultaneously to RNAP; one molecule of IX-404a binds, through its Rif moiety, to the Rif target of RNAP (dark gray solid surface labelled I); and another molecule of IX-404a binds, through its AAP moiety, to the bridge-helix N-terminus target of RNAP (dark gray solid surface labelled II).

DETAILED DESCRIPTION OF THE INVENTION

Definitions

The following definitions are used, unless otherwise indicated.

Unless otherwise specified, the term "binds" used herein refers to high-affinity specific binding (i.e., an interaction for which the equilibrium dissociation constant, Kd, is less than about 100 μM and preferably is less than about 10 μM).

Unless otherwise specified, the term "rifamycin" used herein encompasses both the napthol (reduced) and naptho-quinone (oxidized) forms of a rifamycin, and both the 25-O-acetyl and 25-OH forms of a rifamycin (see Sensi, P., Maggi, N., Furesz, S. and Maffei, G. (1966) Antimicrobial Agents Chemother 6, 699-714; Rinehart, K. (1972) Accts. Chem. Res. 5, 57-64; Wehrli (1977) Topics Curr. Chem. 72, 21-49; Floss, et al. (2005) Chem. Rev. 105, 621-632; Aristoff, P., Garcia, G. A., Kirchoff, P. and Showalter, H. D. H. (2010) Tuberculosis 90, 94-118).

Unless otherwise specified, structures depicted herein are intended to include all stereochemical forms of the structure; i.e., the R and S configurations for each asymmetric center. Therefore, single stereochemical isomers, as well as enantiomeric and diastereomeric mixtures, of the present compounds are within the scope of the invention.

Unless otherwise specified, structures depicted herein are intended to include compounds which differ only in the presence of one or more isotopically enriched atoms. For example, compounds having the present structures, except for the replacement of a hydrogen atom by a deuterium atom or a tritium atom, or except for the replacement of a carbon by a $^{13}$C- or $^{14}$C-enriched carbon atom, are within the scope of this invention.

Compounds of this invention may exist in tautomeric forms, such as keto-enol tautomers. The depiction of a single tautomer is understood to represent the compound in all of its tautomeric forms.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The pharmaceutically acceptable salt may also be a salt of a compound of the present invention having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-

(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

Bipartite, Dual-Targeted Inhibitors of RNAP

Certain embodiments of the invention provide a new class of inhibitors of RNAP. Certain embodiments of the invention provide novel inhibitors of RNAP that kill bacterial pathogens more potently than current inhibitors. For example, certain embodiments exhibit inhibition activities higher than known inhibitors. Another aspect of the invention is the provision of novel inhibitors of RNAP that kill bacterial pathogens resistant to current inhibitors.

Certain embodiments of the invention provide a compound of formula (I):

$$X\text{-}\alpha\text{-}Y \qquad (I)$$

wherein: X comprises a moiety that binds to the Rif target of a bacterial RNAP; Y a moiety that binds to the bridge-helix N-terminus target of a bacterial RNAP; α is a covalent bond or a linker.

It is understood that when α is a covalent bond, the covalent bond can be formed between any synthetically feasible position on X and any synthetically feasible position on Y, provided the resulting compound has the requisite binding affinities. Additionally, when α is a linker, α can be attached to any synthetically feasible position on X and any synthetically feasible position on Y, provided the resulting compound has the requisite binding affinities.

Moiety that Binds to the Rifamycin Target of a Bacterial RNA Polymerase (X)

Figure 1:
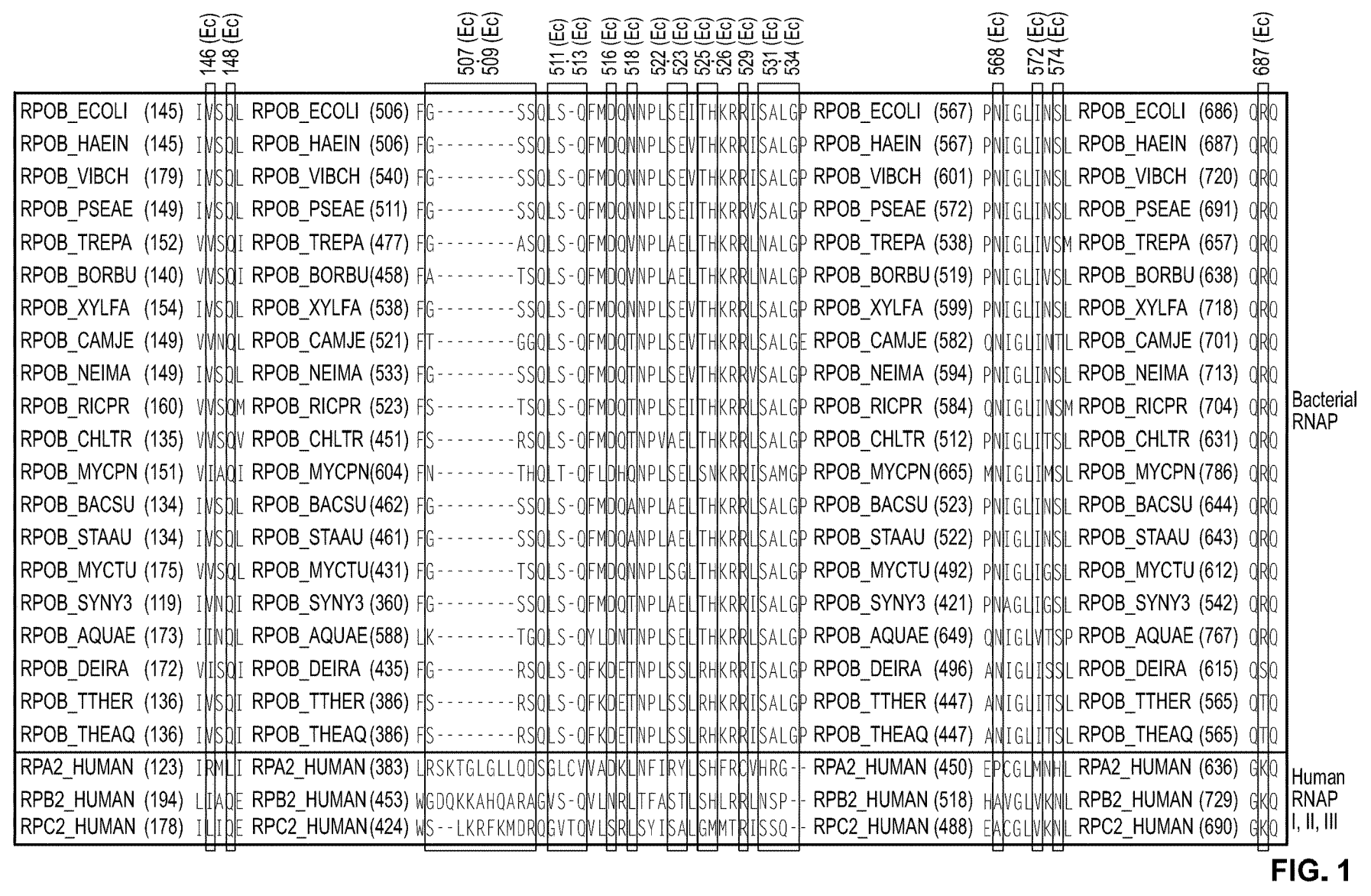
Figure 2:
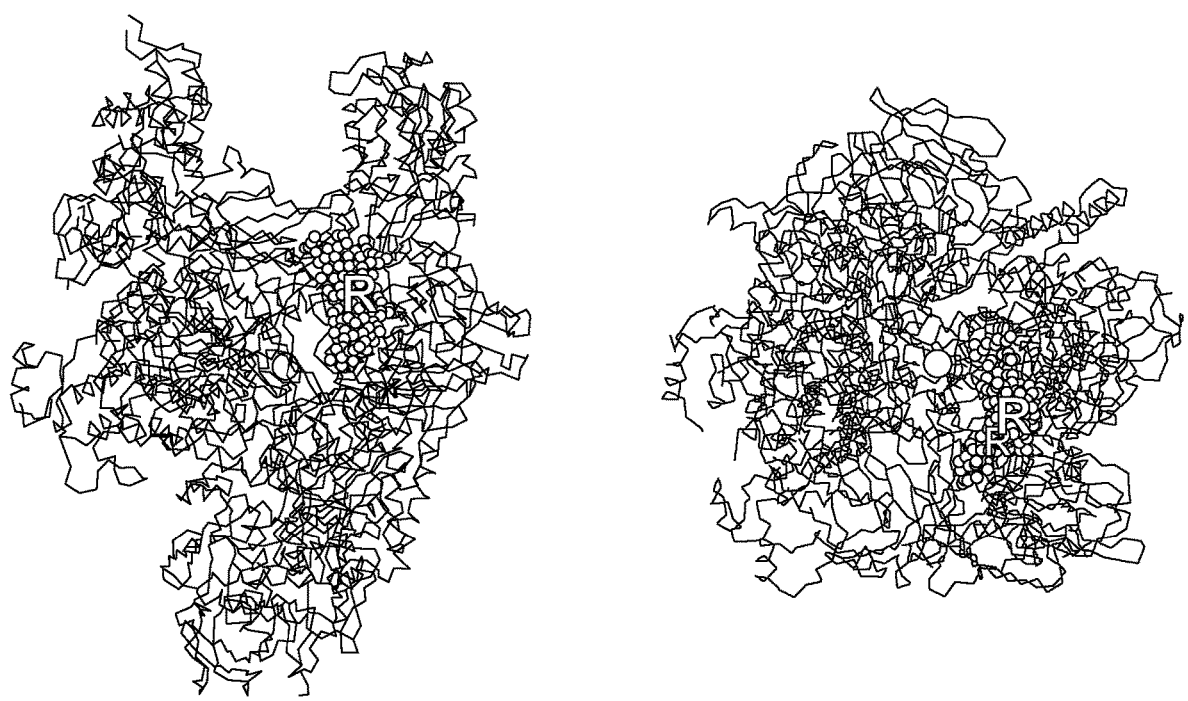
FIG. 2 shows the position of the Rif target within the three-dimensional structure of bacterial RNAP (two orthogonal views). Sites of amino acid substitutions that confer rifamycin-resistance are shown as a dark gray solid surface (labelled R; Ovchinnikov, Y., Monastyrskaya, G., Gubanov, V., Lipkin, V., Sverdlov, E., Kiver, I., Bass, I., Mindlin, S., Danilevskaya, O., and Khesin, R. (1981) *Mol. Gen. Genet.* 184, 536-538; Ovchinnikov, Y., Monastyrskaya, G., Guriev, S., Kalinina, N., Sverdlov, E., Gragerov, A., Bass, I., Kiver, I., Moiseyeva, E., Igumnov, V., Mindlin, S., Nikiforov, V. and Khesin, R. (1983) *Mol. Gen. Genet.* 190, 344-348; Jin, D. J., and Gross, C. (1988) *J. Mol. Biol.* 202, 45-58; Severinov, K., Soushko, M., Goldfarb, A., and Nikiforov, V. (1993) *J. Biol. Chem.* 268, 14820-14825; Ho, M., Hudson, B., Das, K., Arnold, E. and Ebright, R. (2009) *Curr. Opin. Structl. Biol.* 19, 715-723). RNAP backbone atoms are shown in a Cα representation. The RNAP active-center $Mg^{2+}$ is shown as a sphere.

A region located within the RNAP active-center cleft—a region that comprises amino acids 146, 148, 507-509, 511-513, 516, 518, 522-523, 525-526, 529, 531-534, 568, 572, 574, and 687 of the RNAP β subunit in RNAP from *Escherichia coli*—is a useful target for compounds that inhibit transcription, including, by way of example, rifamycins, streptovaricins, tolypomycins, and sorangicins (Sensi, P., Maggi, N., Furesz, S. and Maffei, G. (1966) *Antimicrobial Agents Chemother* 6, 699-714; Rinehart (1972) *Accts. Chem. Res.* 5, 57-64; Wehrli (1977) *Topics Curr. Chem.* 72, 21-49; Campbell, et al. (2001) *Cell* 104, 901-912; Artsimovitch, et al. (2005) *Cell* 122, 351-363; Floss, et al. (2005) *Chem. Rev.* 105, 621-632; Aristoff, P., Garcia, G. A., Kirchoff, P. and Showalter, H. D. H. (2010) *Tuberculosis* 90, 94-118; Nitta, et al. (1968) *J. Antibiotics* 21, 521-522; Morrow, et al. (1979) *J. Bacteriol.* 137, 374-383; Kondo, et al. (1972) *J. Antibiotics* 25, 16-24; Rommelle, et al. (1990) *J. Antibiotics* 43, 88-91; O'Neill, et al. (2000) *Antimicrobial Agents Chemother.* 44, 3163-3166; Campbell, et al. (2005) *EMBO J.* 24, 1-9; Ho, M., Hudson, B., Das, K., Arnold, E. and Ebright, R. (2009) *Curr. Opin. Structl. Biol.* 19, 715-723; Lin, W., Mandal, S., Degen, D., Liu, Y., Ebright, Y. W., Li, S., Feng, Y., Zhang, Y., Mandal, S., Jiang, Y., Liu, S., Gigliotti, M., Talaue, M., Connell, N., Das, K., Arnold, E., and Ebright, R. H. (2017) *Mol. Cell* 66, 169-179; FIGS. 1,2). This region is referred to herein as the "Rif target," reflecting the fact that it serves as the binding site for rifamycins, among other compounds.

The Rif target includes residues that are invariant or nearly invariant in RNAP from bacterial species, but that are radically different in RNAP from eukaryotic species (FIG. 1). The Rif target forms a shallow pocket within the wall of the RNAP active-center cleft (FIG. 2). A compound that binds to the Rif target of a bacterial RNAP can block bacterial RNA synthesis (e.g., by sterically blocking extension of RNA chains beyond a length of 2-3 nt), can inhibit bacterial gene expression, and can inhibit bacterial growth.

The Rif target referred to above in RNAP from *Escherichia coli* is similar in amino acid sequence in RNAP from most or all species of bacteria (FIG. 1). For example, amino acid residues 146, 148, 507-509, 511-513, 516, 518, 522-523, 525-526, 529, 531-534, 568, 572, 574, and 687 of the β subunit of RNAP from *Escherichia coli* exhibit high similarity to amino acid residues 135-137, 463-465, 467-469, 472, 474, 478-479, 481-482, 485, 487-490, 524, 526, and 645 of the β subunit of RNAP from *Bacillus subtilis* (FIG. 1). Thus, a molecule that binds to the Rif target of, and inhibits RNA synthesis by, RNAP from *Escherichia coli* also is likely to bind to the Rif target of, and inhibit RNA synthesis by, RNAP from other species of bacteria.

In contrast, the Rif target differs radically in amino acid sequence between bacterial RNAP and eukaryotic RNAP, including human RNAP I, human RNAP II, and human RNAP III (FIG. 1). This allows for the identification of molecules that bind, in a Rif-target-dependent fashion, to a bacterial RNAP, but that do not bind, or that bind substantially less well, to a eukaryotic RNAP. This also allows for the identification of molecules that inhibit, in a Rif-target-dependent fashion, an activity of a bacterial RNAP, but that do not inhibit, or that inhibit substantially less well, an activity of a eukaryotic RNAP. This differentiation is important, because it permits the identification of bacterial-RNAP-selective binding molecules and bacteria-selective inhibitors.

Ligands that bind to the Rif target of, and inhibit RNA synthesis by, a bacterial RNAP are known in the art. Such ligands include, for example, rifamycins (a class of compounds that includes, for example, rifamycin SV, rifamycin S, rifamycin B, rifampin, rifapentine, and rifabutin), streptovaricins, tolypomycins, and sorangicins (Sensi, P., Maggi, N., Furesz, S. and Maffei, G. (1966) *Antimicrobial Agents Chemother* 6, 699-714; Rinehart (1972) *Accts. Chem. Res.* 5, 57-64; Wehrli (1977) *Topics Curr. Chem.* 72, 21-49; Campbell, et al. (2001) *Cell* 104, 901-912; Artsimovitch, et al. (2005) *Cell* 122, 351-363; Floss, et al. (2005) *Chem. Rev.* 105, 621-632; Aristoff, P., Garcia, G. A., Kirchoff, P. and Showalter, H. D. H. (2010) *Tuberculosis* 90, 94-118; Nitta, et al. (1968) *J. Antibiotics* 21, 521-522; Morrow, et al. (1979) *J. Bacteriol.* 137, 374-383; Kondo, et al. (1972) *J. Antibiotics* 25, 16-24; SOR: Rommelle, et al. (1990) *J. Antibiotics* 43, 88-91; O'Neill, et al. (2000) *Antimicrobial Agents Chemother.* 44, 3163-3166; Campbell, et al. (2005) *EMBO J.* 24, 1-9; Ho, M., Hudson, B., Das, K., Arnold, E. and Ebright, R. (2009) *Curr. Opin. Structl. Biol.* 19, 715-723; Lin, W., Mandal, S., Degen, D., Liu, Y., Ebright, Y. W., Li, S., Feng, Y., Zhang, Y., Mandal, S., Jiang, Y., Liu, S., Gigliotti, M., Talaue, M., Connell, N., Das, K., Arnold, E., and Ebright, R. H. (2017) *Mol. Cell* 66, 169-179). The references cited above are incorporated herein in their entirety.

Resistance to rifamycins, streptovaricins, tolypomycins, and sorangicins arises from mutations that result in amino acid substitutions in, or immediately adjacent to Rif target (Campbell, et al. (2001) *Cell* 104, 901-912; Artsimovitch, et al. (2005) *Cell* 122, 351-363; Floss, et al. (2005) *Chem. Rev.* 105, 621-632; Aristoff, P., Garcia, G. A., Kirchoff, P. and Showalter, H. D. H. (2010) *Tuberculosis* 90, 94-118; O'Neill, et al. (2000) *Antimicrobial Agents Chemother.* 44, 3163-3166; Campbell, et al. (2005) *EMBO J.* 24, 1-9; Ho, M., Hudson, B., Das, K., Arnold, E. and Ebright, R. (2009) *Curr. Opin. Structl. Biol.* 19, 715-723).

Rifamycins are a class of antibiotics known in the art (for example, see WO 07/089310, pages 3-5 and 9). For example, this class includes rifamycin A, rifamycin B, rifamycin C, rifamycin D, rifamycin E, rifamycin S, and rifamycin SV. Additionally, derivatives of rifamycins are known in the art and include, for example, rifampicin (rifampin), rifapentine, rifaximin, rifalazil, and rifabutin.

In certain embodiments, X is selected from a rifamycin, a streptovaricin, a tolypomycin, a sorangicin and derivatives thereof.

In certain embodiments, X is a rifamycin or a rifamycin derivative.

In certain embodiments, X is bonded to α through one of C3 of the rifamycin fused ring system, a moiety pendant from C3 of the rifamycin fused ring system, C4 of the rifamycin fused ring system, a moiety pendant from C4 of the rifamycin fused ring system C11 of the rifamycin fused ring system, and a moiety pendant from C11 of the rifamycin fused ring system.

In certain embodiments, X is rifamycin S, and e.g., X is bonded to α through C3 of the rifamycin S fused ring system or a moiety pendant from C3 of the rifamycin S fused ring system.

In certain embodiments, X is rifamycin SV, and e.g., X is bonded to α through C3 of the rifamycin SV fused ring system or a moiety pendant from C3 of the rifamycin SV fused ring system.

In certain embodiments, X is rifamycin S, and e.g., X is bonded to α through C4 of the rifamycin SV fused ring system or a moiety pendant from C4 of the rifamycin S fused ring system.

In certain embodiments, X is rifamycin SV, and e.g., X is bonded to α through C4 of the rifamycin SV fused ring system or a moiety pendant from C4 of the rifamycin SV fused ring system.

In certain embodiments, X is rifamycin SV, and e.g., X is bonded to α through the oxygen atom pendant from C4 of the rifamycin SV fused ring system.

In certain embodiments, X is a sorangicin or a sorangicin derivative.

In certain embodiments, X is bonded to α through the sorangicin sidechain.

In certain embodiments, X is bonded to α through the carboxyl carbon of the sorangicin sidechain.

In certain embodiments, X is sorangicin A, and e.g., X is bonded to α through the carboxyl carbon of the sorangicin A sidechain.

When X is a rifamycin derivative, it is preferred that X is bonded to the α linker through the rifamycin fused ring system, most preferably, through at least one of the C3 atom, an atom pendant from the C3 atom, the C4 atom, an atom pendant from the C4 atom, the C11 atom, and an atom pendant from the C11 atom [representing atoms that, in the three-dimensional structures of RNAP-rifamycin complexes (see Campbell, et al. (2001) Cell 104, 901-912; Artsimovitch, et al. (2005) Cell 122, 351-363; Lin, W., Mandal, S., Degen, D., Liu, Y., Ebright, Y. W., Li, S., Feng, Y., Zhang, Y., Mandal, S., Jiang, Y., Liu, S., Gigliotti, M., Talaue, M., Connell, N., Das, K., Arnold, E., and Ebright, R. H. (2017) Mol. Cell 66, 169-179), are not involved in RNAP-rifamycin interactions and thus that can be functionalized without loss of RNAP-rifamycin interactions].

By way of example, when X is a rifamycin derivative, X can be bonded to the α linker though one of an amino linkage, a thioether linkage, and an iminomethylenyl linkage involving the rifamycin C3 atom. By way of further example, when X is a rifamycin derivative, X can be bonded to the α linker through a cyclo linkage involving the C3 and C4 atoms. By way of further example, when X is a rifamycin derivative, X can be bonded to the α linker through one of an ester linkage or an ether linkage involving O12, the oxygen atom pendent from the C4 atom of the rifamycin fused ring system. Methods of functionalization of the rifamycin C3, C4, and C11 atoms, and atoms pendant therefrom, are established and known in the art.

When X is a streptovaricin derivative, it is preferred that X is bonded to the α linker through the streptovaricin fused ring system, most preferably, through at least one of the C3 atom, an atom pendant from the C3 atom, the C4 atom, and an atom pendant from the C4 atom [representing atoms that, by analogy to the three-dimensional structures of RNAP-rifamycin complexes (see Campbell, et al. (2001) Cell 104, 901-912; Artsimovitch, et al. (2005) Cell 122, 351-363; Lin, W., Mandal, S., Degen, D., Liu, Y., Ebright, Y. W., Li, S., Feng, Y., Zhang, Y., Mandal, S., Jiang, Y., Liu, S., Gigliotti, M., Talaue, M., Connell, N., Das, K., Arnold, E., and Ebright, R. H. (2017) Mol. Cell 66, 169-179), are expected not to be involved in RNAP-streptovaricin interactions and thus to be able to be functionalized without loss of RNAP-streptovaricin interactions].

When X is a tolypomycin derivative, it is preferred that X is bonded to the α linker through the tolypomycin fused ring system, most preferably, through at least one of the C3 atom, an atom pendant from the C3 atom, the C4 atom, an atom pendant from the C4 atom, the C11 atom, and an atom pendant from the C11 atom [representing atoms that, by analogy to the three-dimensional structures of RNAP-rifamycin complexes (see Campbell, et al. (2001) Cell 104, 901-912; Artsimovitch, et al. (2005) Cell 122, 351-363; Lin, W., Mandal, S., Degen, D., Liu, Y., Ebright, Y. W., Li, S., Feng, Y., Zhang, Y., Mandal, S., Jiang, Y., Liu, S., Gigliotti, M., Talaue, M., Connell, N., Das, K., Arnold, E., and Ebright, R. H. (2017) Mol. Cell 66, 169-179) are expected not to be involved in RNAP-tolypomycin interactions and thus to be able to be functionalized without loss of RNAP-tolypomycin interactions].

When X is a sorangicin derivative, it is preferred that X is bonded to the α linker through the sorangicin pendant sidechain group [corresponding to atoms C37-C45 and O10-O11 in sorangicin A, and representing a group that, in the three-dimensional structure of the RNAP-sorangicin-A complex (see Campbell, et al. (2005) EMBO J. 24, 1-9), is not involved in RNAP-sorangicin interactions and thus can be functionalized without loss of RNAP-sorangicin interactions].

Moiety that Binds to the Bridge-Helix N-Terminus of a Bacterial RNA Polymerase (Y)

Y includes any moiety that binds to the bridge-helix N-terminus of a bacterial RNA polymerase.

A region located within the RNAP active-center cleft—a region that comprises amino acids 550, 552, 555, 637, 640 and 642 of the β subunit and amino acids 749, 750, 755, and 757 of the β' subunit of RNAP from Escherichia coli—is a useful target for compounds that inhibit transcription, including, by way of example, CBR hydoxamidines and pyrazoles (CBRs) and Nα-aroyl-N-aryl-phenylalanianmides (AAPs) (Artsimovitch, I., Chu, C., Lynch, A. S., and Landick, R. (2003). Science 302, 650-654; Feng, Y., Degen, D., Wang, X., Gigliotti, M., Liu, S., Zhang, Y., Das, D., Michalchuk, T., Ebright, Y. W., Talaue, M., Connell, N., and Ebright, R. H. (2015). Structure 23, 1470-1481; Bae, B., Nayak, D., Ray, A., Mustaev, A., Landick, R., and Darst, S. A. (2015). Proc. Natl. Acad. Sci. USA 112, E4178-E4187; Ebright, R. H., Ebright, Y., Mandal, S., Wilde, R., and Li, S.

Figure 3B:
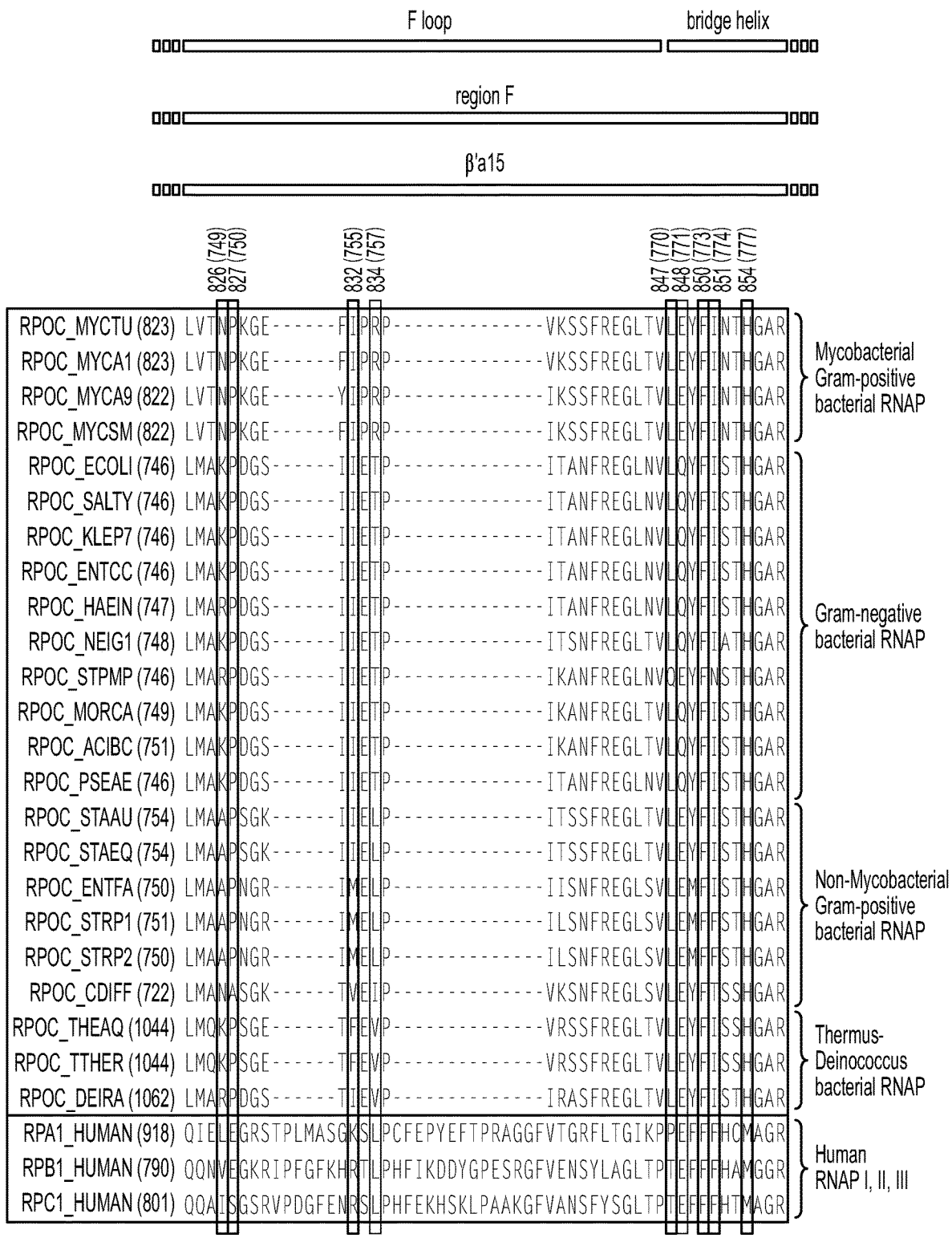

(2015) WO2015/120320; Lin, W., Mandal, S., Degen, D., Liu, Y., Ebright, Y. W., Li, S., Feng, Y., Zhang, Y., Mandal, S., Jiang, Y., Liu, S., Gigliotti, M., Talaue, M., Connell, N., Das, K., Arnold, E., and Ebright, R. H. (2017) *Mol. Cell* 66, 169-179; FIGS. 3, 4). This region is referred to herein as the "bridge-helix N-terminus target," reflecting the fact that it is includes residues of a structural element of RNAP referred to as the "bridge-helix N-terminus."

The bridge-helix N-terminus target includes residues that are invariant or nearly invariant in RNAP from Gram-negative bacterial species, but that are radically different in RNAP from eukaryotic species (Feng, Y., Degen, D., Wang, X., Gigliotti, M., Liu, S., Zhang, Y., Das, D., Michalchuk, T., Ebright, Y. W., Talaue, M., Connell, N., and Ebright, R. H. (2015). *Structure* 23, 1470-1481; Lin, W., Mandal, S., Degen, D., Liu, Y., Ebright, Y. W., Li, S., Feng, Y., Zhang, Y., Mandal, S., Jiang, Y., Liu, S., Gigliotti, M., Talaue, M., Connell, N., Das, K., Arnold, E., and Ebright, R. H. (2017) *Mol. Cell* 66, 169-179; FIG. 3).

The bridge-helix N-terminus target also includes residues that are invariant or nearly invariant in RNAP from Mycobacterial Gram-positive bacterial species, but that are radically different in RNAP from eukaryotic species (Feng, Y., Degen, D., Wang, X., Gigliotti, M., Liu, S., Zhang, Y., Das, D., Michalchuk, T., Ebright, Y. W., Talaue, M., Connell, N., and Ebright, R. H. (2015). *Structure* 23, 1470-1481; Lin, W., Mandal, S., Degen, D., Liu, Y., Ebright, Y. W., Li, S., Feng, Y., Zhang, Y., Mandal, S., Jiang, Y., Liu, S., Gigliotti, M., Talaue, M., Connell, N., Das, K., Arnold, E., and Ebright, R. H. (2017) *Mol. Cell* 66, 169-179; FIG. 3).

The bridge-helix N-terminus target also includes residues that are invariant or nearly invariant in RNAP from non-Mycobacterial Gram-positive bacterial species, but that are radically different in RNAP from eukaryotic species (Feng, Y., Degen, D., Wang, X., Gigliotti, M., Liu, S., Zhang, Y., Das, D., Michalchuk, T., Ebright, Y. W., Talaue, M., Connell, N., and Ebright, R. H. (2015). *Structure* 23, 1470-1481; Lin, W., Mandal, S., Degen, D., Liu, Y., Ebright, Y. W., Li, S., Feng, Y., Zhang, Y., Mandal, S., Jiang, Y., Liu, S., Gigliotti, M., Talaue, M., Connell, N., Das, K., Arnold, E., and Ebright, R. H. (2017) *Mol. Cell* 66, 169-179; FIG. 3).

The bridge-helix N-terminus target comprises a pocket overlapping the bridge-helix N-terminus (Feng, Y., Degen, D., Wang, X., Gigliotti, M., Liu, S., Zhang, Y., Das, D., Michalchuk, T., Ebright, Y. W., Talaue, M., Connell, N., and Ebright, R. H. (2015). *Structure* 23, 1470-1481; Lin, W., Mandal, S., Degen, D., Liu, Y., Ebright, Y. W., Li, S., Feng, Y., Zhang, Y., Mandal, S., Jiang, Y., Liu, S., Gigliotti, M., Talaue, M., Connell, N., Das, K., Arnold, E., and Ebright, R. H. (2017) *Mol. Cell* 66, 169-179; FIG. 4). A compound that binds to the bridge-helix N-terminus target of a bacterial RNAP can block bacterial RNA synthesis (e.g., interfering with bridge-helix conformational dynamics required for RNA synthesis), can inhibit bacterial gene expression, and can inhibit bacterial growth.

The bridge-helix N-terminus target in RNAP from *Escherichia coli* is similar in amino acid sequence in RNAP from most or all other Gram-negative bacterial species (Feng, Y., Degen, D., Wang, X., Gigliotti, M., Liu, S., Zhang, Y., Das, D., Michalchuk, T., Ebright, Y. W., Talaue, M., Connell, N., and Ebright, R. H. (2015). *Structure* 23, 1470-1481; Lin, W., Mandal, S., Degen, D., Liu, Y., Ebright, Y. W., Li, S., Feng, Y., Zhang, Y., Mandal, S., Jiang, Y., Liu, S., Gigliotti, M., Talaue, M., Connell, N., Das, K., Arnold, E., and Ebright, R. H. (2017) *Mol. Cell* 66, 169-179; FIG. 3). For example, amino acid residues 550, 552, 555, 637, 640, and 642 of the β subunit and amino acids 749, 750, 755, and 757 of the β' subunit of RNAP from *Escherichia coli* exhibit high similarity to corresponding amino acid residues of the β and β' subunits of RNAP from other Gram-negative bacterial species (FIG. 3). Thus, a molecule that binds to the bridge-helix N-terminus target of, and inhibits RNA synthesis by, RNAP from *Escherichia coli* also is likely to bind to the bridge-helix N-terminus target of, and inhibit RNA synthesis by, RNAP from other Gram-negative bacterial species.

The bridge-helix N-terminus target in RNAP from *Mycobacterium tuberculosis* is similar in amino acid sequence in RNAP from most or all other Mycobacterial species (Lin, W., Mandal, S., Degen, D., Liu, Y., Ebright, Y. W., Li, S., Feng, Y., Zhang, Y., Mandal, S., Jiang, Y., Liu, S., Gigliotti, M., Talaue, M., Connell, N., Das, K., Arnold, E., and Ebright, R. H. (2017) *Mol. Cell* 66, 169-179; FIG. 3). For example, amino acid residues 475, 477, 480, 562, 566, and 568 of the β subunit and amino acids 826, 827, 832, 834, 847, 848, 850, 851, and 854 of the β' subunit of RNAP from *Mycobacterium tuberculosis* exhibit high similarity to corresponding amino acid residues of the β and β' subunits of RNAP from other Mycobacterial bacterial species (FIG. 3). Thus, the a molecule that binds to the bridge-helix N-terminus target of, and inhibits RNA synthesis by, RNAP from *Mycobacterium tuberculosis* also is likely to bind to the bridge-helix N-terminus target of, and inhibit RNA synthesis by, RNAP from other Mycobacterial bacterial species.

The bridge-helix N-terminus target in RNAP from *Staphylococcus aureus* is similar in amino acid sequence in RNAP from most or all other non-Mycobacterial Gram-positive bacterial species (Lin, W., Mandal, S., Degen, D., Liu, Y., Ebright, Y. W., Li, S., Feng, Y., Zhang, Y., Mandal, S., Jiang, Y., Liu, S., Gigliotti, M., Talaue, M., Connell, N., Das, K., Arnold, E., and Ebright, R. H. (2017) *Mol. Cell* 66, 169-179; FIG. 3). For example, amino acid residues 505.5-7, 510, 594, 597, and 599 of the β subunit and amino acids 757, 758, 763, 765, 778, 779, 781, 782, and 785 of the β' subunit of RNAP from *Staphylococcus aureus* exhibit high similarity to corresponding amino acid residues of the β and β' subunits of RNAP from other non-Mycobacterial Gram-positive bacterial species (FIG. 3). Thus, the a molecule that binds to the bridge-helix N-terminus target of, and inhibits RNA synthesis by, RNAP from *Staphylococcus aureus* also is likely to bind to the bridge-helix N-terminus target of, and inhibit RNA synthesis by, RNAP from other non-Mycobacterial Gram-positive bacterial species.

In contrast, the bridge-helix N-terminus target differs radically in amino acid sequence between bacterial RNAP and eukaryotic RNAP, including human RNAP I, human RNAP II, and human RNAP III (FIG. 1). This allows for the identification of molecules that bind, in a bridge-helixpN-terminus-target-dependent fashion, to a bacterial RNAP, but that do not bind, or that bind substantially less well, to a eukaryotic RNAP. This also allows for the identification of molecules that inhibit, in a bridge-helixpN-terminus-target-dependent fashion, an activity of a bacterial RNAP, but that do not inhibit, or that inhibit substantially less well, an activity of a eukaryotic RNAP. This differentiation is important, because it permits the identification of bacterial-RNAP-selective binding molecules and bacteria-selective inhibitors.

Assays that enable identification of compounds that bind to the bridge-helix N-terminus, and inhibit RNA synthesis by, a bacterial RNA polymerase are known in the art [Feng, Y., Degen, D., Wang, X., Gigliotti, M., Liu, S., Zhang, Y., Das, D., Michalchuk, T., Ebright, Y. W., Talaue, M., Connell, N., and Ebright, R. H. (2015). *Structure* 23, 1470-1481; Bae, B., Nayak, D., Ray, A., Mustaev, A., Landick, R., and Darst, S. A. (2015). *Proc. Natl. Acad. Sci. USA* 112, E4178-E4187; Ebright, R. H., Ebright, Y., Mandal, S., Wilde, R., and Li, S. (2015) WO2015/120320; Lin, W., Mandal, S., Degen, D., Liu, Y., Ebright, Y. W., Li, S., Feng, Y., Zhang, Y., Mandal, S., Jiang, Y., Liu, S., Gigliotti, M., Talaue, M., Connell, N., Das, K., Arnold, E., and Ebright, R. H. (2017) *Mol. Cell* 66, 169-179].

Compounds that bind to the bridge-helix N-terminus target of, and inhibit RNA synthesis by, a bacterial RNAP are known in the art. Such ligands include, for example, CBR hydroxamidines and CBR pyrazoles (CBRs; Li, L., Chen, X., Fan, P., Mihalic, J. and Cutler, S. (2001) WO/2001/051456; Li, L., Chen, X., Cutler, S. and Mann, J. (2001) Pyrazole antimicrobial agents. WO/2001/082930; Artsimovitch, I., Chu, C., Lynch, A. S., and Landick, R. (2003). *Science* 302, 650-654; Feng, Y., Degen, D., Wang, X., Gigliotti, M., Liu, S., Zhang, Y., Das, D., Michalchuk, T., Ebright, Y. W., Talaue, M., Connell, N., and Ebright, R. H. (2015). *Structure* 23, 1470-1481; Bae, B., Nayak, D., Ray, A., Mustaev, A., Landick, R., and Darst, S. A. (2015). *Proc. Natl. Acad. Sci. USA* 112, E4178-E4187) and Nα-aroyl-N-aryl-phenylalanianmides (AAPs; Ebright, R. H., Ebright, Y., Mandal, S., Wilde, R., and Li, S. (2015) WO2015/120320; Lin, W., Mandal, S., Degen, D., Liu, Y., Ebright, Y. W., Li, S., Feng, Y., Zhang, Y., Mandal, S., Jiang, Y., Liu, S., Gigliotti, M., Talaue, M., Connell, N., Das, K., Arnold, E., and Ebright, R. H. (2017) *Mol. Cell* 66, 169-179). The references cited above are incorporated herein in their entirety.

CBR hydroxamidines and CBR pyrazoles (CBRs) are classes of antibacterial agents known in the art that function by inhibiting RNAP through binding to the bridge-helix N-terminus target (Li, L., Chen, X., Fan, P., Mihalic, J. and Cutler, S. (2001) WO/2001/051456; Li, L., Chen, X., Cutler, S. and Mann, J. (2001) Pyrazole antimicrobial agents. WO/2001/082930; Artsimovitch, I., Chu, C., Lynch, A. S., and Landick, R. (2003). *Science* 302, 650-654; Feng, Y., Degen, D., Wang, X., Gigliotti, M., Liu, S., Zhang, Y., Das, D., Michalchuk, T., Ebright, Y. W., Talaue, M., Connell, N., and Ebright, R. H. (2015). *Structure* 23, 1470-1481; Bae, B., Nayak, D., Ray, A., Mustaev, A., Landick, R., and Darst, S. A. (2015). *Proc. Natl. Acad. Sci. USA* 112, E4178-E4187). CBRs, for example, CBR703, can exhibit potent RNAP-inhibitory activity against RNAP from Gram-negative bacteria and potent antibacterial activity against Gram-negative bacterial species.

Nα-aroyl-N-aryl-phenylalanianmides (AAPs) are another class of antibacterial agents known in the art that function by inhibiting RNAP through binding to the bridge-helix N-terminus target (Ebright, R. H., Ebright, Y., Mandal, S., Wilde, R., and Li, S. (2015) WO2015/120320; Lin, W., Mandal, S., Degen, D., Liu, Y., Ebright, Y. W., Li, S., Feng, Y., Zhang, Y., Mandal, S., Jiang, Y., Liu, S., Gigliotti, M., Talaue, M., Connell, N., Das, K., Arnold, E., and Ebright, R. H. (2017) *Mol. Cell* 66, 169-179). AAPs, for example, D-AAP-1 and IX-214, can exhibit potent RNAP-inhibitory activity against RNAP from Mycobacteria and potent antibacterial activity against Mycobacterial species.

Resistance to CBRs and AAPs arises from mutations that result in amino acid substitutions in, or immediately adjacent to the bridge-helix N-terminus target (Artsimovitch, I., Chu, C., Lynch, A. S., and Landick, R. (2003). Science 302, 650-654; Feng, Y., Degen, D., Wang, X., Gigliotti, M., Liu, S., Zhang, Y., Das, D., Michalchuk, T., Ebright, Y. W., Talaue, M., Connell, N., and Ebright, R. H. (2015). *Structure* 23, 1470-1481; Bae, B., Nayak, D., Ray, A., Mustaev, A., Landick, R., and Darst, S. A. (2015). *Proc. Natl. Acad. Sci. USA* 112, E4178-E4187; Ebright, R. H., Ebright, Y., Mandal, S., Wilde, R., and Li, S. (2015) WO2015/120320; Lin, W., Mandal, S., Degen, D., Liu, Y., Ebright, Y. W., Li, S., Feng, Y., Zhang, Y., Mandal, S., Jiang, Y., Liu, S., Gigliotti, M., Talaue, M., Connell, N., Das, K., Arnold, E., and Ebright, R. H. (2017) *Mol. Cell* 66, 169-179).

CBRs and AAPs exhibit no cross-resistance with rifamycins (Li, L., Chen, X., Fan, P., Mihalic, J. and Cutler, S. (2001) WO/2001/051456; Li, L., Chen, X., Cutler, S. and Mann, J. (2001) Pyrazole antimicrobial agents. WO/2001/082930; Artsimovitch, I., Chu, C., Lynch, A. S., and Landick, R. (2003). Science 302, 650-654; Feng, Y., Degen, D., Wang, X., Gigliotti, M., Liu, S., Zhang, Y., Das, D., Michalchuk, T., Ebright, Y. W., Talaue, M., Connell, N., and Ebright, R. H. (2015). *Structure* 23, 1470-1481; Bae, B., Nayak, D., Ray, A., Mustaev, A., Landick, R., and Darst, S. A. (2015). *Proc. Natl. Acad. Sci. USA* 112, E4178-E4187; Ebright, R. H., Ebright, Y., Mandal, S., Wilde, R., and Li, S. (2015) WO2015/120320; Lin, W., Mandal, S., Degen, D., Liu, Y., Ebright, Y. W., Li, S., Feng, Y., Zhang, Y., Mandal, S., Jiang, Y., Liu, S., Gigliotti, M., Talaue, M., Connell, N., Das, K., Arnold, E., and Ebright, R. H. (2017) *Mol. Cell* 66, 169-179).

In certain embodiments, Y is selected from a CBR or an AAP.

In one embodiment, Y is a CBR.

In one embodiment, Y is a compound described in WO/2001/051456 or WO/2001/082930.

In one embodiment, Y is an AAP.

In one embodiment, Y is a compound described in WO2015/120320.

In one embodiment, Y is a compound according to general structural formula (I), or a salt thereof:

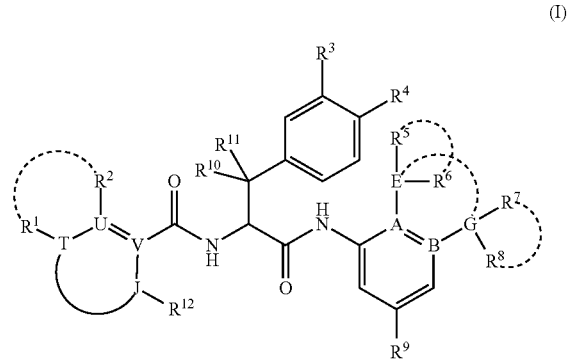

(I)

wherein:

T and U each is one of carbon and nitrogen;

V is carbon;

A and B each is one of carbon and nitrogen;

E is one of carbon (CH), nitrogen, oxygen, and sulfur;

G is absent or is one of hydrogen, halogen, carbon (CH), nitrogen, oxygen, and sulfur;

J is one of carbon and nitrogen, and J, together with T, U, V, and two additional atoms, forms a 6-membered cycle; or J is one of nitrogen, oxygen, sulfur, and selenium and J, together with T, U, V, and one additional atom, forms a 5-membered cycle;

$R^1$ and $R^2$ each independently is absent, hydrogen, hydroxy, or halogen, or is alkyl, alkoxy-substituted alkyl, amino-substituted alkyl, aryl-substituted alkyl, or alkoxy, each optionally substituted by halogen; or $R^1$ and $R^2$, together with T and U, form a cycle containing 4 to 9 atoms selected from carbon, nitrogen, oxygen, and sulfur;

$R^3$ and $R^4$ each independently is hydrogen, halogen, hydroxy, amine, amide, ester, phosphate, or O-methylphosphate; and $R^5$, $R^6$, $R^7$, and $R^8$ each independently is absent, hydrogen, or halogen, or is alkyl, alkoxy-substituted alkyl, hydroxy-substituted alkyl, amino-substituted alkyl, aryl-substituted alkyl, or alkoxy, each optionally substituted by halogen; or $R^5$ and $R^6$, together with E, form a cycle containing 3 to 9 atoms selected from carbon, nitrogen, oxygen, and sulfur, said cycle optionally substituted with halogen, amino, alkyl, hydroxy-substituted alkyl, alkoxy-substituted alkyl, amino-substituted alkyl, aryl-substituted alkyl, alkoxy, acyl, or carbamidyl, each optionally substituted by halogen; or $R^7$ and $R^8$, together with G, form a cycle containing 3 to 9 atoms selected from carbon, nitrogen, oxygen, and sulfur, said cycle optionally substituted with halogen, amino, alkyl, hydroxy-substituted alkyl, alkoxy-substituted alkyl, amino-substituted alkyl, aryl-substituted alkyl, alkoxy, acyl, or carbamidyl, each optionally substituted by halogen; or $R^6$ and $R^7$ are absent and E and G, together with A and B, form a cycle containing 4 to 9 atoms selected from carbon, nitrogen, oxygen, and sulfur, said cycle optionally substituted with halogen, amino, alkyl, hydroxy-substituted alkyl, alkoxy-substituted alkyl, amino-substituted alkyl, aryl-substituted alkyl, alkoxy, acyl, or carbamidyl, each optionally substituted by halogen;

$R^9$, is hydrogen or halogen;

$R^{10}$ and $R^{11}$ each independently is hydrogen, halogen, alkyl or alkoxy, said alkyl or alkoxy optionally substituted by halogen; or one of $R^{10}$ and $R^{11}$ is deuterium and the other is halogen, alkyl or alkoxy, said alkyl or alkoxy optionally substituted by halogen; or each of $R^{10}$ and $R^{11}$ is deuterium and $R^{12}$ is absent, hydrogen, or halogen;

or a tautomer or salt thereof.

When Y is a compound according to general structural formula (I) or a tautomer or salt thereof, it is preferred that Y is bonded to the α linker through one of A, E, R5, R6, and a cycle comprising E, R5, and R6 together with 3 to 8 atoms selected from carbon, nitrogen, oxygen, and sulfur [representing positions that in the three-dimensional structures of RNAP-AAPn complexes (see Lin, W., Mandal, S., Degen, D., Liu, Y., Ebright, Y. W., Li, S., Feng, Y., Zhang, Y., Mandal, S., Jiang, Y., Liu, S., Gigliotti, M., Talaue, M., Connell, N., Das, K., Arnold, E., and Ebright, R. H. (2017) *Mol. Cell* 66, 169-179) are not involved in crucial RNAP-AAP interactions and thus are expected to be able to be functionalized without loss of crucial RNAP-AAP interactions].

In a preferred embodiment in which Y is a compound according to general structural formula (I) or a tautomer or salt thereof, α is connected to Y through one of A, E, R5, R6, and a cycle comprising E, R5, and R6 together with 3 to 8 atoms selected from carbon, nitrogen, oxygen, and sulfur.

In one embodiment, Y is a compound of formula (X) that is a compound of formula (Ia), or a tautomer or salt thereof:

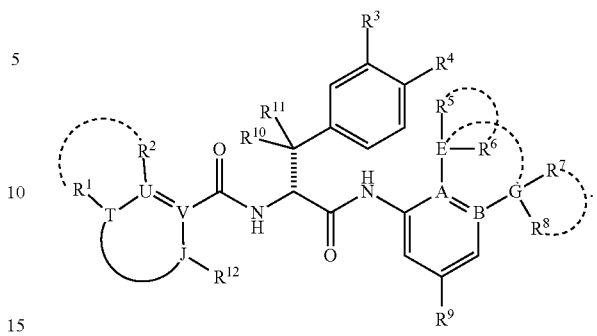

(Ia)

When Y is a compound according to general structural formula (Ia) or a tautomer or salt thereof, it is preferred that Y is bonded to the α linker through one of A, E, R5, R6, and a cycle comprising E, R5, and R6 together with 3 to 8 atoms selected from carbon, nitrogen, oxygen, and sulfur [representing positions that in the three-dimensional structures of RNAP-AAPn complexes (see Lin, W., Mandal, S., Degen, D., Liu, Y., Ebright, Y. W., Li, S., Feng, Y., Zhang, Y., Mandal, S., Jiang, Y., Liu, S., Gigliotti, M., Talaue, M., Connell, N., Das, K., Arnold, E., and Ebright, R. H. (2017) *Mol. Cell* 66, 169-179) are not involved in crucial RNAP-AAP interactions and thus are expected to be able to be functionalized without loss of crucial RNAP-AAP interactions].

In a preferred embodiment in which Y is a compound according to general structural formula (Ia) or a tautomer or salt thereof, α is connected to Y through one of A, E, R5, R6, and a cycle comprising E, R5, and R6 together with 3 to 8 atoms selected from carbon, nitrogen, oxygen, and sulfur.

In one embodiment, Y is a compound selected from the group consisting of:

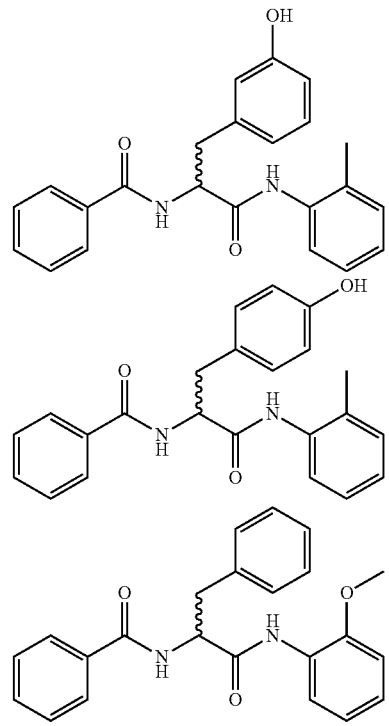

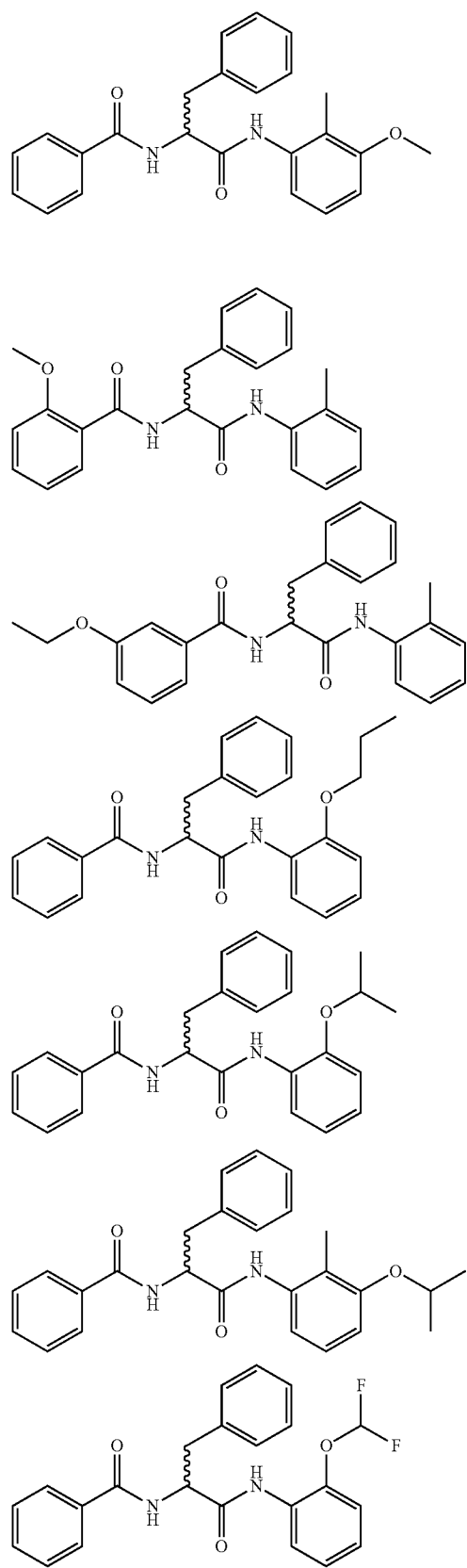
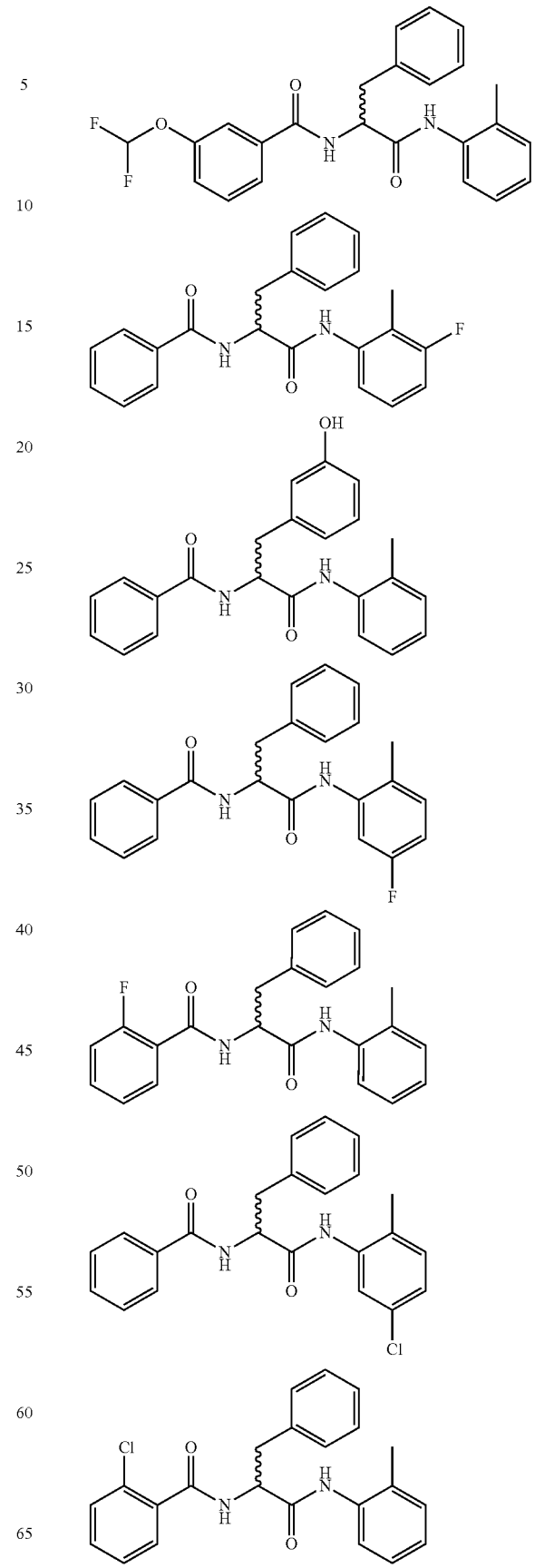

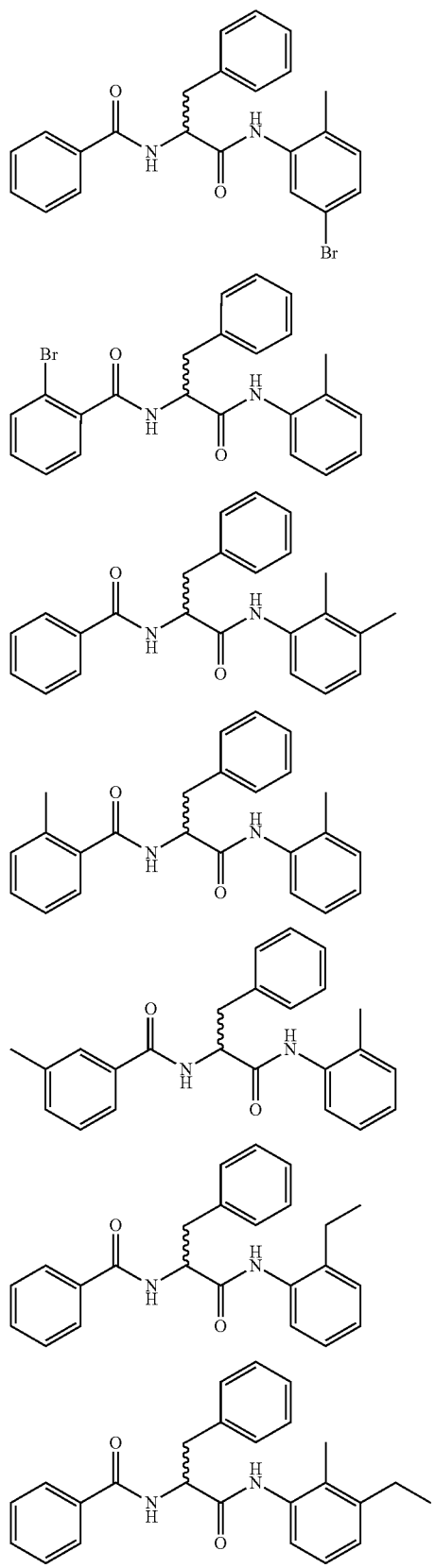
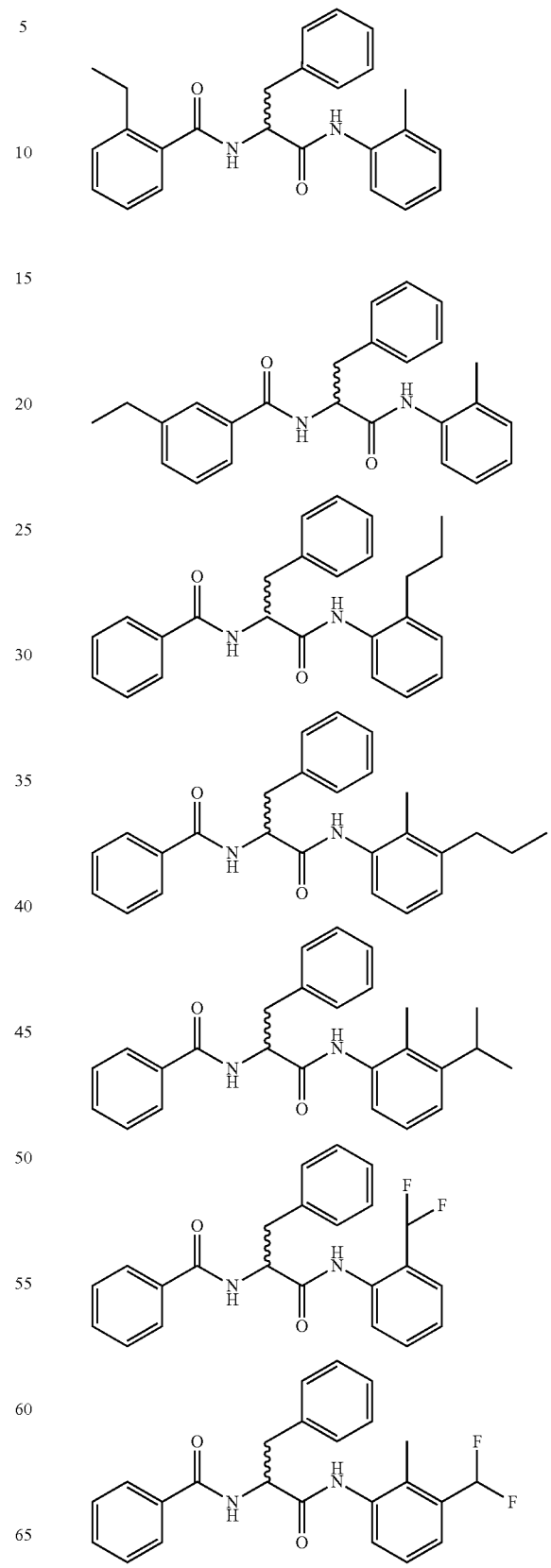

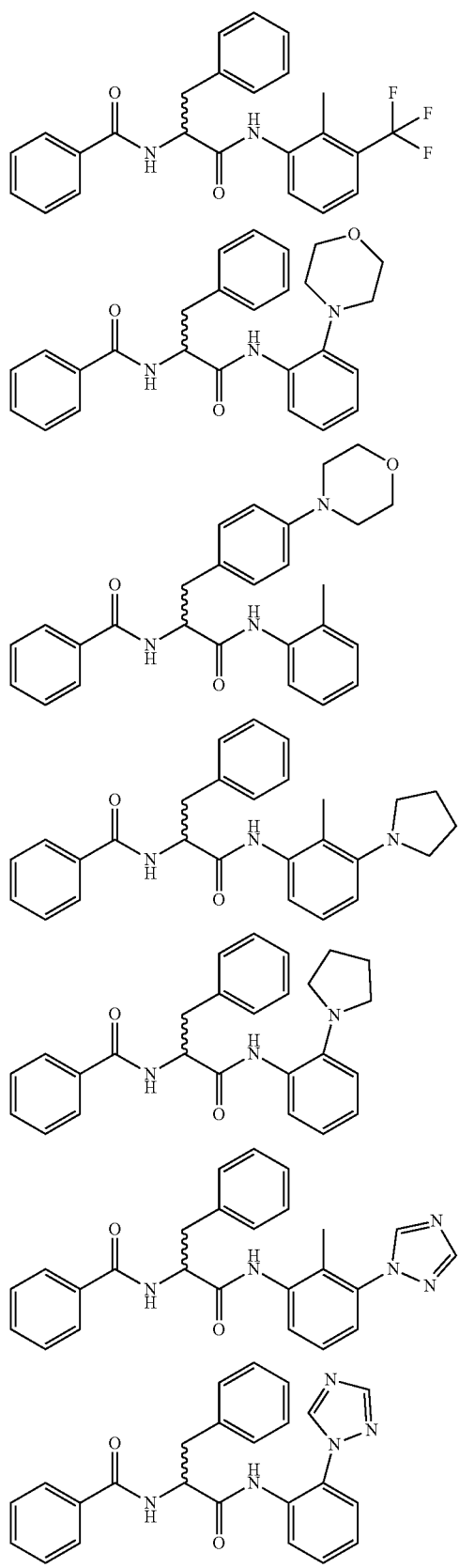
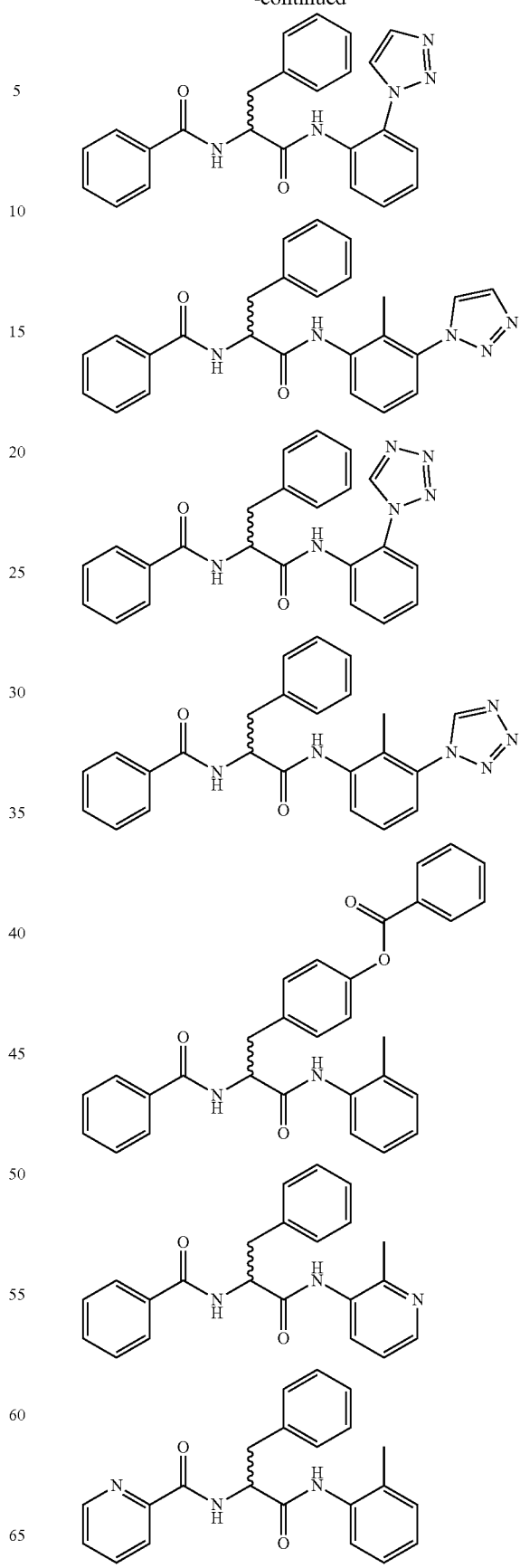

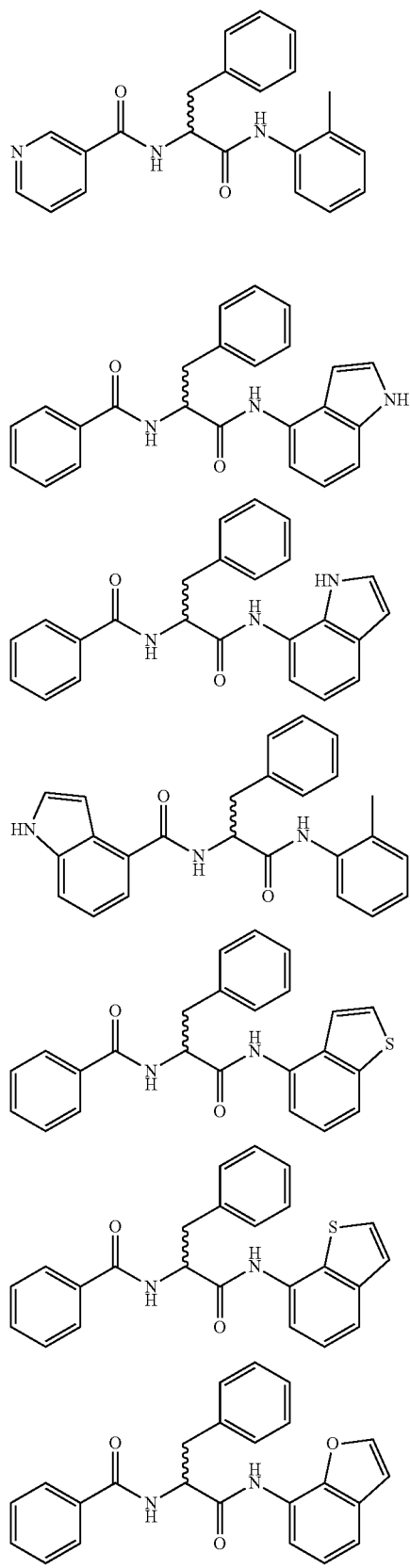
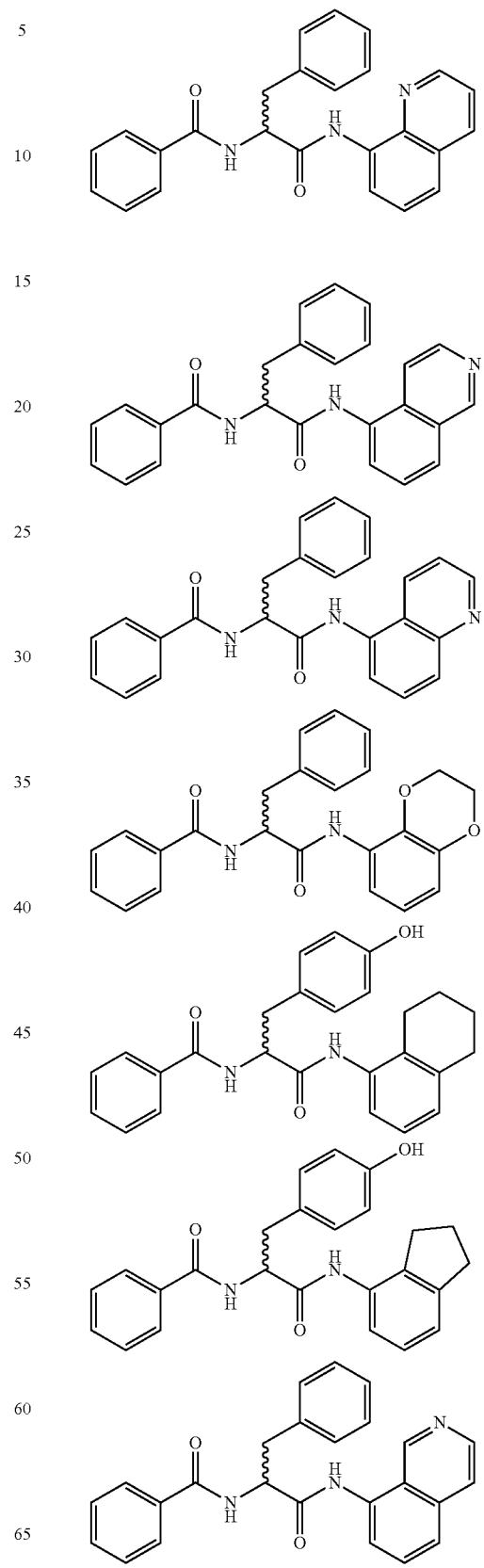

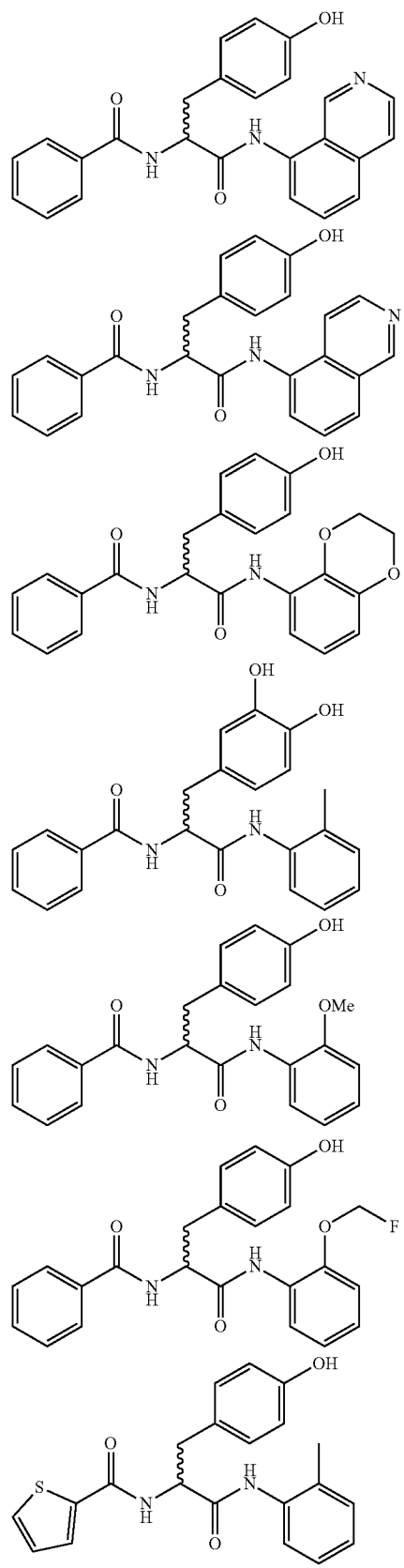
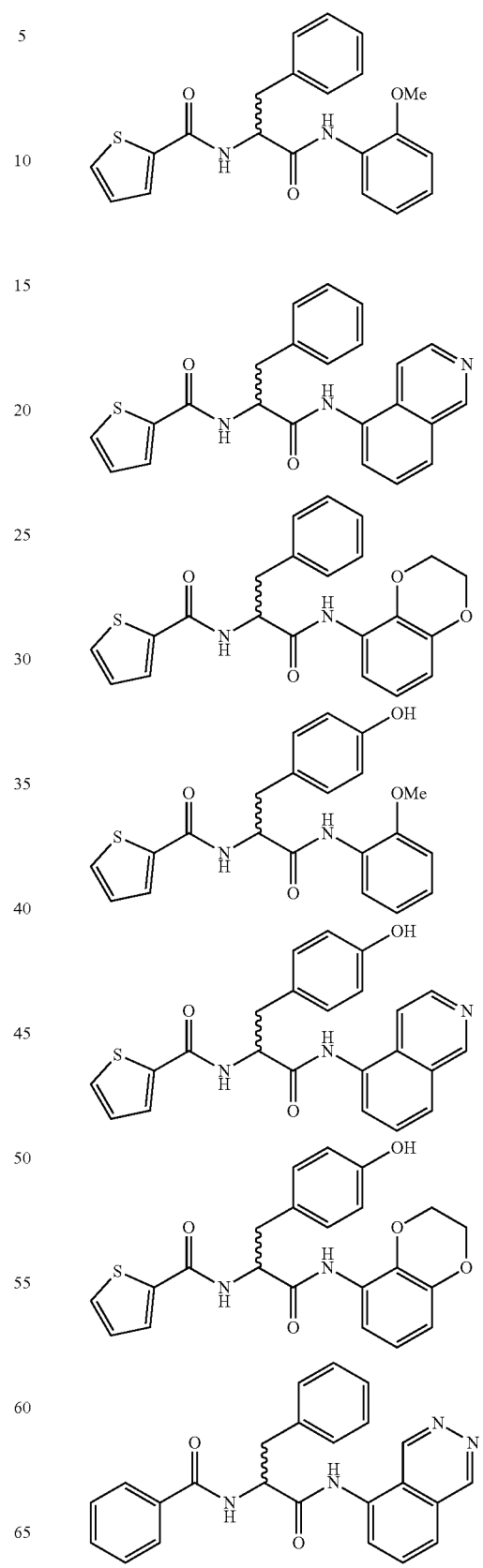

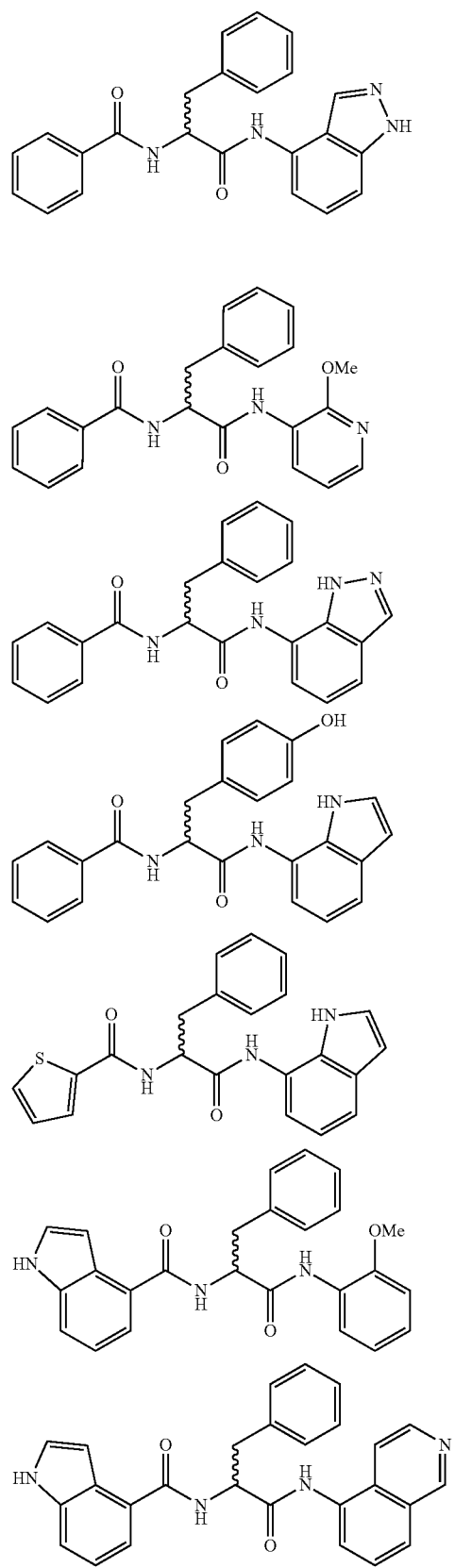
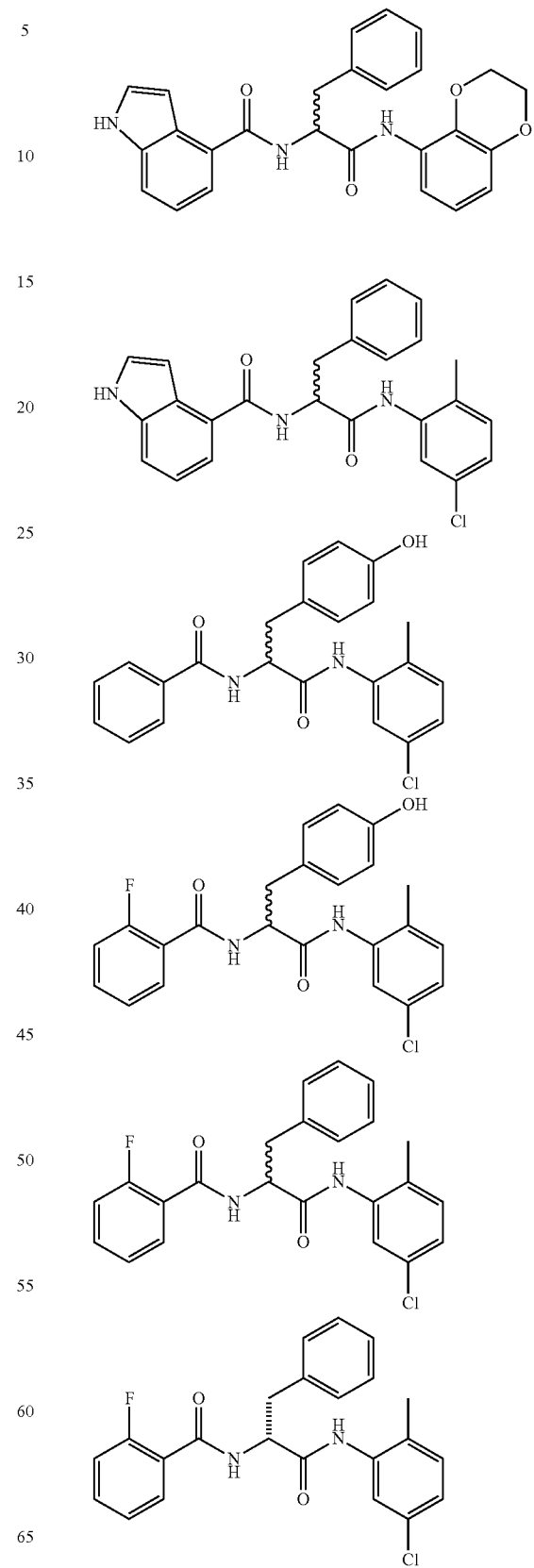

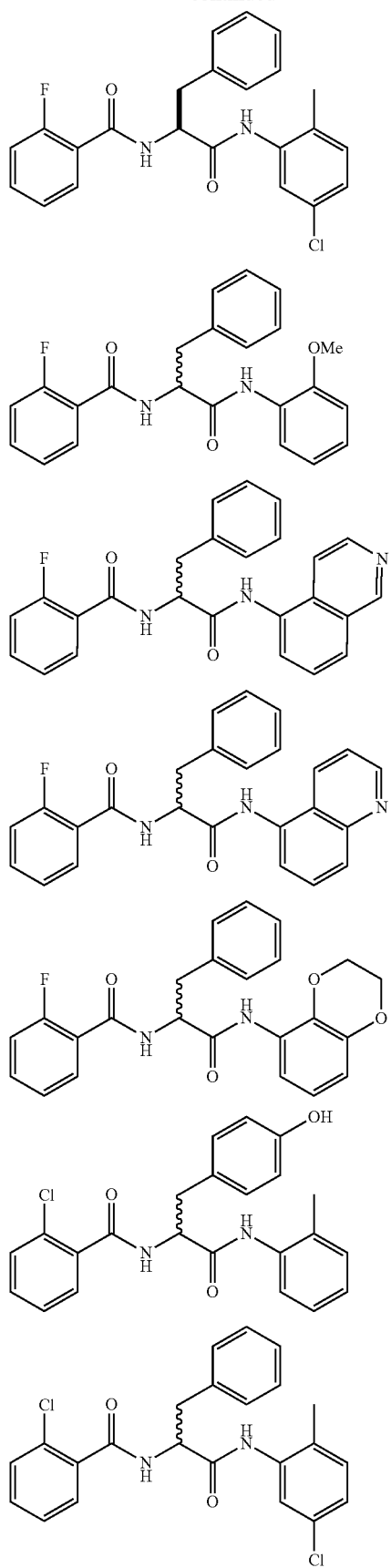
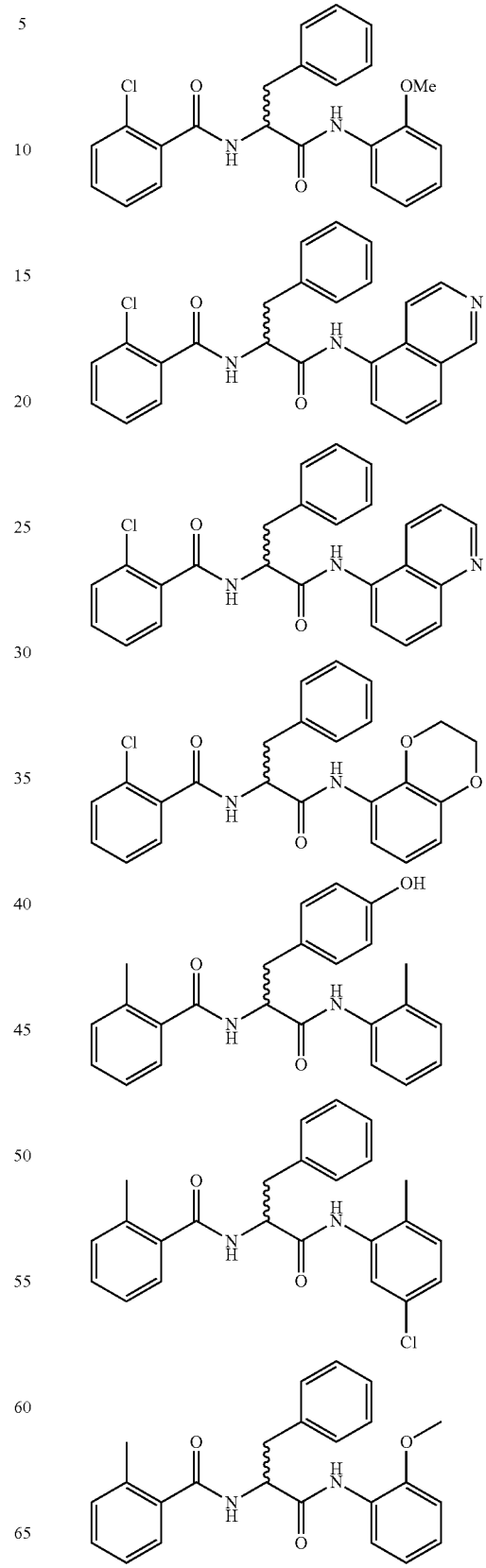

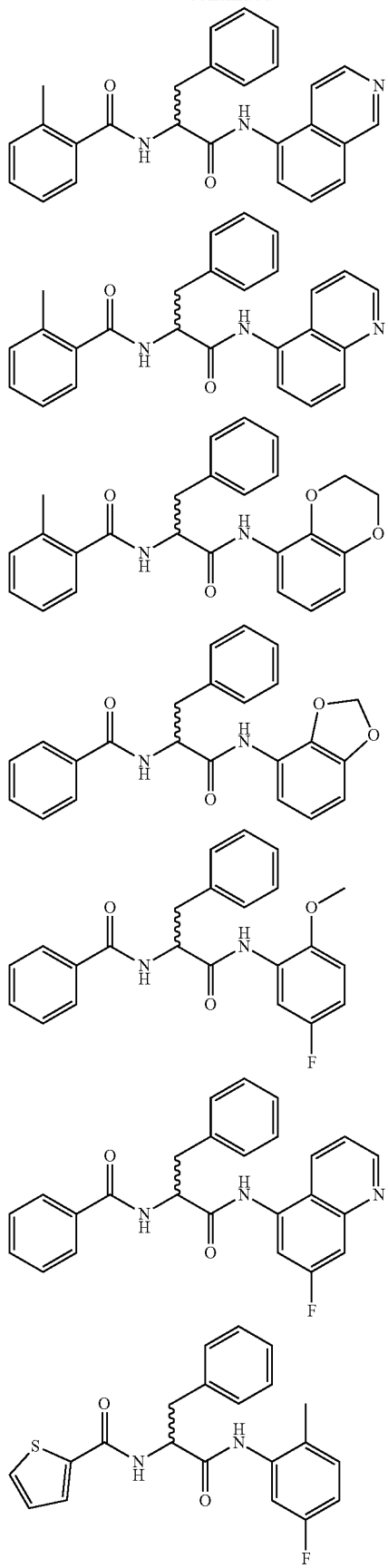
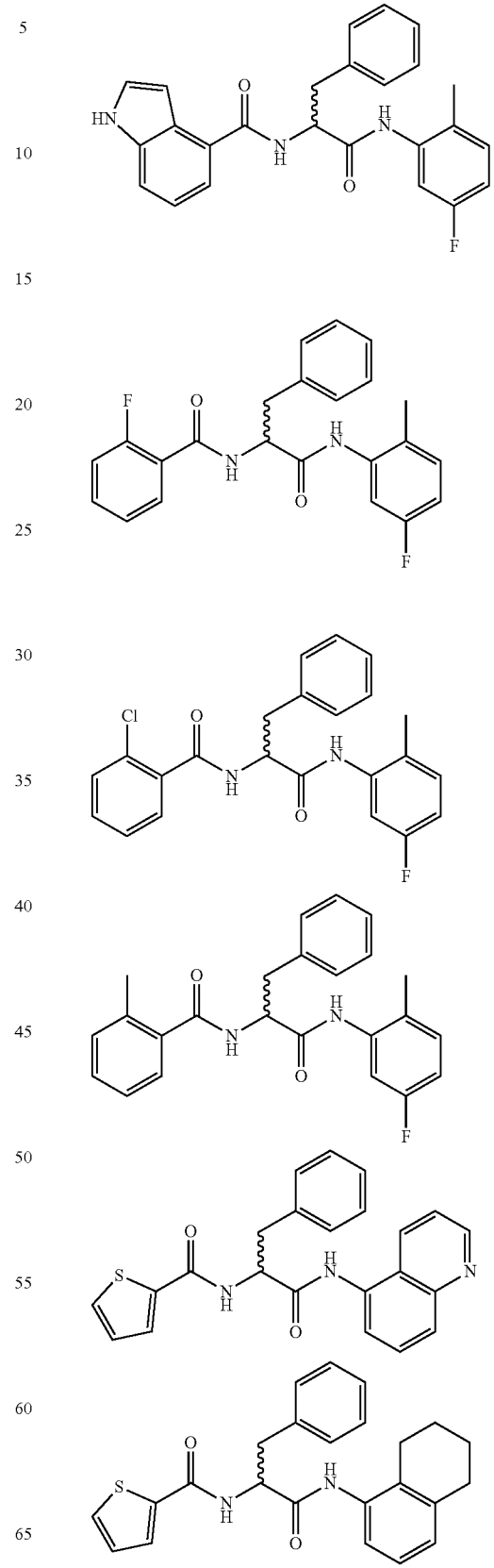

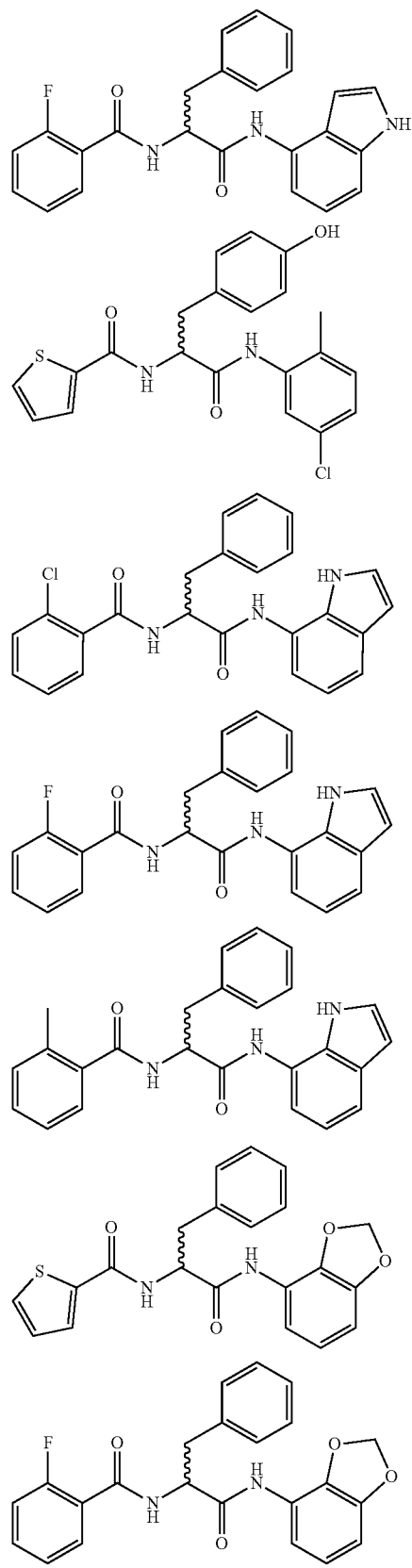
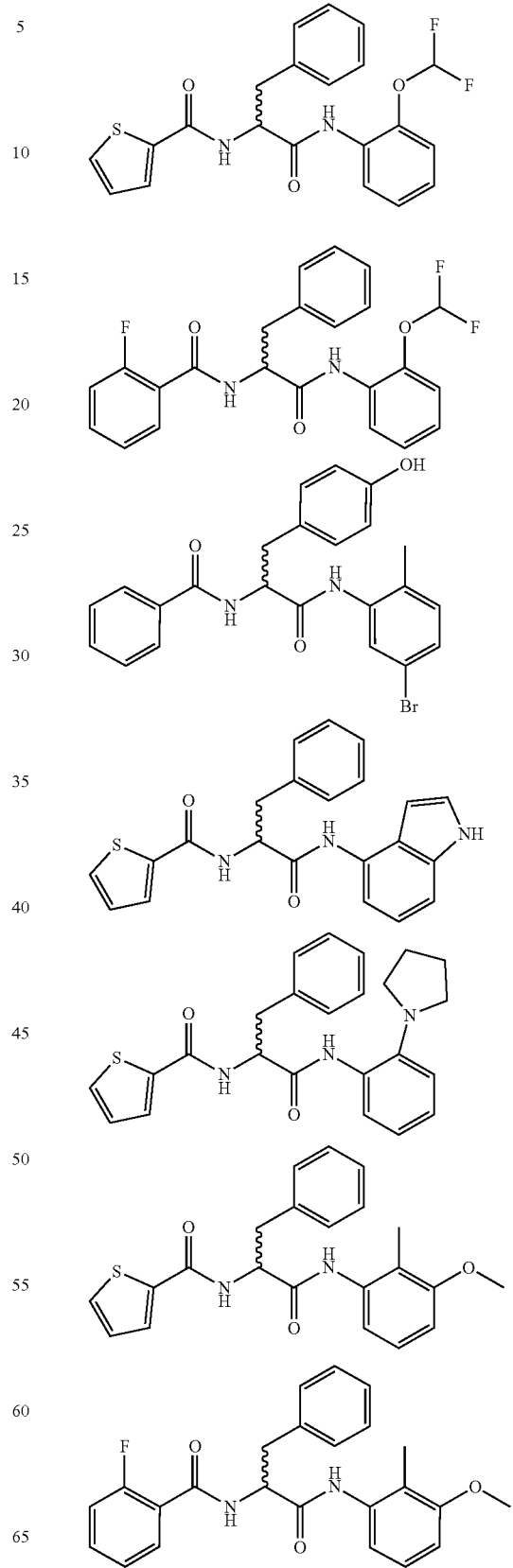

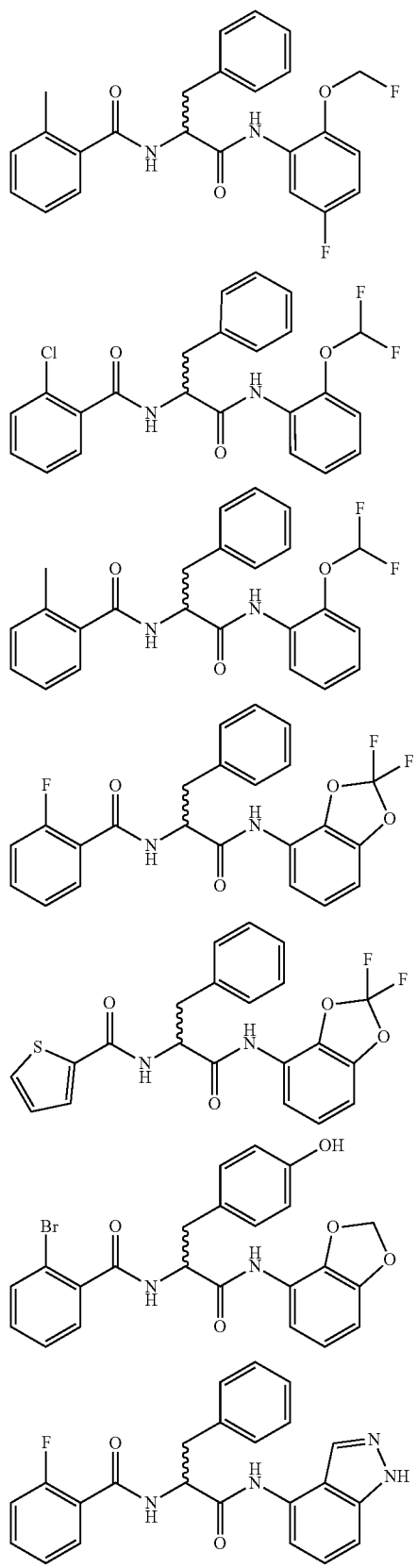
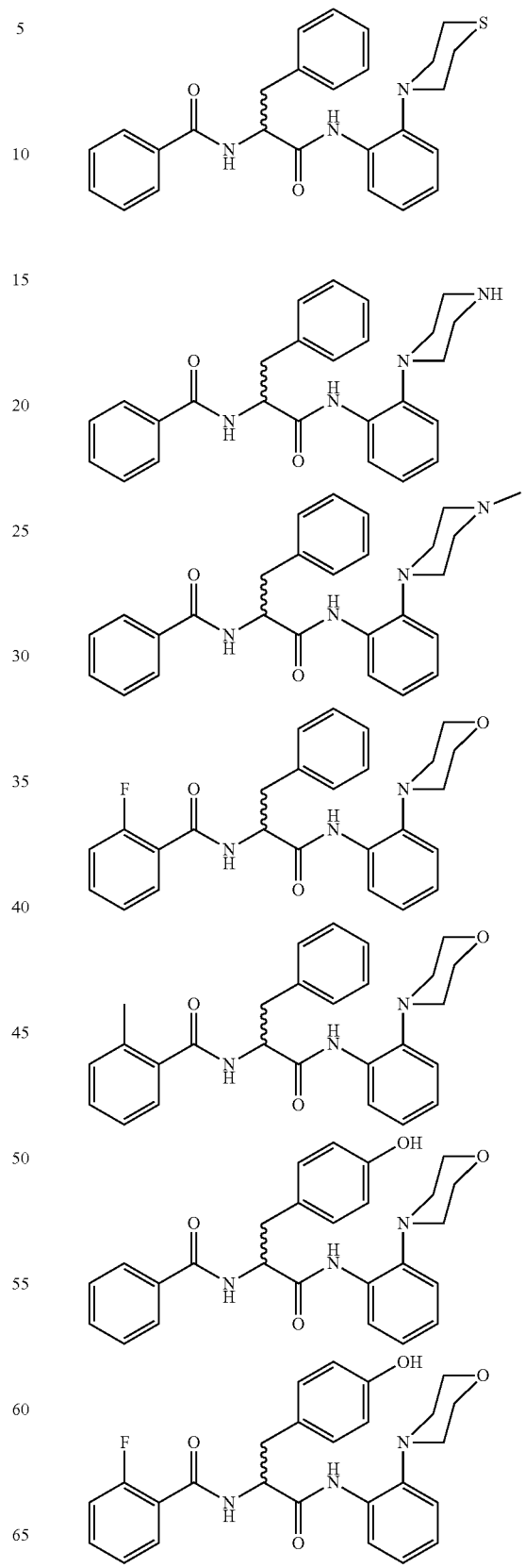

39
-continued
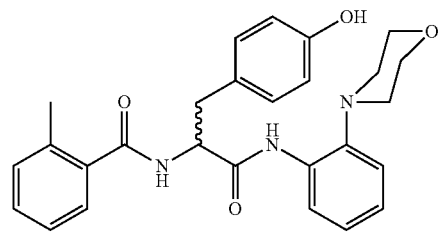
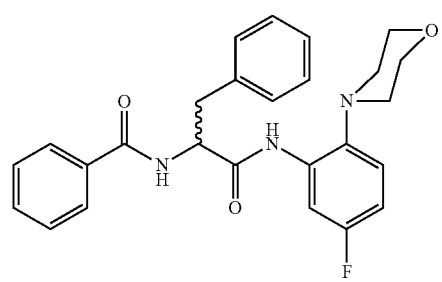
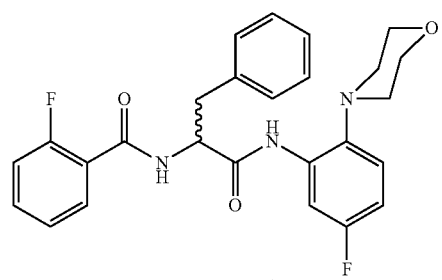
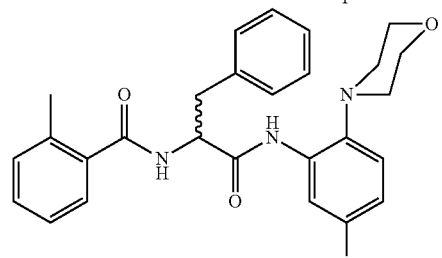
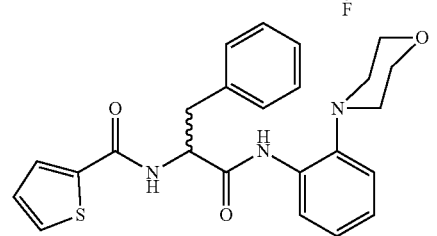
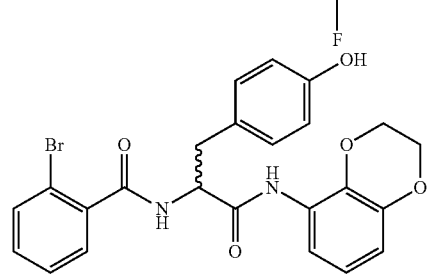
40
-continued
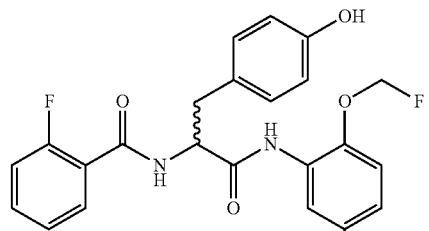
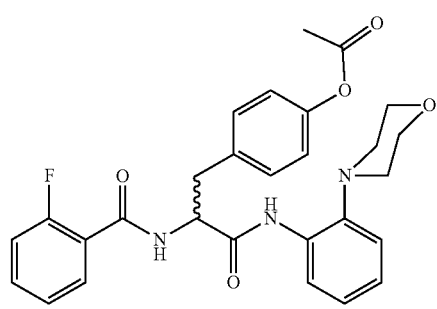
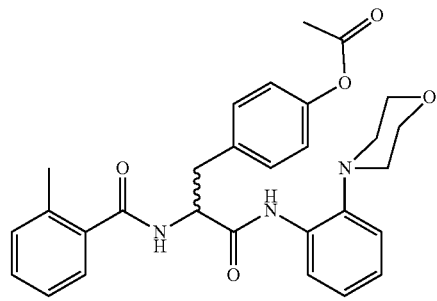
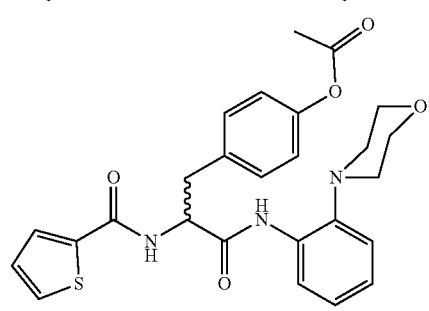
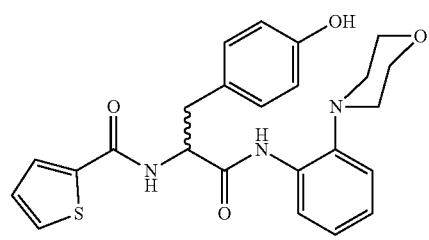
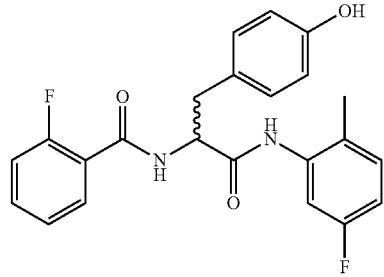

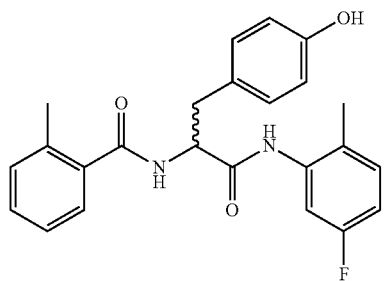
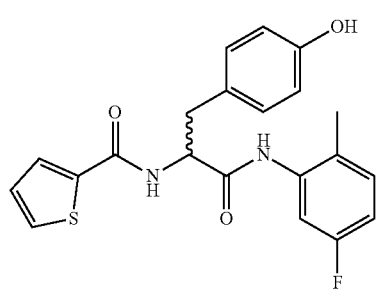
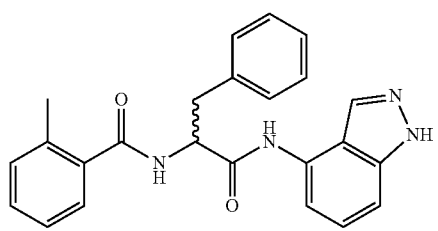
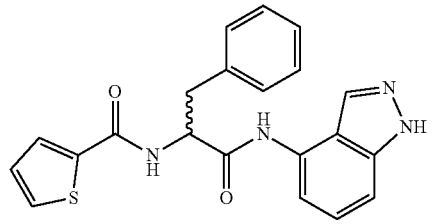
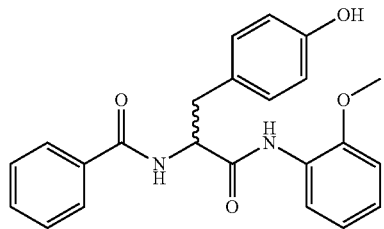
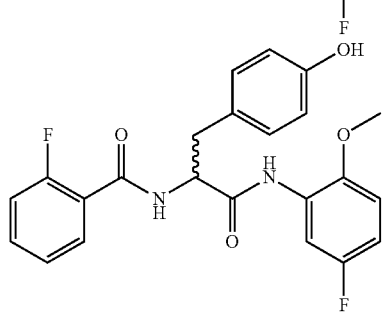
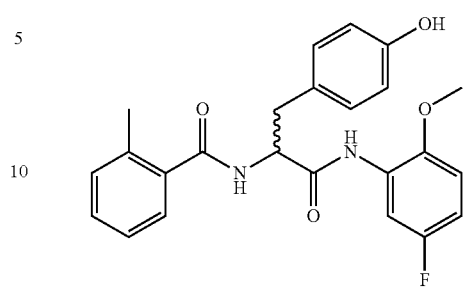
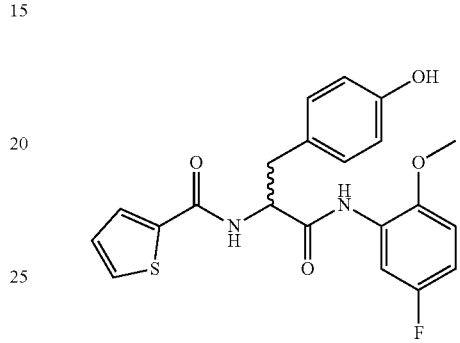
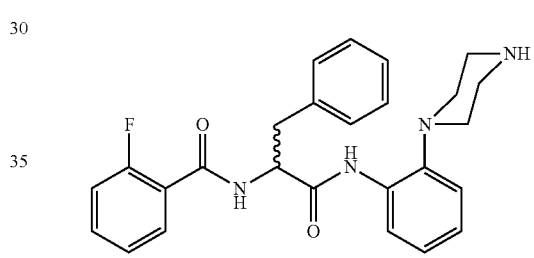
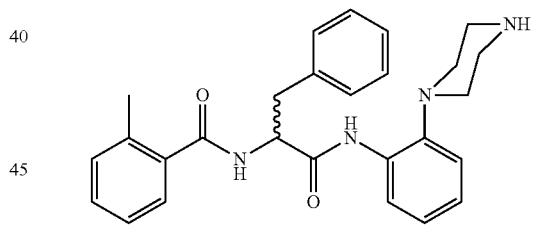
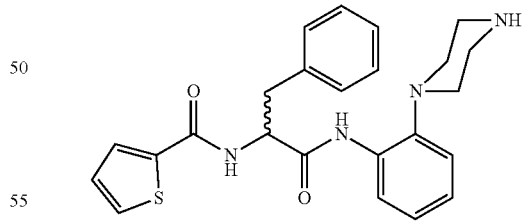
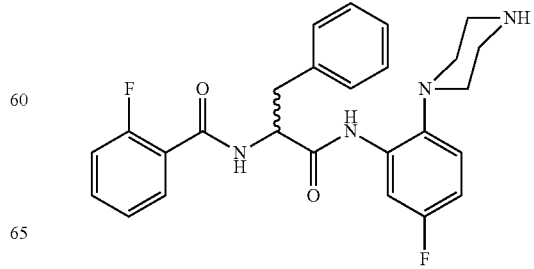

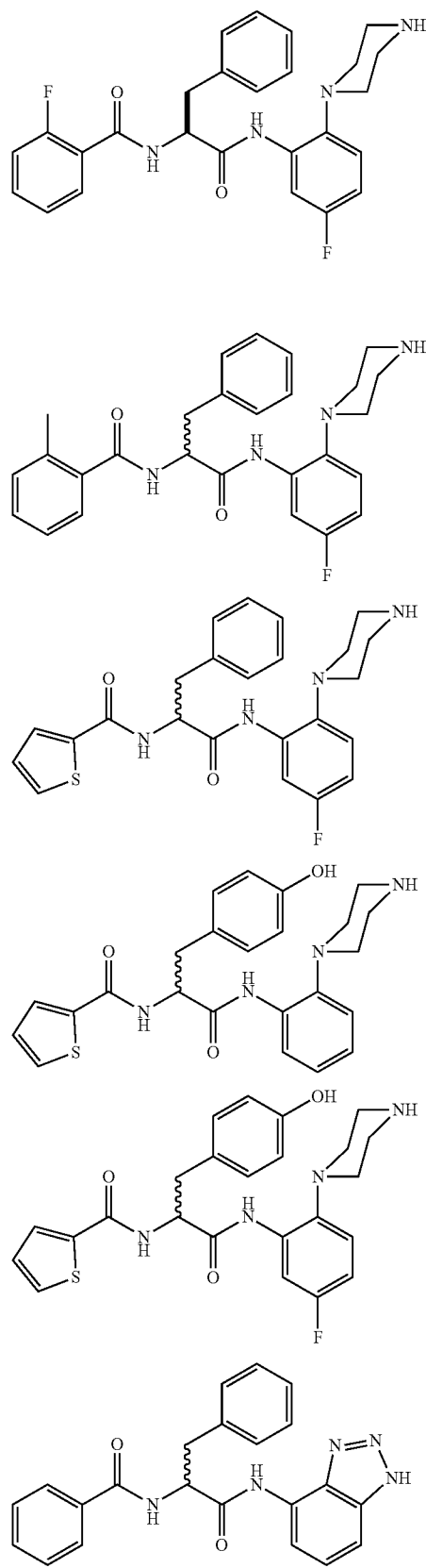
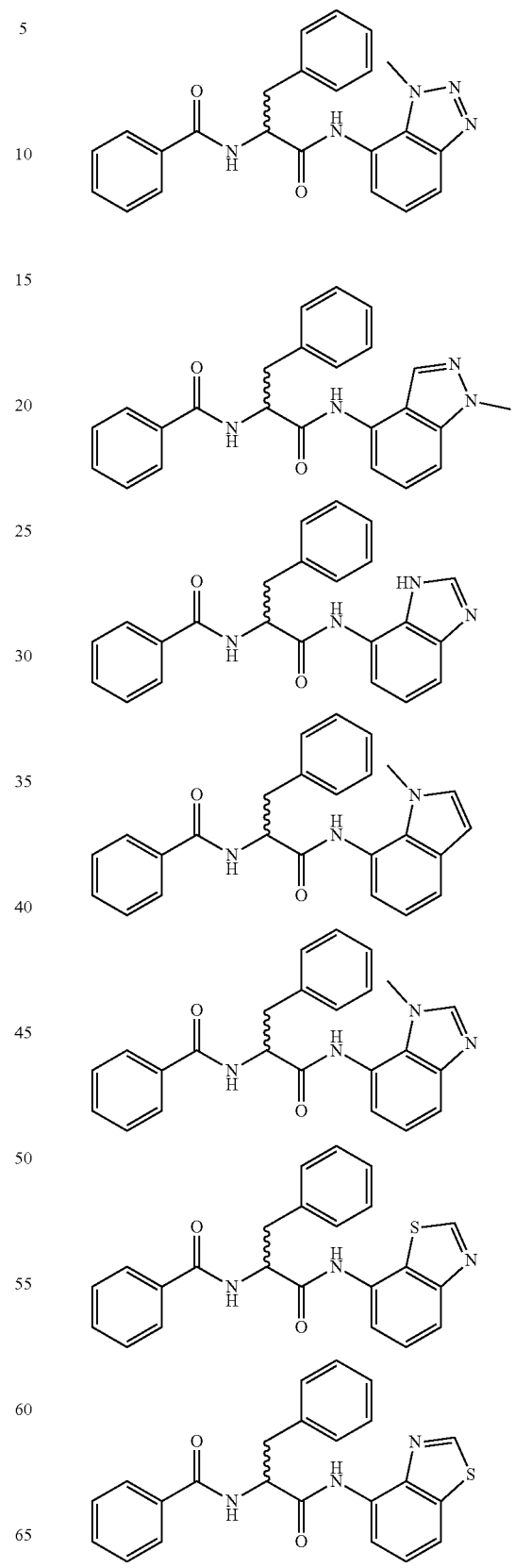

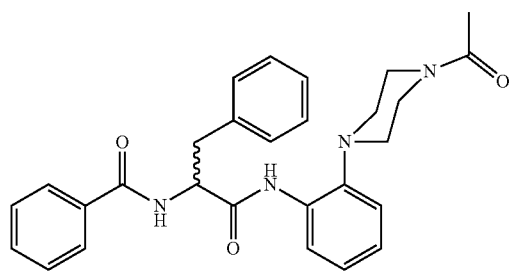
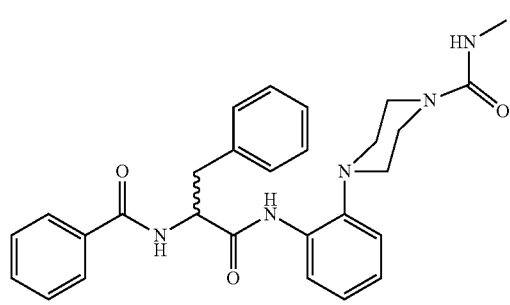
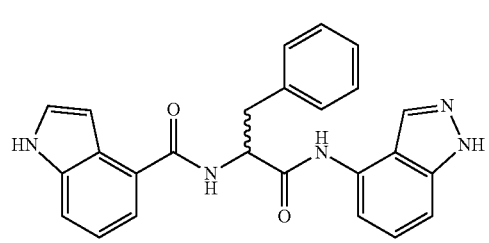
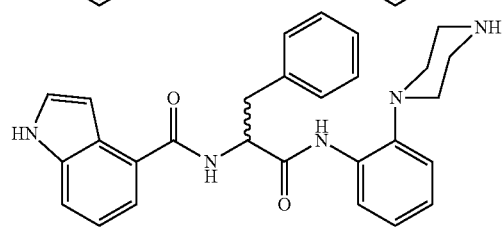
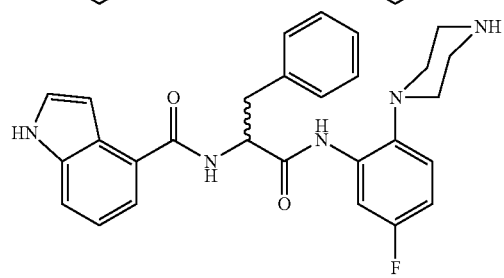
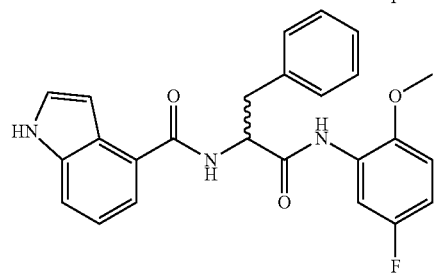
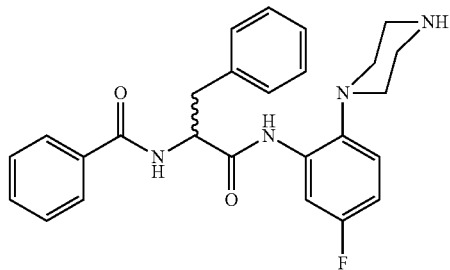
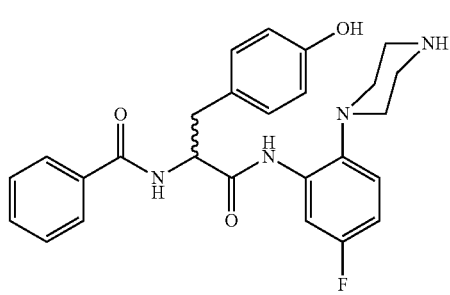
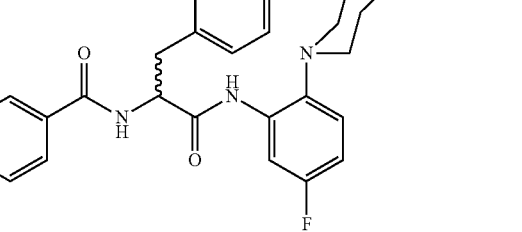
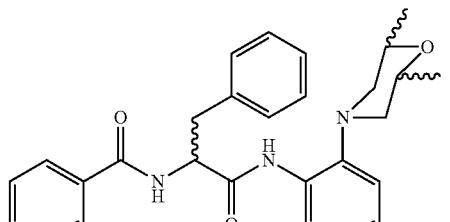
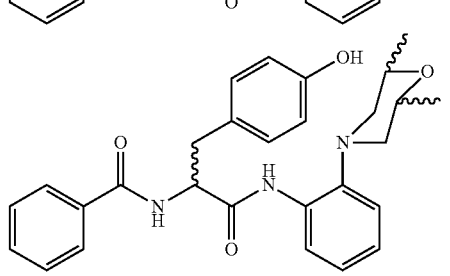
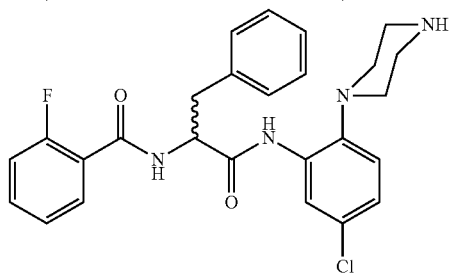

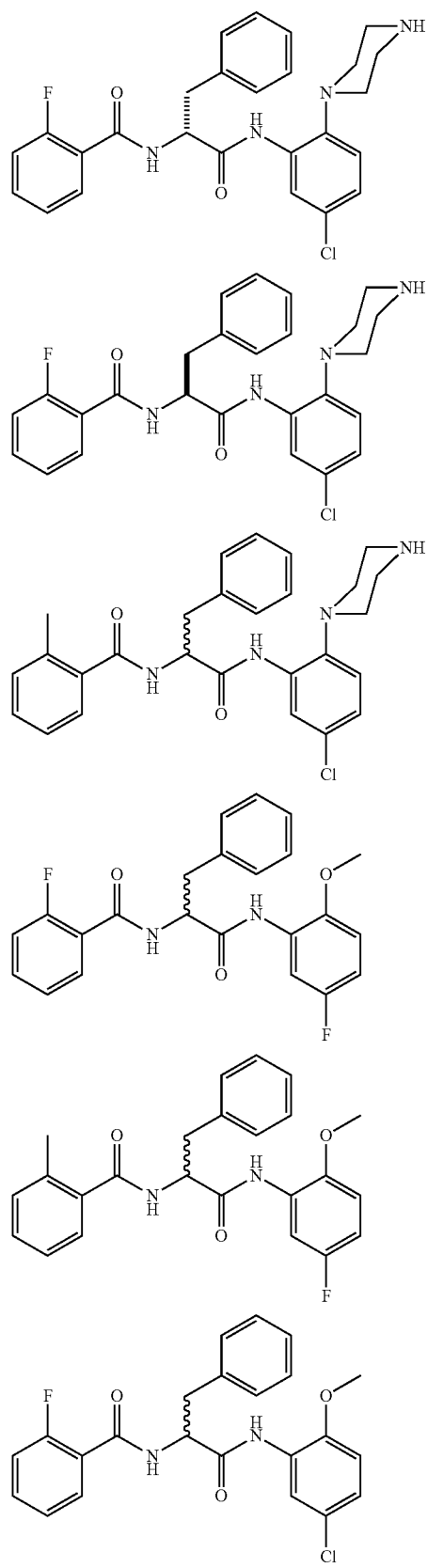
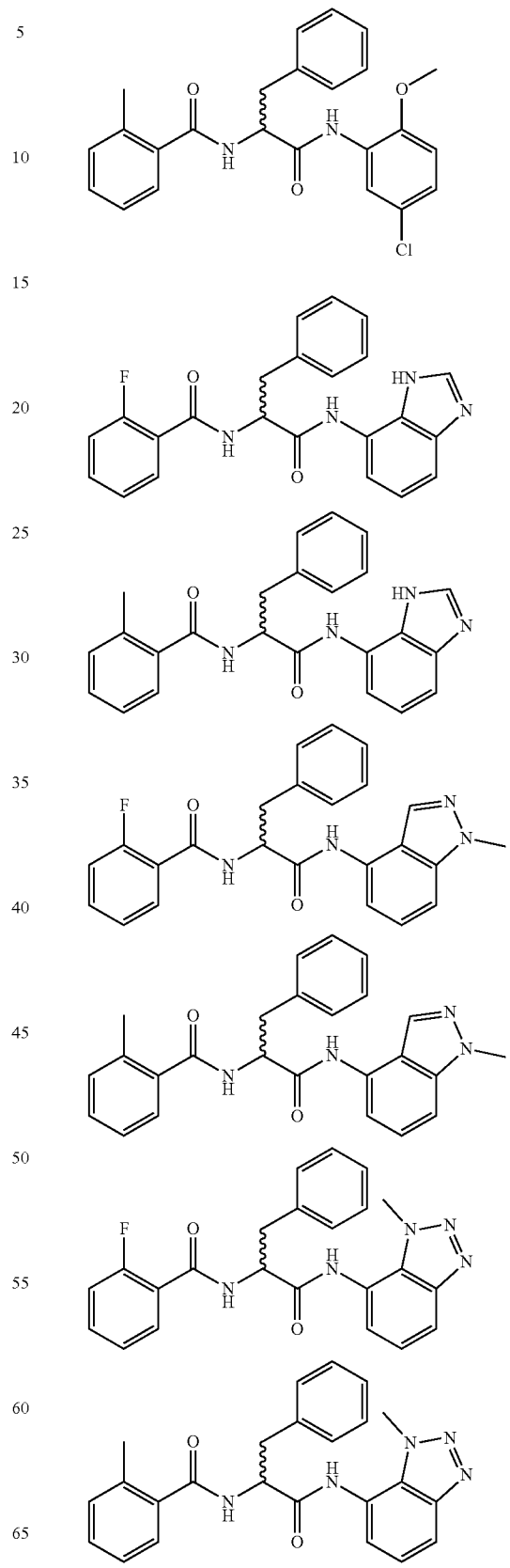

-continued

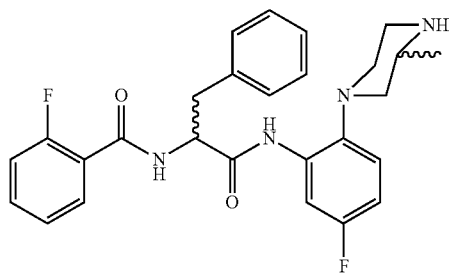
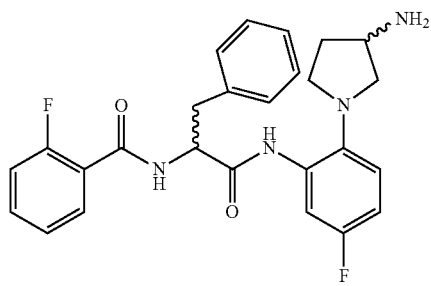
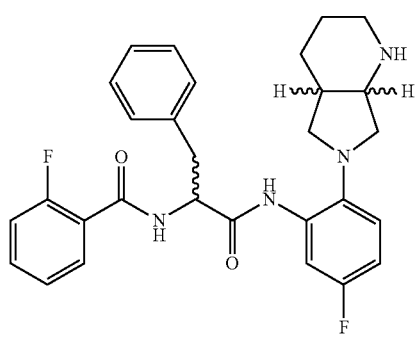
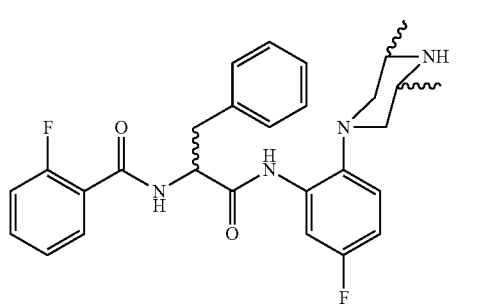
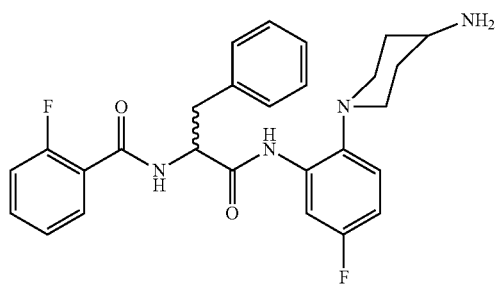

-continued

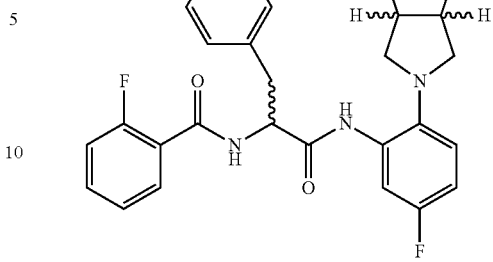
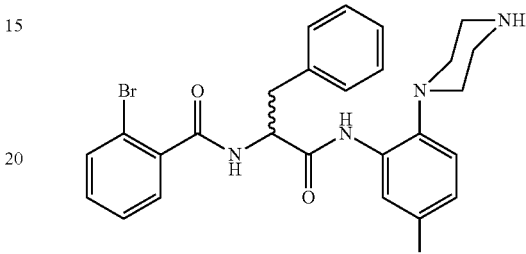
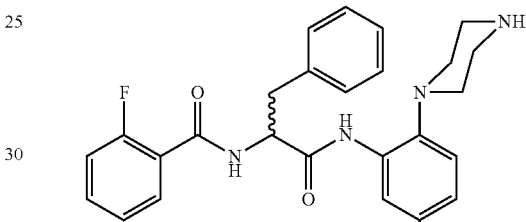

and

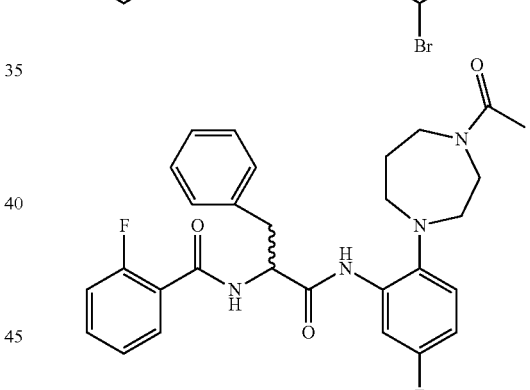

Linker (α)

In one embodiment α is a linker that links the X moiety that binds to the Rif target of a bacterial RNAP and the Y moiety that binds to the bridge-helix N-terminus target of a bacterial RNA polymerase. The linker preferably has a length of from about 0 Å to about 15 Å (representing a length suitable to connect X and Y.

The linker may contain exclusively covalent bonds. Alternatively, the linker may contain a coordinate-covalent bond.

Preferably, the linker does not substantially interfere with the individual interactions between the X moiety and the Rif target of a bacterial RNAP and between the Y moiety and the bridge-helix N-terminus target of a bacterial RNA polymerase.

Preferably, the linker does not substantially interfere with simultaneous interactions between the X moiety and the Rif target of a bacterial RNAP and between the Y moiety and the bridge-helix N-terminus target of a bacterial RNA polymerase.

Optionally, the linker makes a favorable interaction with at least one residue of RNAP located between the Rif target and the bridge-helix N-terminus target of a bacterial RNA polymerase.

In certain embodiments, α is a covalent bond.

In certain embodiments, α comprises a chain of 0 to about 12 consecutively bonded atoms.

In certain embodiments, α comprises a chain of 0 to about 10 consecutively bonded atoms.

In certain embodiments, α comprises a chain of 0 to about 8 consecutively bonded atoms.

In certain embodiments, α comprises a chain of 0 to about 6 consecutively bonded atoms.

In certain embodiments, α comprises a chain of 1 to about 12 consecutively bonded atoms.

In certain embodiments, α comprises a chain of 1 to about 10 consecutively bonded atoms.

In certain embodiments, α comprises a chain of 1 to about 8 consecutively bonded atoms.

In certain embodiments, α comprises a chain of 1 to about 6 consecutively bonded atoms.

In certain embodiments, α is a bond, and e.g., said bond connects C3 of the rifamycin fused ring system or the carboxyl carbon of the sorangicin sidechain to an atom of Y.

In certain embodiments, α is —C=N—, and e.g., said —C=N— connects C3 of the rifamycin fused ring system to an atom of Y. In certain embodiments, α is —NH— or —S—, and e.g., said —NH— or —S— connects C3 of the rifamycin fused ring system or the carboxyl of the sorangicin sidechain to an atom of Y.

In certain embodiments, α is —{CH$_2$C(O)Z}—, and e.g., said —{CH$_2$C(O)Z}— connects the oxygen atom pendant from C4 of the rifamycin fused ring system to an atom of Y; and wherein Z contains from about 0 to about 4 consecutively bonded atoms.

In certain embodiments, α is —{CH$_2$C(O)NHZ'}—; and e.g., said —{CH$_2$C(O)NHZ'}— connects the oxygen atom pendant from C4 of the rifamycin fused ring system to an atom of Y; and wherein Z' contains from about 0 to about 4 consecutively bonded atoms.

In certain embodiments, α is —(NH—Z")—, and e.g., said —(NH—Z")— connects the carboxyl carbon of the sorangicin sidechain to an atom of Y; and wherein Z" contains from about 0 to about 4 consecutively bonded atoms.

In one embodiment, the invention provides a compound selected from the group consisting of:

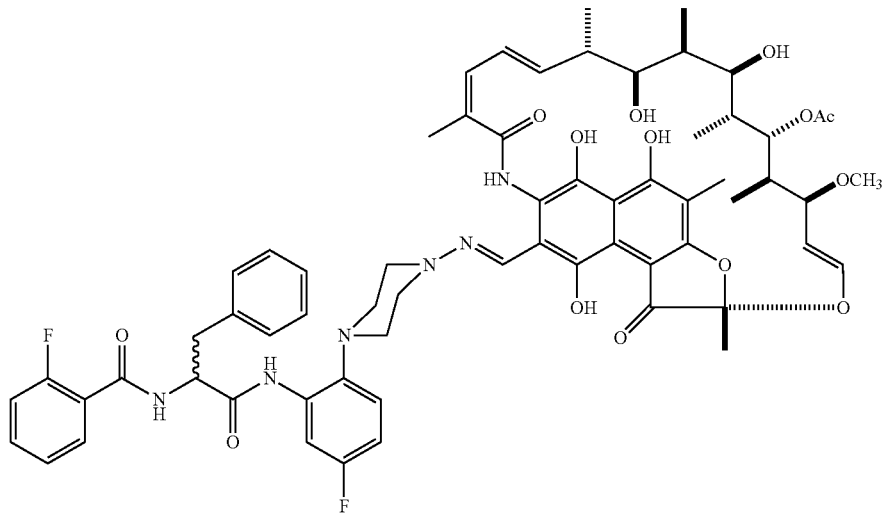

IX-398

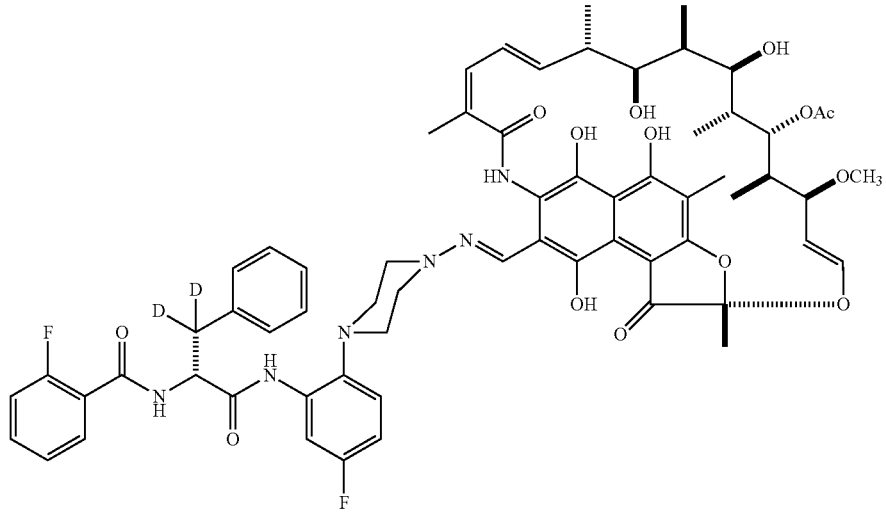

IX-404a

IX-403
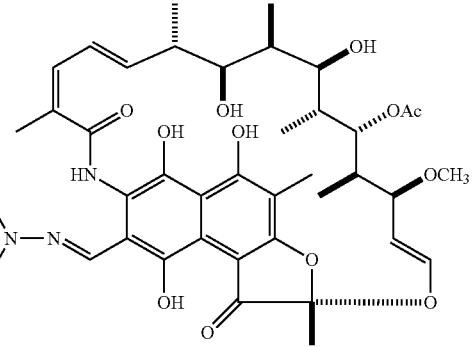
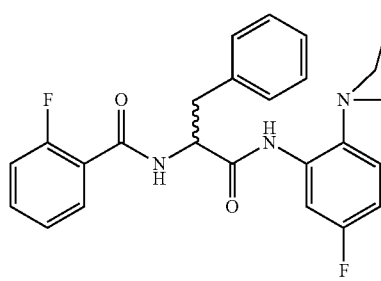
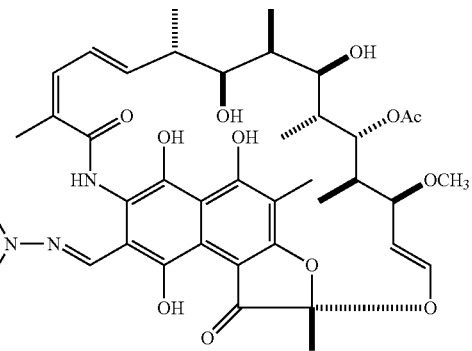
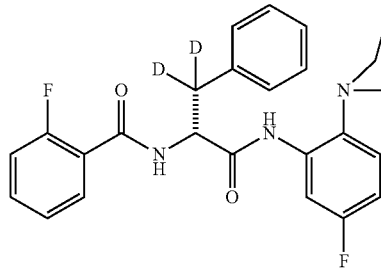
IX-408a
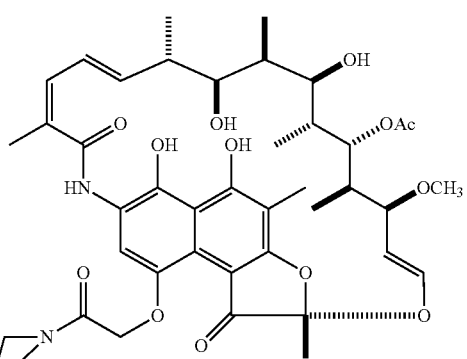
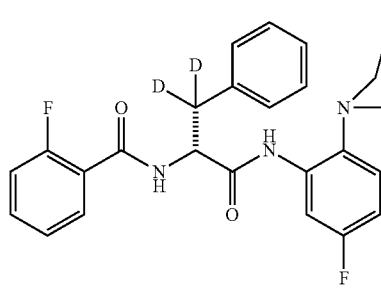

IX-476a
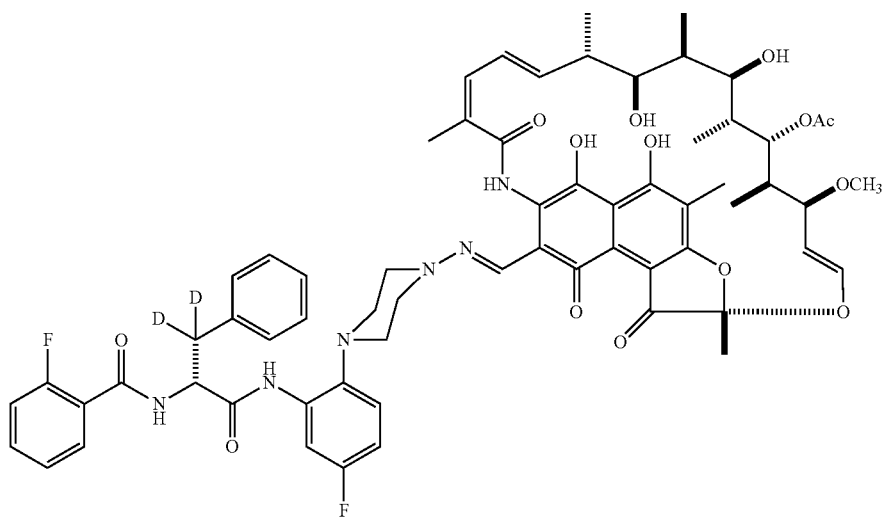
IX-487a
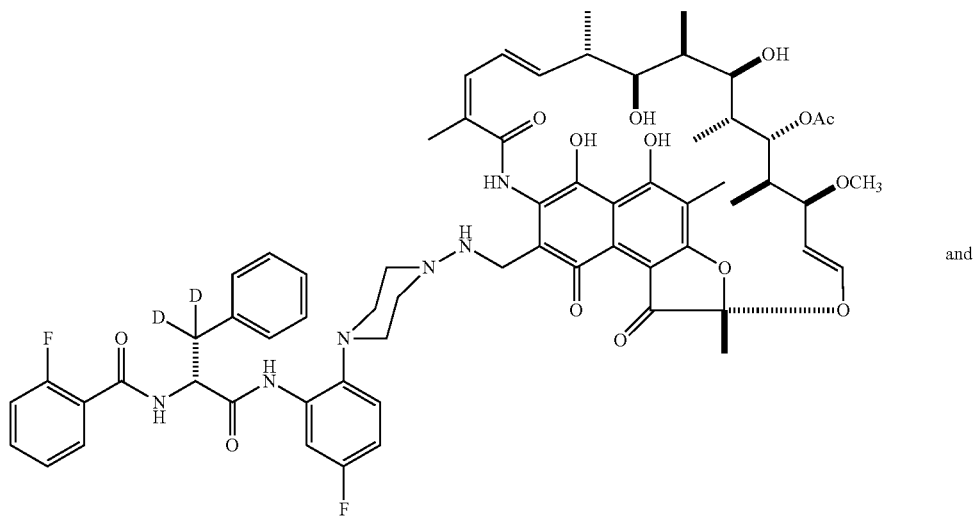
and
IX-491a
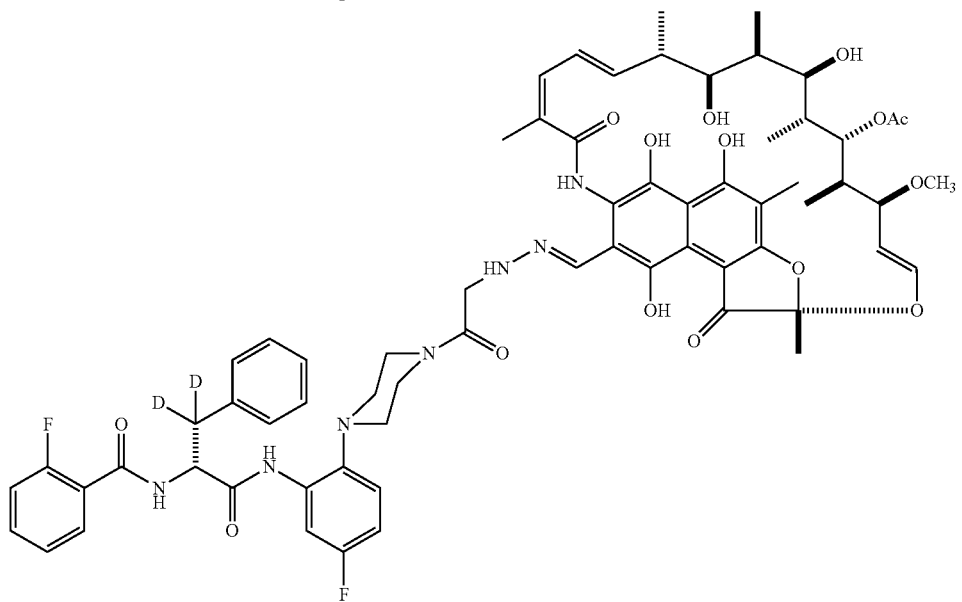
or a salt thereof.

Uses and Methods of Use of Bipartite, Dual-Targeted Inhibitors of RNAP

Coupling of a one of a rifamycin, a streptovaricin, a tolypomycin, and a sorangicin to a moiety that binds to the bridge-helix N-terminus target of a bacterial RNA polymerase; can provide a bipartite inhibitor that interacts alternatively with the Rif target and the bridge-helix N-terminus target of a bacterial RNA polymerase; and therefore that exhibits at least one of the following useful characteristics:
(i) more potent inhibition of a bacterial RNAP than the individual X and the individual Y;
(ii) more potent antibacterial activity than the individual X and the individual Y;
(iii) potent inhibition of a bacterial RNAP resistant to one of the first RNAP inhibitor X and the second RNAP inhibitor Y; and
(iv) potent antibacterial activity against a bacterium resistant to one of the first RNAP inhibitor X and the second RNAP inhibitor Y.

This invention provides a compound comprising a first RNAP inhibitor that functions through the Rif target coupled to a second RNAP inhibitor that functions through the bridge-helix N-terminus target of a bacterial RNA polymerase.

In certain embodiments, a compound of the invention binds to a bacterial RNAP.

In certain embodiments, a compound of the invention binds to a bacterial RNAP resistant to at least one of X and Y.

In certain embodiments, a compound of the invention inhibits a bacterial RNAP.

In certain embodiments, a compound of the invention inhibits a bacterial RNAP with a potency higher than the potency of X and the potency of Y.

In certain embodiments of the invention, a compound of the invention inhibits a bacterial RNAP resistant to at least one of X and Y.

In certain embodiments of the invention, a compound of the invention inhibits bacterial growth. In certain embodiments, a compound of the invention inhibits bacterial growth with potencies higher than the potency of X and the potency of Y.

Certain embodiments provide the use a compound of the invention to bind to a bacterial RNAP.

Certain embodiments provide the use of a compound of the invention to inhibit a bacterial RNAP.

Certain embodiments provide the use of a compound of the invention to inhibit bacterial gene expression.

Certain embodiments provide the use of a compound of the invention to inhibit bacterial growth.

Certain embodiments provide the use of a compound of the invention to treat a bacterial infection.

Certain embodiments provide a composition comprising a compound of the invention or a pharmaceutically acceptable salt thereof, and a pharmaceutically acceptable vehicle.

Certain embodiments provide a method for inhibiting the growth of bacteria comprising contacting the bacteria with a compound of the invention, or a salt thereof.

Certain embodiments provide a method for inhibiting a bacterial RNAP comprising contacting the bacterial RNAP with a compound of the invention, or a salt thereof.

Certain embodiments provide a method for treating a bacterial infection in a mammal, e.g., a human, comprising administering to the mammal an effective amount of a compound of the invention, or a pharmaceutically acceptable salt thereof.

Certain embodiments provide a compound of the invention, or a pharmaceutically acceptable salt thereof, for use in the prophylactic or therapeutic treatment of a bacterial infection.

Certain embodiments provide the use of a compound of the invention, or a pharmaceutically acceptable salt thereof, for the preparation of a medicament for treating a bacterial infection in a mammal, e.g., a human.

In certain embodiments, the targeted bacterial species is selected from Gram-negative bacterial species, including for example, *Escherichia coli* (ECOLI), *Salmonella typhimurium* (SALTY), *Klebsiella pneumoniae* (KLEP7), *Enterococcus cloacae* (ENTCC), *Vibrio cholerae* (VIBCH), *Haemophilus influenzae* (HAEIN), *Neisseria gonorrhoeae* (NEIG1), *Stenotrophomonas maltophilia* (STPMP), *Moraxella catarrhalis* (MORCA), *Acinetobacter baumannii* (ACIBC), and *Pseudomonas aeruginosa* (PSEAE) (FIG. 3).

In certain embodiments, the targeted bacterial species is selected from Mycobacteria, including, for example, *Mycobacterium tuberculosis* (MYCTU), *Mycobacterium bovis*, *Mycobacterium avium* (MYCA1), *Mycobacterium abscessus* (MYCA9), *Mycobacterium abscessus*, *Mycobacterium chelonae*, *Mycobacterium fortuitum*, *Mycobacterium leprae*, *Mycobacterium ulcerans*, and *Mycobacterium smegmatis* (MYCSM) (FIG. 3).

In certain embodiments, the targeted bacterial species is selected from a non-Mycobacterial Gram-positive bacterial species, including, for example, *Staphylococcus aureus* (STAAU), *Staphylococcus epidermidis* (STAEQ), *Enterococcus faecalis* (ENTFA), *Streptococcus pyogenes* (STRP1), *Streptococcus pneumoniae* (STRP2), and *Clostridium difficile* (CDIFF) (FIG. 3).

Methods of Preparing Bipartite, Dual-Targeted Inhibitors of RNAP

The invention also provides a method of preparing a compound having a structural formula (I):

$$X\text{-}\alpha\text{-}Y \quad (I)$$

wherein X comprises a moiety that binds to the Rif target of a bacterial RNA polymerase, Y comprises a moiety that binds to the bridge-helix N-terminus target of a bacterial RNA polymerase, and α is a linker. The method includes providing precursors X-α' and 'α-Y, and reacting moieties α' and 'α to form α. The precursors may include any suitable precursors that will bind to form a linker moiety and permit the X moiety to bind to the Rif target of the RNAP and permit the Y moiety to bind to the bridge-helix N-terminus target of a bacterial RNA polymerase.

For example, in a preferred embodiment, one precursor contains an aldehyde, a ketone, a protected aldehyde, or a protected ketone, and the other precursor contains a hydrazide or an amine. In another preferred embodiment, one precursor contains an activated ester, an imidazolide, or an anhydride and the other precursor contains an amine. In another preferred embodiment, one precursor contains a halogen and the other precursor contains an amine. In another preferred embodiment, one precursor contains a halogen and the other precursor contains a sulfhydryl. In another preferred embodiment, one precursor contains an azide and the other precursor contains an alkyne. In another preferred embodiment, one precursor contains an azide and the other precursor contains a phosphine. In another preferred embodiment, one precursor contains a boronic acid and the other precursor contains a substituted phenol. In another preferred embodiment, one precursor contains phenylboronic acid and the other precursor contains salicylhydroxamic acid.

Each of the above-referenced chemistries are established and are known to those skilled in the art (see Rostovetsev, et al. (2002) *Angew. Chem. Int. Ed.* 41, 2596-2599 Wang, et al. (2003) *J. Amer. Chem. Soc.* 125, 3192-3193; Breibauer, et al. (2003) *ChemBioChem.* 4, 1147-1149; Saxon, et al. (2000) *Science* 287, 2007-2010; Kiick, et al. (2002), *Proc. Natl. Acad. Sci. USA* 99, 19-24; Kohn, et al. (2004) *Angew. Chem. Int. Ed.* 43, 3106-3116; Stolowitz, et al. (2001) *Bioconj. Chem.* 12, 229-239; Wiley, et al. (2001), 12, 240-250).

In one embodiment, moieties α' and 'α of precursors X-α' and 'α-Y are reacted in the absence of a bacterial RNAP.

In another embodiment, moieties α' and 'α of precursors X-α' and 'α-Y are reacted in the presence of a bacterial RNAP. In this embodiment, the bacterial RNAP potentially can serve as a template for reaction of X-α' and 'α-Y.

Certain embodiments of the invention provide a method of making a compound of the invention, wherein the compound is prepared from precursors X-α' and 'α-Y, wherein α' and 'α are moieties that can react to form α.

In certain embodiments, one precursor contains an aldehyde, a ketone, a protected aldehyde, or a protected ketone, and the other precursor contains a hydrazide or an amine.

In certain embodiments, one precursor contains an activated ester, an imidazolide, or an anhydride, and the other precursor contains an amine.

In certain embodiments, one precursor contains a haloacetyl moiety, and the other precursor contains an amine.

In certain embodiments, one precursor contains a halogen, and the other precursor contains an amine.

In certain embodiments, one precursor contains a haloacetyl moiety, and the other precursor contains a sulfhydryl.

In certain embodiments, one precursor contains a halogen, and the other precursor contains a sulfhydryl.

In certain embodiments, one precursor contains an azide, and the other precursor contains an alkyne.

In certain embodiments, one precursor contains an azide, and the other precursor contains a phosphine.

In certain embodiments, one precursor contains a boronic acid, and the other precursor contains a substituted phenol.

In certain embodiments, one precursor contains phenylboronic acid, and the other precursor contains salicylhydroxamic acid.

In certain embodiments, precursors X-α' and 'α-Y are allowed to react in the absence of a bacterial RNAP.

In certain embodiments, precursors X-α' and 'α-Y are allowed to react in the presence of a bacterial RNAP.

In certain embodiments, the bacterial RNAP serves as a template for reaction of X-α' and 'α-Y.

Pharmaceutical Preparations and Methods of Administration

In cases where compounds are sufficiently basic or acidic, a salt of a compound of the invention can be useful as an intermediate for isolating or purifying a compound of the invention. Additionally, administration of a compound of the invention as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compound of the invention can be formulated as pharmaceutical compositions and administered to a mammalian host, such as a human patient in a variety of forms adapted to the chosen route of administration, i.e., orally or parenterally, by intravenous, intramuscular, topical, or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compound of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compound of the invention can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 150 mg/kg, e.g., from about 10 to about 100 mg/kg of body weight per day, such as 3 to about 75 mg per kilogram body weight of the recipient per day, preferably in the range of 6 to 120 mg/kg/day, most preferably in the range of 15 to 90 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

INDUSTRIAL APPLICABILITY

Compounds identified according to the target and method of this invention would have applications not only in antibacterial therapy, but also in: (a) identification of bacterial RNAP (diagnostics, environmental-monitoring, and sensors applications), (b) labeling of bacterial RNAP (diagnostics, environmental-monitoring, imaging, and sensors applications), (c) immobilization of bacterial RNAP (diagnostics, environmental-monitoring, and sensors applications), (d) purification of bacterial RNA polymerase (biotechnology applications), (e) regulation of bacterial gene expression (biotechnology applications), and (f) antisepsis (antiseptics, disinfectants, and advanced-materials applications).

EXAMPLES

With reference to the examples below, Applicant has identified compounds that inhibit bacterial RNAP.

Example 1: Synthesis of 2-fluoro-N-(1-((5-fluoro-2-(piperazin-1-yl)phenyl)amino)-1-oxo-3-phenylpropan-2-yl)benzamide (IX-214)

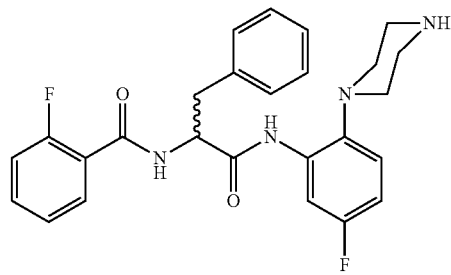 [SMILES: O=C(NC(Cc1ccccc1)C(=O)Nc1cc(F)ccc1N1CCNCC1)c1ccccc1F]

IX-214 was synthesized as in Ebright, R. H., Ebright, Y., Mandal, S., Wilde, R., and Li, S. (2015) WO2015/120320.

Example 2: Synthesis of (R)-2-fluoro-N-(1-((5-fluoro-2-(piperazin-1-yl)phenyl)amino)-1-oxo-3-phenylpropan-2-yl-3,3-d$_2$)benzamide (IX-370a)

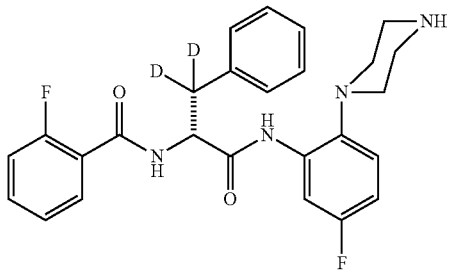 [SMILES: [2H]C([2H])(c1ccccc1)[C@@H](NC(=O)c1ccccc1F)C(=O)Nc1cc(F)ccc1N1CCNCC1]

Example 2.1: t-Butyl 4-(4-fluoro-2-nitrophenyl)piperazine-1-carboxylate

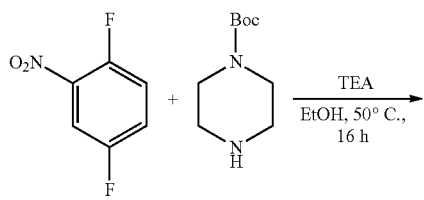

To a solution of 2,5-difluoronitrobenzene (3.2 mL; 29.5 mmol; Sigma-Aldrich) in ethanol (59 mL), was added 1-Boc-piperazine (6.05 g; 32.5 mmol; Sigma-Aldrich) and triethylamine (4.11 mL; 29.5 mmol; Sigma-Aldrich), and the reaction mixture was stirred 16 h at 50° C. and then allowed to cool to room temperature. The reaction mixture was evaporated and then extracted with ethyl acetate (30 mL). The extract was dried over anhydrous sodium sulfate, filtered, and evaporated to dryness, and the crude product was purified by silica chromatography (ethyl acetate/hexanes gradient). Yield: 6.18 g; 64%. 1H NMR (500 MHz, CDCl$_3$): δ 7.51 (dd, 1H), 7.26-7.23 (m, 1H), 7.17 (dd, 1H), 3.56 (t, 4H), 2.95 (brs, 4H), 1.47 (s, 9H).

Example 2.2: t-Butyl 4-(2-amino-4-fluorophenyl)piperazine-1-carboxylate

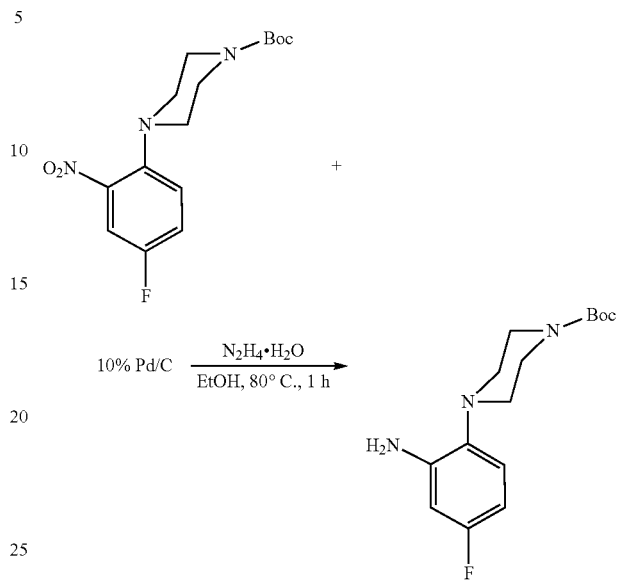

To a solution of t-butyl 4-(4-fluoro-2-nitrophenyl)piperazine-1-carboxylate (6.18 g; 19 mmol; Example 2.1) in ethanol (79 mL), was added 10% Pd/C (794 mg; Sigma-Aldrich) and hydrazine monohydrate (4.3 mL; 88.65 mmol; Sigma-Aldrich), and the reaction mixture was stirred 1 h at 80° C. After cooling to room temperature, the reaction mixture was filtered through a pad of Celite 521 (Sigma-Aldrich). The filtrate was concentrated to an oil, re-dissolved in ethyl acetate (80 mL), dried over anhydrous sodium sulfate, filtered, and evaporated to dryness. The crude product was used in the next step without further purification.

Crude yield: 5.62 g; 99%. 1H NMR (500 MHz, CDCl$_3$): δ 6.90-6.86 (m, 1H), 6.44-6.37 (m, 2H), 4.13-4.10 (m, 2H), 3.56 (br, 4H), 2.78 (brs, 4H), 1.48 (d, 9H).

Example 2.3: D-phenylalanine-3,3'-d$_2$

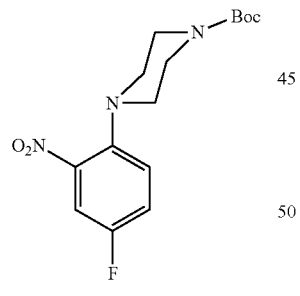

D-phenylalanine-3,3'-d$_2$ was prepared using procedures described for preparation of L-phenylalanine-3,3'-d$_2$ (Maegawa et. al. *Synlett* 2005, 845). A suspension of D-phenylalanine (330 mg; 2 mmol; Chem-Impex) and 10% Pd/C (33 mg; Sigma-Aldrich) in deuterium oxide (8 mL; 99.9% D; Sigma-Aldrich) was heated 6 h at 110° C. under H₂ (balloon). After cooling to room temperature, the reaction mixture was filtered through a pad of Celite 521 (Signa-Aldrich). The filtrate was concentrated to a solid, dissolved in 10 mL water and 10 mL methanol, and evaporated to yield D-phenylalanine-3,3'-d₂. The crude product was used in the next step without further purification. Crude yield: 316 mg; 95%. 1H NMR (500 MHz, D₂O): δ 7.30-7.27 (m, 2H), 7.25-7.21 (m, 1H), 7.20-7.17 (m, 2H), 3.84 (s, 1H).

Example 2.4: N-Fmoc-D-phenylalanine-3,3'-d₂

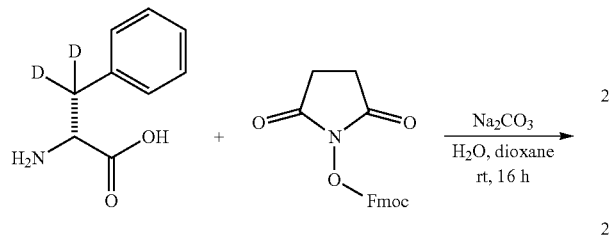

To a suspension of D-phenylalanine-3,3'-d₂ (1.19 g; 7.12 mmol; Example 2.3) in 10% sodium carbonate (8.4 mL; Fisher Scientific), was added Fmoc N-hydroxysuccinimide ester (2.64 g; 7.83 mmol; Chem-Impex) in dioxane (8.8 mL; Sigma-Aldrich). The reaction was stirred 16 h at room temperature, diluted with water (20 mL), and extracted with ethyl acetate (2×20 mL). The aqueous layer was poured into ethyl acetate (30 mL), acidified with 1 N HCl to pH 3, and extracted with ethyl acetate (3×30 mL). The pooled extracts were washed with 1 N HCl (2×30 mL), water (2×30 mL), and brine (30 mL), and then dried over anhydrous sodium sulfate, filtered, and evaporated. The crude product was directly used in the next step without further purification. Crude yield: 2.41 g; 87%.

Example 2.5: t-Butyl (R)-4-(2-(2-((((9H-fluoren-9-yl)methoxy)carbonyl)amino)-3-phenylpropanamido-3,3-d₂)-4-fluorophenyl)piperazine-1-carboxylate

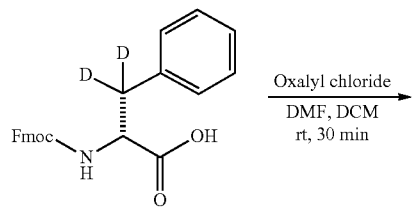

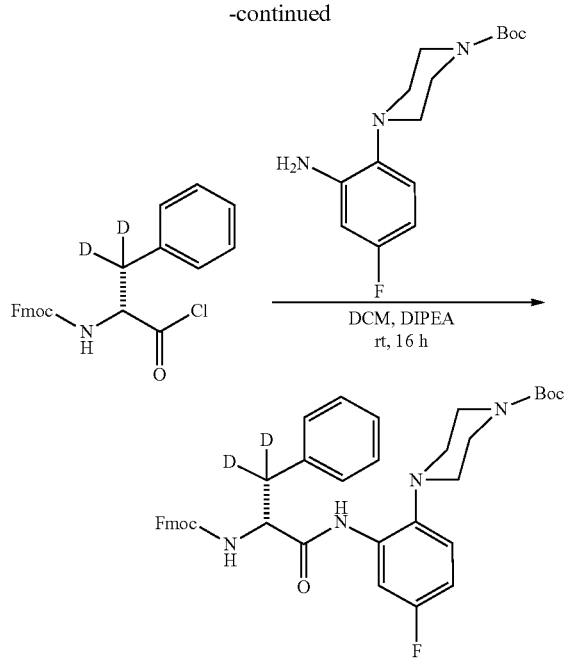

To a suspension of N-Fmoc-D-phenylalanine-3,3'-d₂ (2.41 g; 6.19 mmol; Example 2.4) in dichloromethane (28 mL), was added oxalyl chloride (0.79 mL; 9.28 mmol; Sigma-Aldrich) and dimethylformamide (60 µL), and the reaction mixture was stirred 30 min at room temperature under argon. The reaction mixture was evaporated to dryness, re-dissolved in dichloromethane (28 mL), supplemented with t-Butyl 4-(2-amino-4-fluorophenyl)piperazine-1-carboxylate (1.826 g; 6.18 mmol; Example 2.2) and N,N-diisopropylethylamine (1.6 ml; 9.19 mmol; Sigma-Aldrich), and stirred 16 h at room temperature under argon. The reaction mixture was washed with 0.5 M HCl (30 mL) and saturated sodium bicarbonate (30 mL), and was extracted with dichloromethane (3×30 mL). The pooled extracts were dried over anhydrous sodium sulfate, filtered, and evaporated to dryness, and the product was purified by silica chromatography (ethyl acetate/hexanes gradient). Yield: 2.9 g; 70%. MS (MALDI): calculated: m/z 666.79 (M+H⁺); found: 667.25 (M+H⁺).

Example 2.6: t-Butyl (R)-4-(2-(2-amino-3-phenyl-propanamido-3,3-d₂)-4-fluorophenyl)piperazine-1-carboxylate

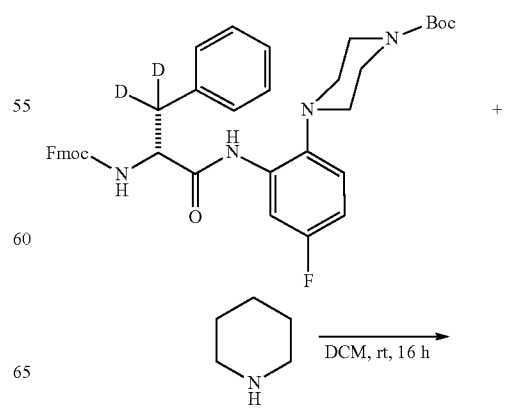

-continued

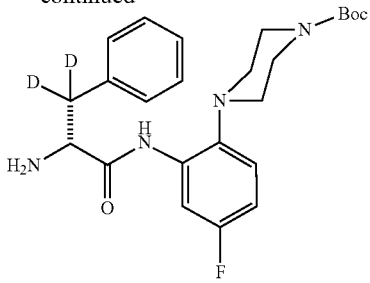

To a solution of t-butyl (R)-4-(2-(2-((((9H-fluoren-9-yl)methoxy)carbonyl)amino)-3-phenylpropanamido-3,3-d$_2$)-4-fluorophenyl)piperazine-1-carboxylate (2.9 g; 4.35 mmol; Example 2.5) in dichloromethane (34 mL; Sigma-Aldrich), was added piperidine (1.72 mL; 17.41 mmol; Sigma-Aldrich), and the reaction mixture was stirred 16 h at room temperature. The reaction mixture was evaporated to dryness, 1 N HCl was added to adjust pH to 7, and the reaction mixture was extracted with dichloromethane (3×30 mL). The pooled extracts were dried over anhydrous sodium sulfate, filtered, and evaporated, and the product was purified by silica chromatography (ethyl acetate/hexanes gradient). Yield: 1.82 g; 94%.

Example 2.7: t-Butyl (R)-4-(4-fluoro-2-(2-(2-fluorobenzamido)-3-phenylpropanamido-3,3-d$_2$)phenyl)piperazine-1-carboxylate

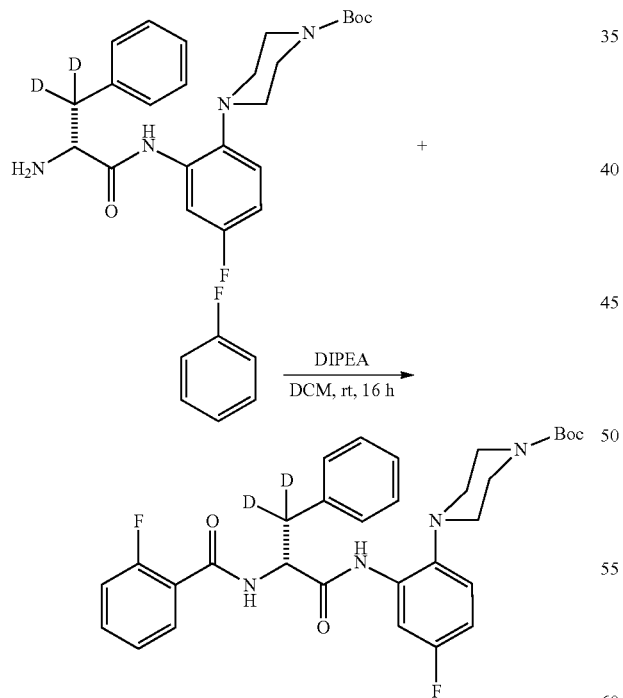

To a solution of t-butyl (R)-4-(2-(2-amino-3-phenylpropanamido-3,3-d$_2$)-4-fluorophenyl)piperazine-1-carboxylate (1.82 g; 4.1 mmol; Example 2.6) in dichloromethane (40 mL), was added 2-fluorobenzoyl chloride (0.74 mL; 6.2 mmol; Sigma-Aldrich) and N,N-diisopropylethylamine (1.1 mL; 6.32 mmol; Sigma-Aldrich), and the reaction mixture was stirred 16 h at room temperature under argon. The reaction mixture was diluted with dichloromethane (40 mL) and extracted with 0.5 N HCl (2×40 mL). The pooled extracts were dried over anhydrous sodium sulfate, filtered, and evaporated, and the product was purified by silica chromatography (ethyl acetate/hexanes gradient).
Yield: 1.73 g; 75%.

Example 2.8: (R)-2-fluoro-N-(1-((5-fluoro-2-(piperazin-1-yl)phenyl)amino)-1-oxo-3-phenylpropan-2-yl-3,3-d$_2$)benzamide (IX-370a)

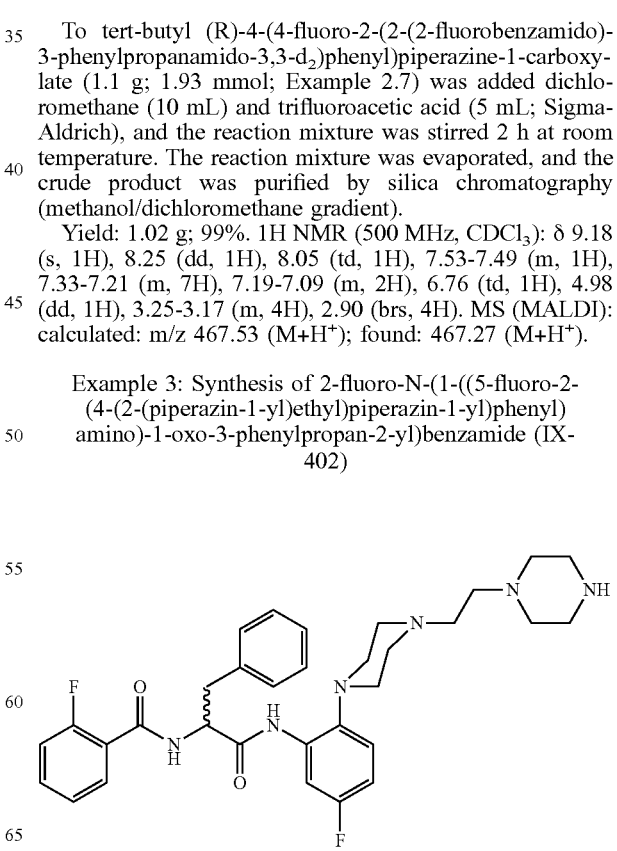

To tert-butyl (R)-4-(4-fluoro-2-(2-(2-fluorobenzamido)-3-phenylpropanamido-3,3-d$_2$)phenyl)piperazine-1-carboxylate (1.1 g; 1.93 mmol; Example 2.7) was added dichloromethane (10 mL) and trifluoroacetic acid (5 mL; Sigma-Aldrich), and the reaction mixture was stirred 2 h at room temperature. The reaction mixture was evaporated, and the crude product was purified by silica chromatography (methanol/dichloromethane gradient).
Yield: 1.02 g; 99%. 1H NMR (500 MHz, CDCl$_3$): δ 9.18 (s, 1H), 8.25 (dd, 1H), 8.05 (td, 1H), 7.53-7.49 (m, 1H), 7.33-7.21 (m, 7H), 7.19-7.09 (m, 2H), 6.76 (td, 1H), 4.98 (dd, 1H), 3.25-3.17 (m, 4H), 2.90 (brs, 4H). MS (MALDI): calculated: m/z 467.53 (M+H$^+$); found: 467.27 (M+H$^+$).

Example 3: Synthesis of 2-fluoro-N-(1-((5-fluoro-2-(4-(2-(piperazin-1-yl)ethyl)piperazin-1-yl)phenyl)amino)-1-oxo-3-phenylpropan-2-yl)benzamide (IX-402)

Example 3.1: t-Butyl 4-(2-(4-(4-fluoro-2-(2-(2-fluorobenzamido)-3-phenylpropanamido)phenyl)piperazin-1-yl)ethyl)piperazine-1-carboxylate

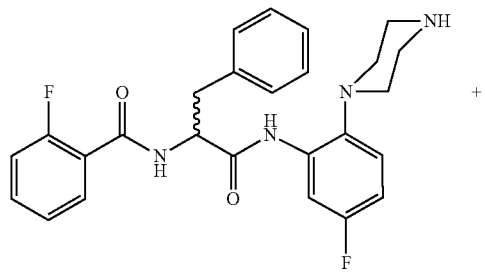

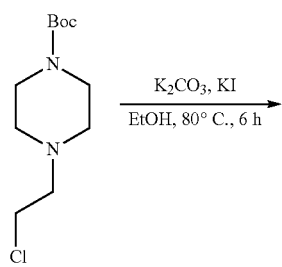

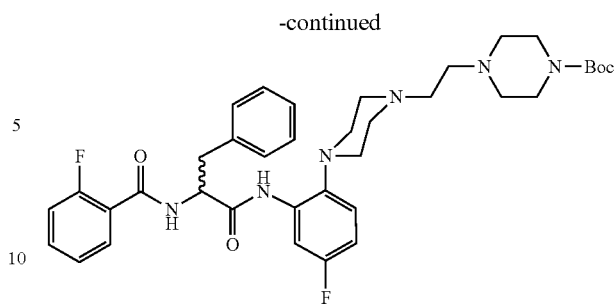

A suspension of IX-214 (30 mg; 0.065 mmol; Example 1), potassium carbonate (9 mg; 0.065 mmol), and potassium iodide (2 mg; 0.012 mmol) in ethanol (1 mL) was stirred 5 min at room temperature, was supplemented with t-butyl 4-(2-chloroethyl)piperazine-1-carboxylate (24.3 mg; 0.098 mmol; Acros Organics), and was stirred 6 h at 80° C. The reaction mixture was evaporated, re-dissolved in 10 mL water, and extracted with dichloromethane (3×10 mL). The pooled extracts were dried over anhydrous sodium sulfate, filtered, and evaporated, and the product was purified by silica chromatography (methanol/dichloromethane gradient).

Yield: 34.4 mg; 79%.

Example 3.2: 2-Fluoro-N-(1-((5-fluoro-2-(4-(2-(piperazin-1-yl)ethyl)piperazin-1-yl)phenyl)amino)-1-oxo-3-phenylpropan-2-yl)benzamide (IX-402)

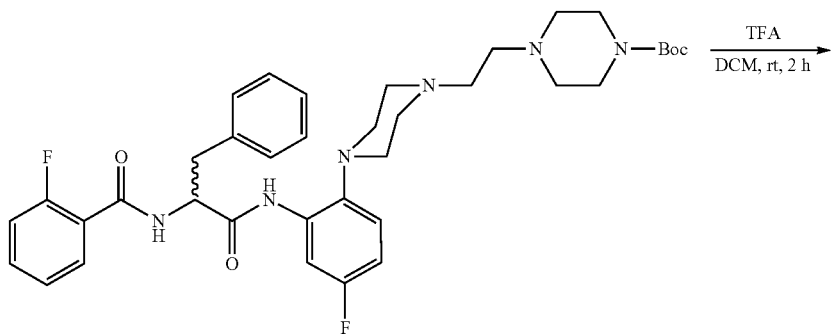

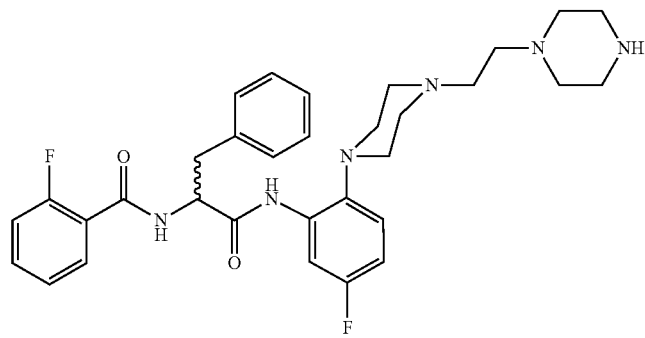 [SMILES: O=C(NC(Cc1ccccc1)C(=O)Nc1cc(F)ccc1N1CCN(CCN2CCNCC2)CC1)c1ccccc1F]

To tert-butyl 4-(2-(4-(4-fluoro-2-(2-(2-fluorobenzamido)-3-phenylpropanamido)-phenyl)piperazin-1-yl)ethyl)piperazine-1-carboxylate (34 mg; 0.05 mmol; Example 3.1), was added dichloromethane (0.5 mL) and trifluoroacetic acid (125 µL; Sigma-Aldrich), and the reaction mixture was stirred 2 h at room temperature. The reaction mixture was evaporated, and the crude product was purified by silica chromatography (methanol/dichloromethane/ammonium hydroxy gradient). Yield: 9 mg; 30%. 1H NMR (500 MHz, CDCl$_3$): δ 8.93 (s, 1H), 8.27-8.24 (m, 1H), 8.11 (td, 1H), 7.53-7.49 (m, 1H), 7.41-7.38 (m, 1H), 7.29-7.26 (m, 5H), 7.23-7.21 (m, 1H), 7.18-7.13 (m, 1H), 7.06-7.03 (m, 1H), 6.72 (td, 1H), 5.01-4.99 (m, 1H), 3.42-3.38 (m, 1H), 3.24-3.20 (m, 1H), 2.94 (d, 4H), 2.59-2.29 (m, 17H). MS (MALDI): calculated: m/z 577.69 (M+H$^+$); found: 577.17 (M+H$^+$).

Example 4: Synthesis of Rifamycin SV—(CHN)—IX-214 Conjugate (IX-398)

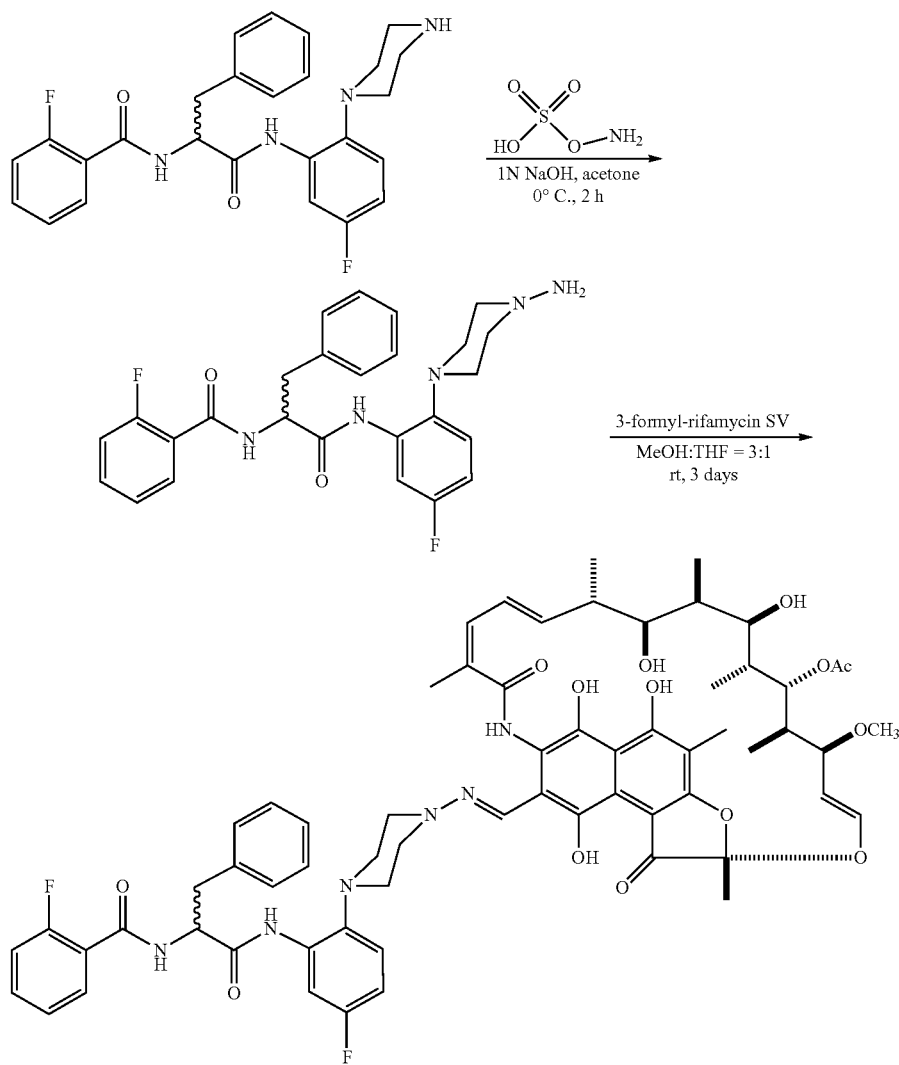

To a suspension of IX-214 (30 mg; 0.065 mmol; Example 1) in 0.5 mL 1 N NaOH at 0° C., was added acetone (0.25 mL) and hydroxyaminine-O-sulfuric acid in 20 µL water (9 mg; 0.08 mmol; Sigma-Aldrich; dissolved immediately before use), and the reaction mixture was stirred 2 h at 0° C. and then allowed to come to room temperature. Following addition of glacial acetic acid (30 µL) to acidify the reaction mixture to pH 5, the reaction mixture was supplemented with ascorbic acid (6 mg; Sigma-Aldrich), methanol (1 mL), and 3-formylrifamycin SV freshly dissolved in 150 µL 3:1 v/v methanol/tetrahydrofuran (31 mg; 0.043 mmol; AvaChem Scientific), and the reaction mixture was stirred 3 days at room temperature. The reaction mixture was evaporated to dryness, re-dissolved in 5 mL water, and extracted with dichloromethane (3×5 mL). The pooled extracts were dried over anhydrous sodium sulfate, filtered, and evaporated. The sample was dissolved in dichloromethane (2 mL) and 5% citric acid/0.5% ascorbic acid aqueous solution (2 mL), stirred 2 h at room temperature and extracted with dichloromethane (3×5 mL). The pooled extracts were collected, dried over anhydrous sodium sulfate, filtered, and evaporated, and the product was purified by silica chromatography (methanol/dichloromethane gradient). Yield: 19.2 mg; 38%. MS (MALDI): calculated: m/z 1188.30 (M+H$^+$); found: 1209.27 (M+Na$^+$).

Example 5: Synthesis of Rifamycin SV—(CHN)—IX-370a Conjugate (IX-404a)
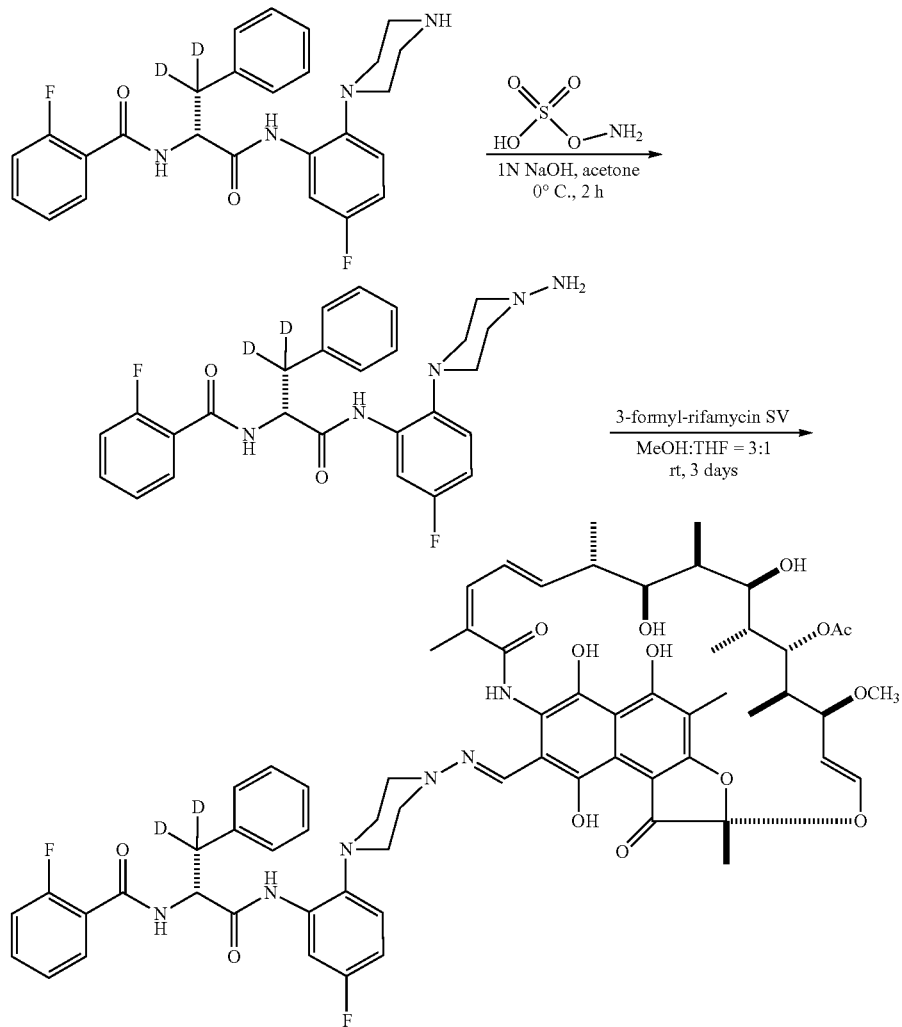
IX-404a was prepared as described for IX-398 in Example 4, but using IX-370a (Example 2) in place of IX-214. Yield: 33 mg; 32%. MS (MALDI): calculated: m/z 1190.32 (M+H$^+$); found: 1211.22 (M+Na$^+$).
Example 6: Synthesis of Rifamycin SV—(CHN)—IX-402 Conjugate (IX-403)
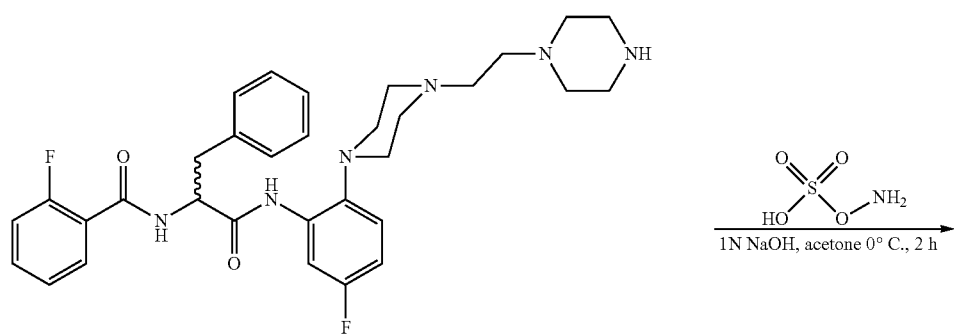

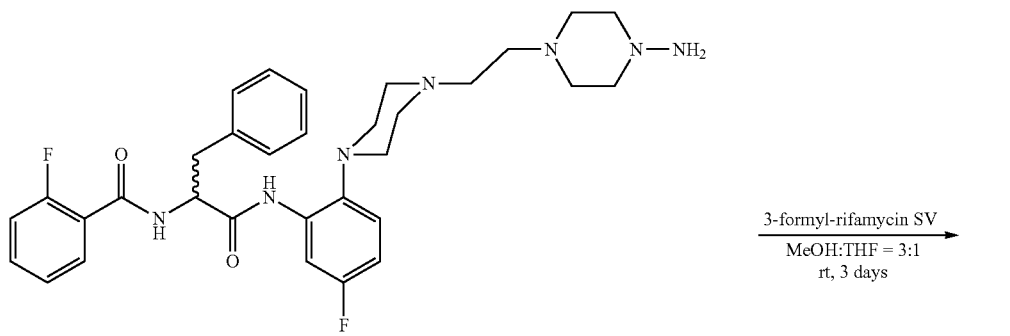
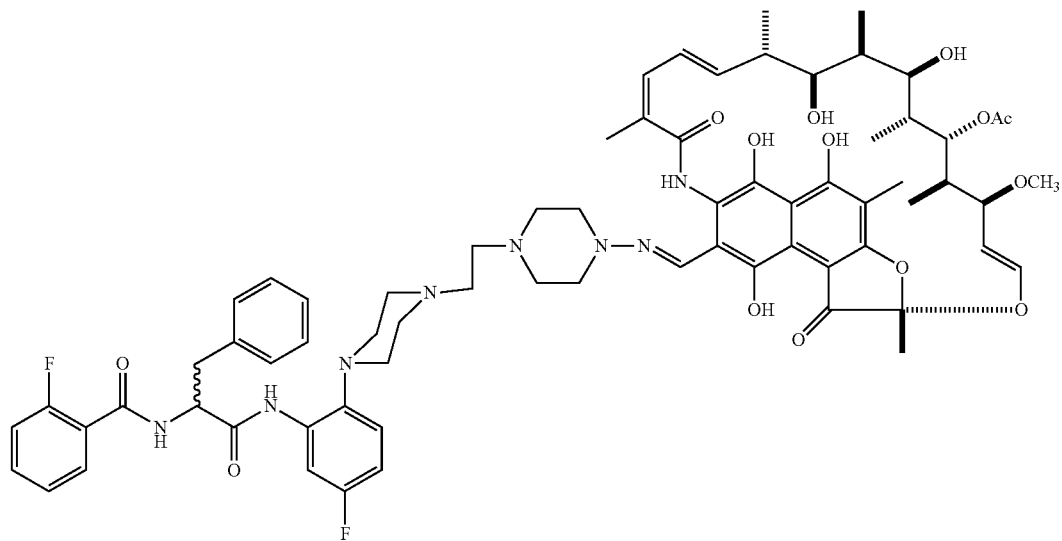
IX-403 was prepared as described for IX-398 in Example 4, but using IX-402 (Example 3) in place of IX-214. Yield: 25.4 mg; 34%. MS (MALDI): calculated: m/z 1300.48 (M+H$^+$); found: 1267.31 (M-MeOH), 1299.31 (M+H$^+$).
Example 7: Synthesis of Rifamycin B—IX-370a Conjugate (IX-408a)
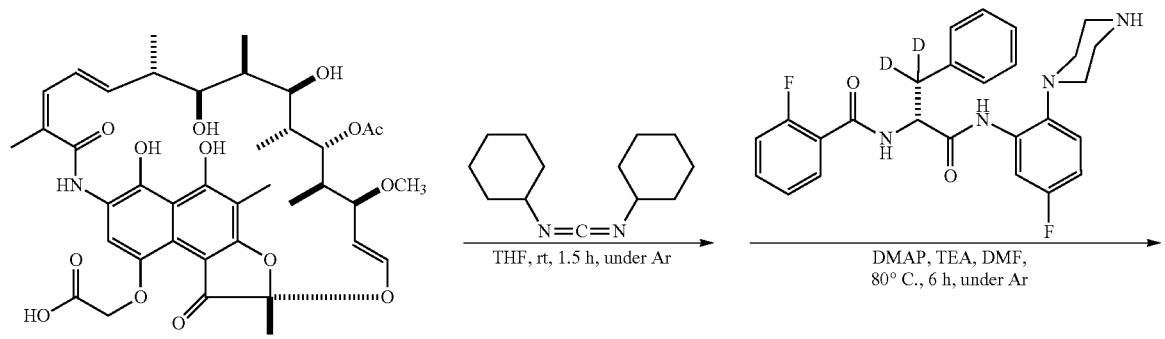

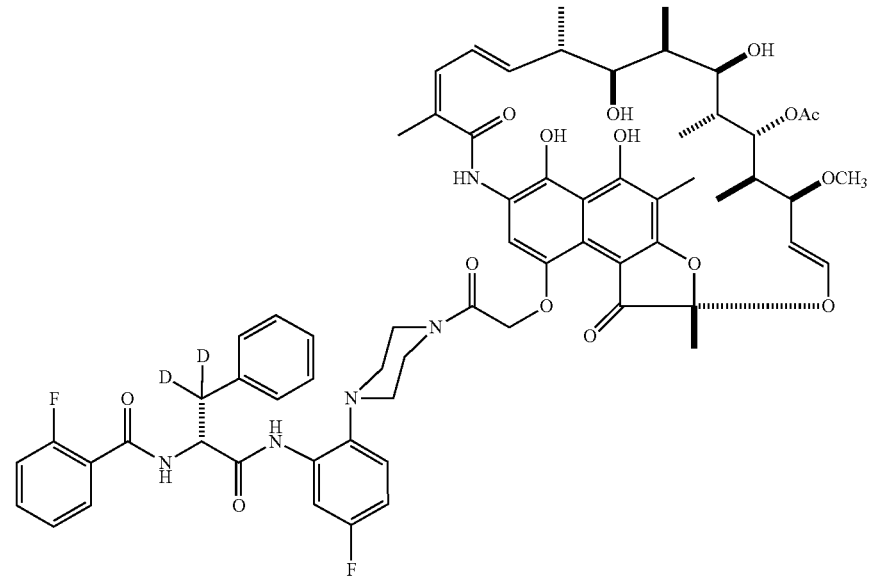

To a suspension of rifamycin B (150 mg; 0.20 mmol; AvaChem Scientific) in 3 mL tetrahydrofuran at room temperature under argon, was added a solution of N,N'-dicyclohexylcarbodiimide (150 mg; 0.73 mmol; Sigma-Aldrich) in 1 mL tetrahydrofuran, and the reaction mixture was stirred 1.5 h at room temperature. The reaction mixture was filtered off, and the filtrate was added to 25 mL anhydrous diethyl ether, yielding a yellow precipitate. The resulting yellow precipitate was dissolved in 3.75 mL dimethylformamide, and IX-370a (113 mg; 0.24 mmol; Example 2.8) in 2.8 mL dimethylformamide, 4-dimethylaminopyridine (2.4 mg; 0.02 mmol; Alfa Aesar), and triethylamine (0.056 mL; 0.4 mmol; Sigma-Aldrich) successively were added, and the reaction mixture was stirred 6 h at 80° C., and then evaporated to dryness. The product was purified by silica chromatography (methanol/dichloromethane gradient). Yield: 94.6 mg; 40%. MS (MALDI): calculated: m/z 1205.33 (M+H$^+$); found: 1173.27 (M+H$^+$-MeOH).

Example 8: Synthesis of Rifamycin S—(CHN)—IX-370a Conjugate (IX-476a)

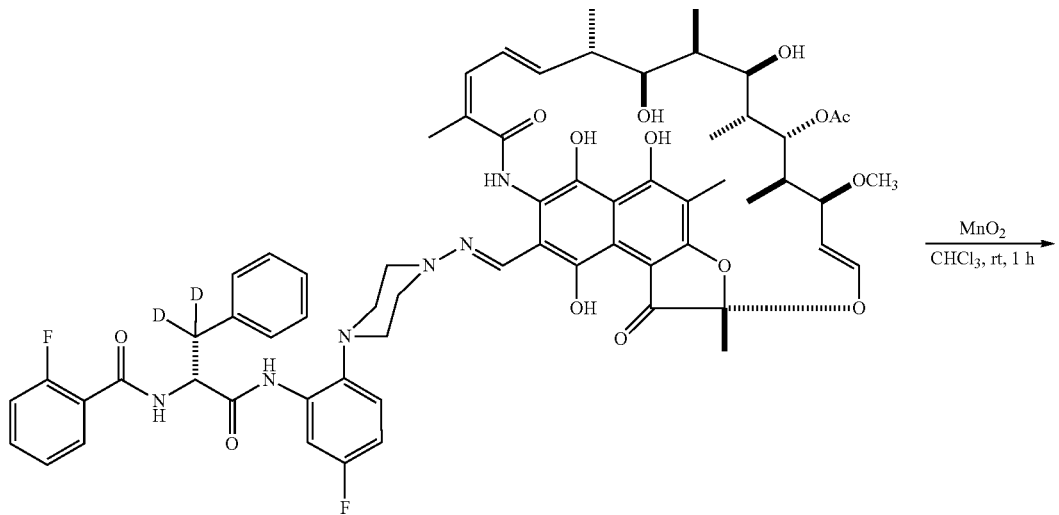

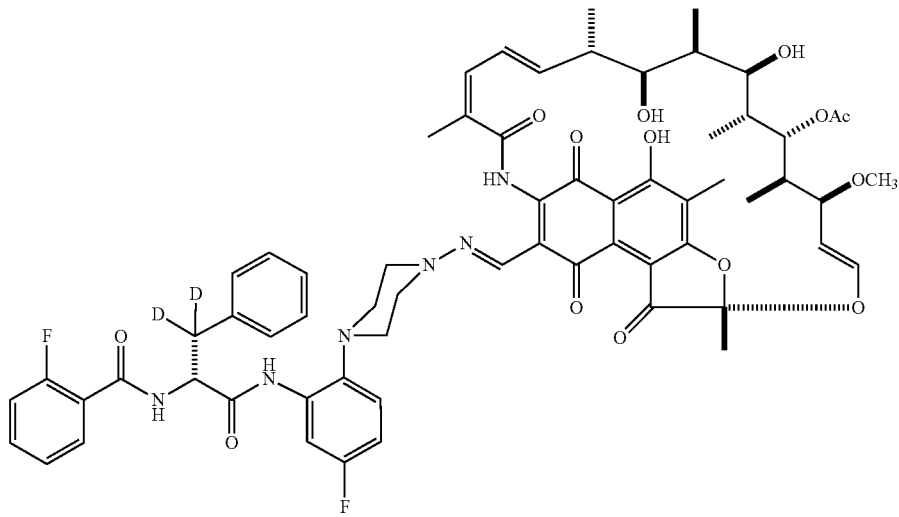

To a solution of IX-404a (100 mg; 0.084 mmol; Example 5) in 2 mL CHCl$_3$ at room temperature, was added 70% manganese(IV) oxide (261 mg; 2.1 mmol), and the reaction mixture was stirred 1 h at 25° C. The reaction mixture was filtered and evaporated to dryness, and the crude product was purified by silica chromatography (petroleum ether/ethyl acetate gradient). Yield: 30.8 mg; 31%. $^1$H NMR (400 MHz, CDCl$_3$): δ 13.10-12.50 (m, 1H), 10.64-10.20 (m, 1H), 9.09 (s, 1H), 8.31 (dd, 1H), 8.06 (dt, 1H), 7.61 (s, 1H), 7.43-7.35 (m, 1H), 7.35-7.27 (m, 6H), 7.26-7.20 (m, 2H), 7.10-6.89 (m, 4H), 6.75 (dt, 1H), 6.46 (brd, 1H), 6.11 (dd, 1H), 5.97 (brdd, 1H), 5.18-4.94 (m, 3H), 4.00-3.83 (m, 2H), 3.68-3.32 (m, 2H), 2.71 (brd, 6H), 2.50-2.02 (m, 12H), 1.85-1.75 (m, 5H), 1.52-1.37 (m, 2H), 1.11-0.78 (m, 11H), 0.51 (d, 3H), 0.16 (brd, 3H).

Example 9: Synthesis of Rifamycin SV—(CHNNHCH$_2$CO)—IX-370a Conjugate (IX-491a)

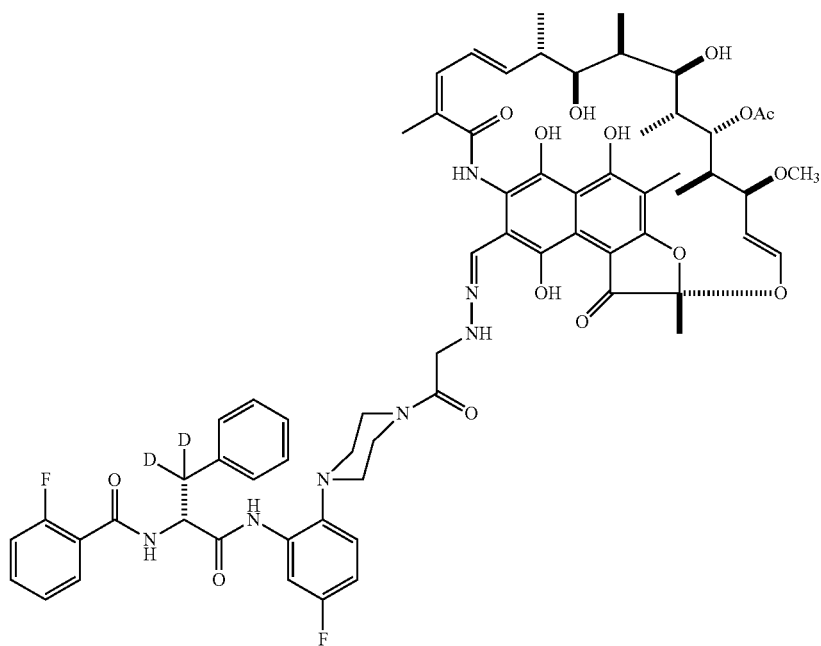 [SMILES: [2H]C([2H])(c1ccccc1)[C@@H](NC(=O)c1ccccc1F)C(=O)Nc1cc(F)ccc1N1CCN(C(=O)CNN=Cc2c3c(O)c4c(O)c(C)c5c(c4c2O)C(=O)[C@@](C)(O/C=C/[C@H](OC)[C@@H](C)[C@@H](OC(C)=O)[C@H](C)[C@H](O)[C@H](C)[C@@H](O)[C@@H](C)/C=C/C=C(/C)C(=O)N3)O5)CC1]

Example 9.1: (R)—N-(1-((2-(4-(2-bromoacetyl)piperazin-1-yl)-5-fluorophenyl)amino)-1-oxo-3-phenylpropan-2-yl-3,3-d₂)-2-fluorobenzamide

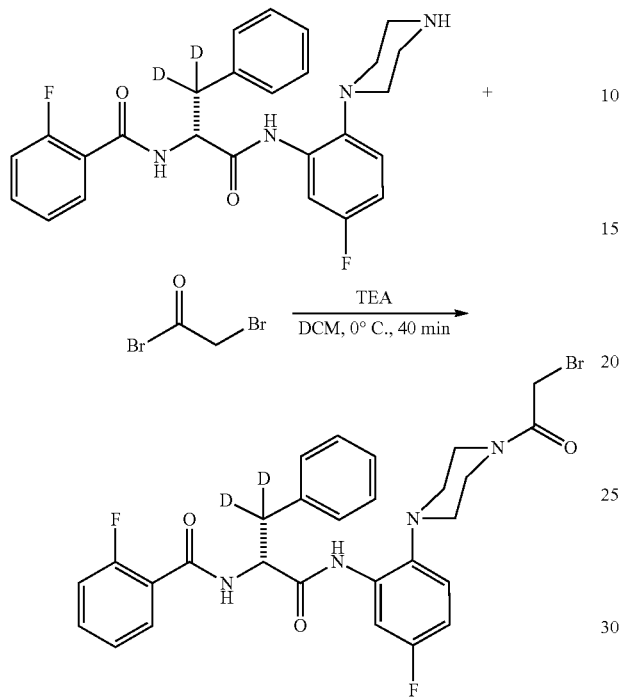

To a solution of IX-370a (200 mg; 0.43 mmol; Example 2) in 4 mL dichloromethane at 0° C. under argon, was added trimethylamine (0.15 mL; 1.08 mmol; Sigma-Aldrich), and the reaction mixture was stirred 15 minutes at 0° C. Following addition of a solution of bromoacetyl bromide (46 μl; 0.52 mmol; Acros Organics) in 1.2 mL dichloromethane, the reaction mixture was stirred 40 minutes at 0° C. under argon. The reaction mixture was diluted with water (10 mL) and extracted with dichloromethane (3×10 mL); the pooled extracts were dried over anhydrous sodium sulfate, filtered, and evaporated; and the product was purified by silica chromatography (ethyl acetate/hexanes gradient). Yield: 152 mg; 60%. $^1$H NMR (500 MHz, CDCl$_3$): δ 9.03 (s, 1H), 8.27 (dd, 1H), 8.08 (t, 1H), 7.53-7.50 (m, 1H), 7.37-7.26 (m, 7H), 7.14 (dd, 1H), 7.01 (dd, 1H), 6.74 (td, 1H), 5.00 (d, 1H), 3.83 (s, 2H), 3.40 (brs, 4H), 2.65-2.53 (m, 4H). MS (MALDI): calculated: m/z 588.46 (M+H$^+$); found: 587.10 (M+H$^+$).

Example 9.2: Rifamycin SV—CHNNH₂

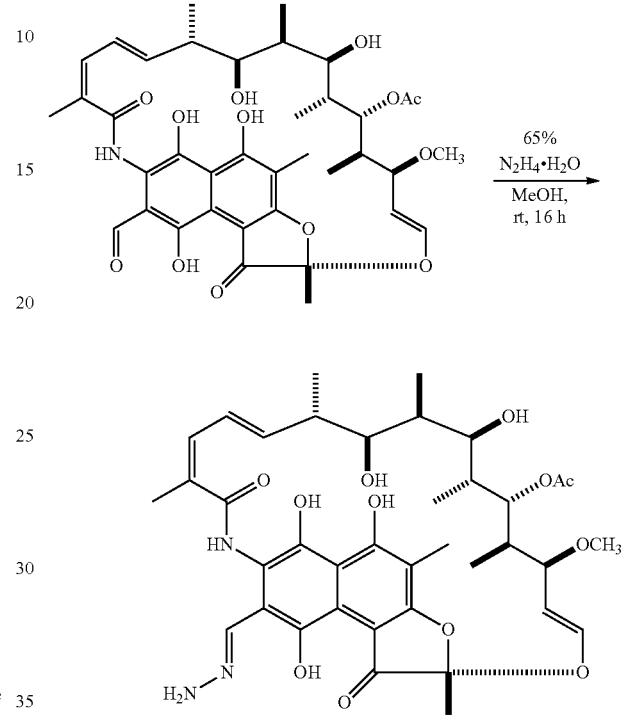

To 3-formylrifamycin SV (50 mg; 0.069 mmol; AvaChem Scientific), was added 1 mL methanol and 0.3 mL 65% hydrazine monohydrate (4.6 μL; 0.062 mmol; Sigma-Aldrich) in methanol, and the reaction mixture was stirred 16 h at room temperature. The reaction mixture was evaporated to dryness, and the crude product was used in the next step without further purification. Crude yield: 42 mg; 82%

Example 9.3: Rifamycin SV—(CHNNHCH₂CO)—IX-370a Conjugate (IX-491a)

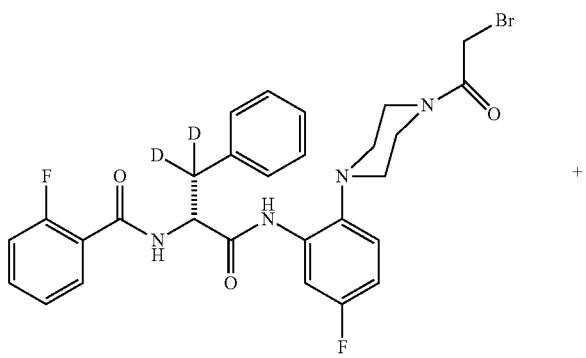

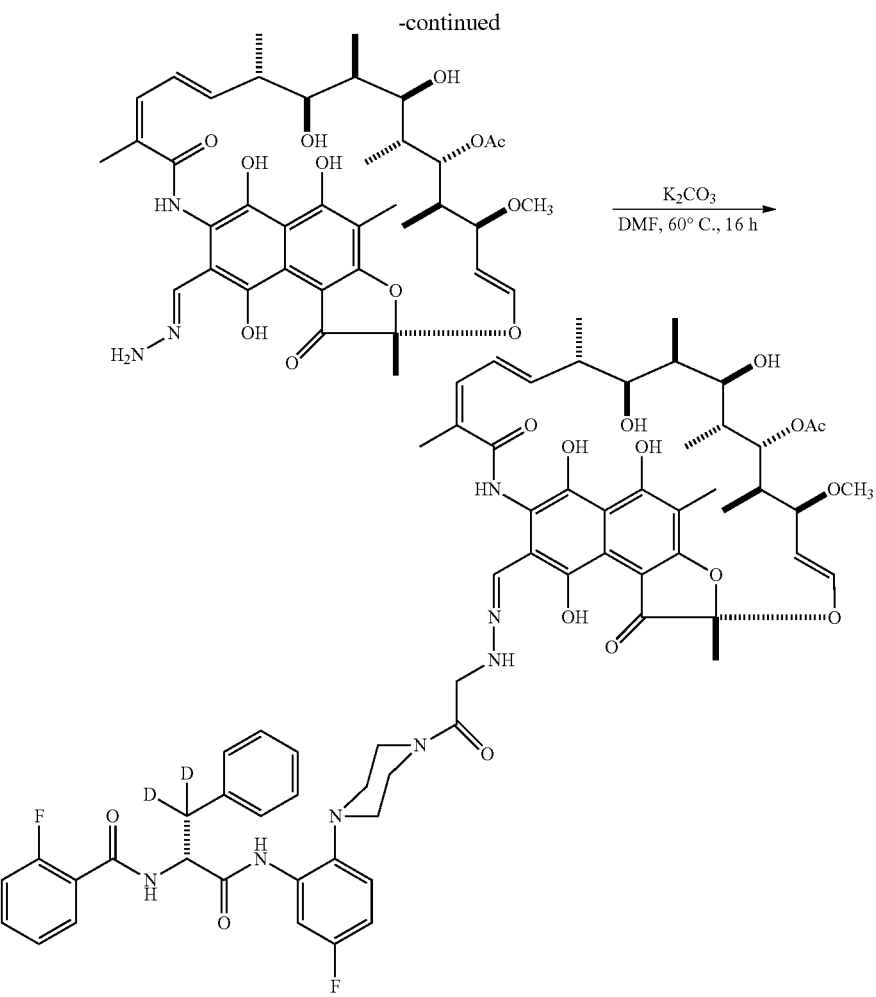

To a solution of rifamycin SV—CHNNH$_2$ (42 mg; 0.057 mmol; Example 9.2) in 1 mL DMF at room temperature, was added potassium carbonate (9.4 mg; 0.068 mmol) and (R)—N-(1-((2-(4-(2-bromoacetyl)piperazin-1-yl)-5-fluorophenyl)amino)-1-oxo-3-phenylpropan-2-yl-3,3-d$_2$)-2-fluorobenzamide (33 mg; 0.056 mmol; Example 9.1), and the reaction mixture was stirred 16 h at 60° C. under argon. The reaction mixture was evaporated to dryness, and the product was purified by silica chromatography (ethyl acetate/hexanes gradient). Yield: 9.5 mg; 13%. MS (MALDI): calculated: m/z 1247.37 (M+H$^+$); found: 1268.49 (M+Na$^+$).

Example 10: Synthesis of Rifamycin SV—(CH$_2$NH)—IX-370a Conjugate (IX-487a)

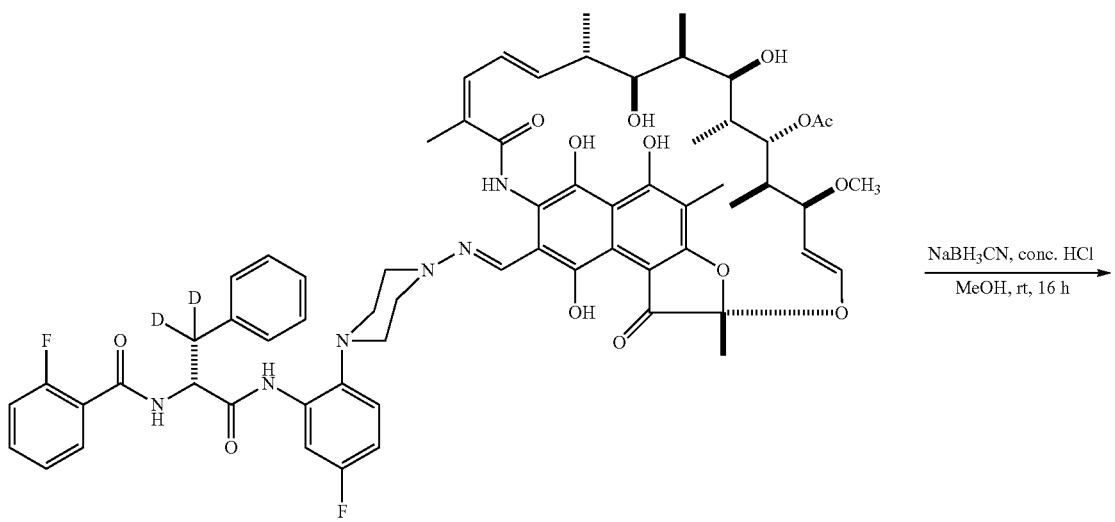

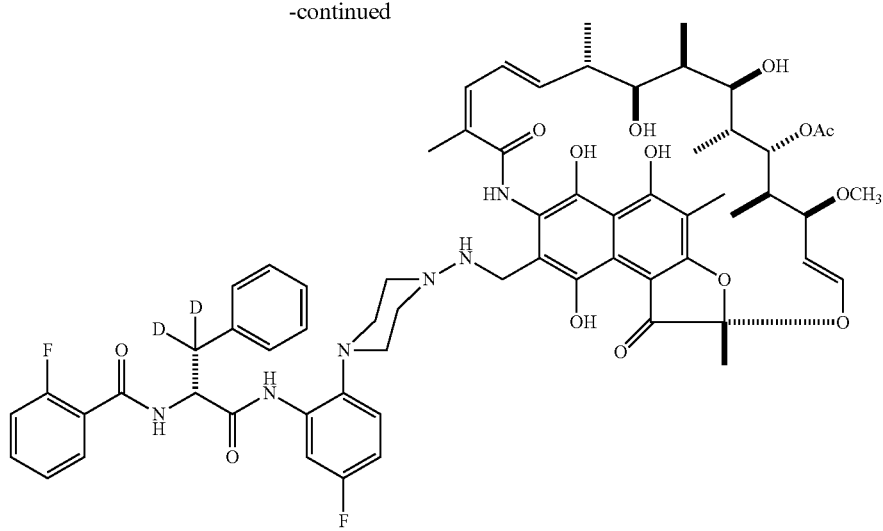

To a solution of IX-404a (50 mg; 0.042 mmol; Example 5) in 3.5 mL MeOH at room temperature, was added conc. HCl (5 μL; Fisher Scientific) and sodium cyanoborohydride (4 mg; 0.064 mmol; Sigma-Aldrich), and the reaction mixture was stirred 16 h at room temperature. The reaction mixture was evaporated to dryness, and the crude product was analyzed via LC-MS. MS (LC-MS): calculated: m/z 1192.33 (M+H$^+$); found: 1191.50 (M+H$^+$).

Example 11: Assay of RNAP-Inhibitory Activity

Fluorescence-detected RNA polymerase assays were performed by a modification of the procedure of Kuhlman et al., 2004 [Kuhlman, P., Duff, H. and Galant, A. (2004) A fluorescence-based assay for multisubunit DNA-dependent RNA polymerases. *Anal. Biochem.* 324, 183-190]. Reaction mixtures contained (20 μL): 0-100 nM test compound, 75 nM *Mycobacterium tuberculosis* RNA polymerase core enzyme or *Mycobacterium tuberculosis* RNA polymerase core enzyme derivative [prepared as in Lin, W., Mandal, S., Degen, D., Liu, Y., Ebright, Y. W., Li, S., Feng, Y., Zhang, Y., Mandal, S., Jiang, Y., Liu, S., Gigliotti, M., Talaue, M., Connell, N., Das, K., Arnold, E., and Ebright, R. H. (2017) *Mol. Cell* 66, 169-179], 300 nM *Mycobacterium tuberculosis* σ$^A$, 20 nM 384 bp DNA fragment containing the bacteriophage T4 N25 promoter, 100 μM ATP, 100 μM GTP, 100 μM UTP, 100 μM CTP, 40 mM Tris-HCl, pH 8.0, 80 mM NaCl, 5 mM MgCl$_2$, 2.5 mM DTT, and 12.7% glycerol. Reaction components other than DNA and NTPs were pre-incubated for 10 min at 37° C. Reactions were carried out by addition of DNA and incubation for 5 min at 37° C., followed by addition of NTPs and incubation for 60 min at 37° C. DNA was removed by addition of 1 μL 5 mM CaCl$_2$ and 2 U DNaseI (Ambion, Inc.), followed by incubation for 90 min at 37° C. RNA was quantified by addition of 100 μl RiboGreen RNA Quantitation Reagent (Invitrogen, Inc.; 1:500 dilution in Tris-HCl, pH 8.0, 1 mM EDTA), followed by incubation for 10 min at 25° C., followed by measurement of fluorescence intensity [excitation wavelength=485 nm and emission wavelength=535 nm; QuantaMaster QM1 spectrofluorimeter (PTI, Inc.)]. IC$_{50}$ is defined as the concentration of inhibitor resulting in 50% inhibition of RNA polymerase activity.

Data for compounds of this invention and comparator compounds rifampin and IX-370a are presented in Table 1.

Example 12: Assay of Antibacterial Activity

MICs for *Mycobacterium tuberculosis* H37Rv; rifampin-resistant *Mycobacterium tuberculosis* isolates 20626 (rpoB-H'526'd), 4457 (rpoB-H'526'Y), and 14571 (rpoB-S'531'L; and *Mycobacterium avium* ATCC 25291) were quantified using microplate Alamar Blue assays as described [Collins, L. and Franzblau, S. (1997) *Antimicrob. Agents Chemother.* 41, 1004-1009].

Data for compounds of this invention and comparator compound rifampin are presented in Tables 2-3.

Example 13: Crystal Structure of IX-404a Bound to a *Mycobacterium tuberculosis* Transcription Initiation Complex A crystal structure of IX-404a, a compound of this invention, bound to a *Mycobacterium tuberculosis* transcription initiation complex has been determined at a resolution of 4.3 Å and an R$_{free}$ of 0.27 (FIG. 5). The crystal structure was determined by soaking IX-404a into a pre-formed crystal of a *Mycobacterium tuberculosis* transcription initiation complex, collecting X-ray diffraction data at a synchroton beamline, solving the structure by molecular replacement using atomic coordinates for the structure of a *Mycobacterium tuberculosis* transcription initiation complex in the absence of IX-404a as the search model, and refining the structure (methods for crystal growth, crystal soaking, data collection, structure solution, and structure refinement as for determination of a structure of rifampin and D-AAP1 bound to *Mycobacterium tuberculosis* transcription initiation complex in [Lin, W., Mandal, S., Degen, D., Liu, Y., Ebright, Y., Li, S., Feng, Y., Zhang, Y., Mandal, S., Jiang, Y., Liu, S., Gigliotti, M., Talaue, M., Connell, N., Das, K., Arnold, E., and Ebright, R. (2017) Structural basis of *Mycobacterium tuberculosis* transcription and transcription inhibition. Molecular Cell 166, 169-179]).

The crystal structure shows that two molecules of a compound of this invention can bind simultaneously to RNA polymerase; a first molecule of a compound of this invention can bind, through its Rif moiety, to the Rif target of RNA polymerase; and a second molecule of a compound of this invention can bind, through its AAP moiety, to the bridge-helix N-terminus target of RNA polymerase (FIG. 5).

The crystal structure explains the ability of a compound of this invention to overcome rifamycin-resistance caused by a mutation altering the Rif target of RNA polymerase (Tables 1-3) and the ability of a compound of this invention to overcome AAP-resistance caused by a mutation altering the bridge-helix N-terminus target of RNAP polymerase. (Table 1). Namely, a mutation altering only one of the Rif target of RNA polymerase and he the bridge-helix N-terminus target of RNA polymerase will prevent binding of, and inhibition by, only one of two molecules of a compound of this invention; in each case, binding of, and inhibition by, the other molecule of a compound of this invention will continue.

Data for compounds of this invention and comparator compounds rifampin and IX-370a are presented in the following Tables:

TABLE 1

Inhibition of bacterial RNAP.

| compund | RNAP-inhibitory activity M. tuberculosis RNAP IC50 (µM) | RNAP-inhibitory activity rifampin-resistant M. tuberculosis RNAP (rpoB-S'531'L) IC50 (µM) | RNAP-inhibitory activity AAP-resistant M. tuberculosis RNAP (rpoB-R'637'C) IC50 (µM) |
|---|---|---|---|
| rifampin | 0.04 | >400 | 0.04 |
| IX-370a | 0.9 | 0.3 | 4 |
| IX-398 | 0.04 | 20 | 0.02 |
| IX-404a | 0.01 | 2 | 0.01 |
| IX-408a | 0.04 | 2 | 0.03 |

The data in Table 1 show that certain compounds of this invention potently inhibit a bacterial RNA polymerase.

The data in Table 1 further show that certain compounds of this invention inhibit a rifampin-resistant bacterial RNA polymerase >20 to >200 times more potently than rifampin.

The data in Table 1 further show that certain compounds of this invention inhibit an AAP-resistant bacterial RNA polymerase 20 to 40 times more potently than IX-370a.

TABLE 2

Inhibition of bacterial growth, Mycobacterium tuberculosis.

| compund | antibacterial activity M. tuberculosis H37Rv MIC (µg/ml) | antibacterial activity rifampin-resistant M. tuberculosis 20626 (rpoB-H'526'D) MIC (µg/ml) | antibacterial activity rifampin-resistant M. tuberculosis 4457 (rpoB-H'526'Y) MIC (µg/ml) | antibacterial activity rifampin-resistant M. tuberculosis 10545 (rpoB-S'531'L) MIC (µg/ml) |
|---|---|---|---|---|
| rifampin | 0.049 | >50 | >50 | >50 |
| IX-398 | 0.39 | 12.5 | 3.13 | 6.25 |
| IX-403 | 3.13 | 25 | 12.5 | 12.5 |
| IX-404a | 0.049 | 25 | 3.13 | 6.25 |
| IX-408a | 0.20 | 12.5 | 3.13 | 3.13 |
| IX-476a | 0.20 | ND | 3.13 | 6.25 |

The data in Table 2 show that certain compounds of this invention potently inhibit growth of Mycobacterium tuberculosis.

The data in Table 2 further show that certain compounds of this invention inhibit rifampin-resistant isolates of Mycobacterium tuberculosis >2 to >64 times more potently than rifampin.

TABLE 3

Inhibition of bacterial growth, non-tubercular Mycobacteria (NTM)

| compund | antibacterial activity M. avium ATCC 25291 |
|---|---|
| rifampin | 0.024 |
| IX-398 | 0.098 |
| IX-403 | 3.13 |
| IX-404a | 0.048 |
| IX-408a | 0.78 |

The data in Table 3 show that certain compounds of this invention potently inhibit growth of the non-tubercular Mycobacterium (NTM) Mycobacterium avium.

What is claimed is:

1. A compound of formula (I):

X-α-Y         (I)

or a salt thereof, wherein:

X is selected from rifamycin, streptovaricin, tolypomycin, or sorangicin;

Y is selected from a CBR hydrazide, a CBR pyrazole, or an Nα-aroyl-N-aryl-phenylalaninamide; and α is a covalent bond or a linker.

2. The compound of claim 1, wherein X is rifamycin.

3. The compound of claim 1, wherein X is rifamycin S or rifamycin SV.

4. The compound of claim 1, wherein X is connected to α through one of C3 of the rifamycin fused ring system, a moiety pendant from C3 of the rifamycin fused ring system, C4 of the rifamycin fused ring system, a moiety pendant from C4 of the rifamycin fused ring system, C11 of the rifamycin fused ring system, and a moiety pendant from C11 of the rifamycin fused ring system.

5. The compound of claim 1, wherein Y is selected from a CBR pyrazole, an Nα-aroyl-N-aryl-phenylalaninamide.

6. The compound of claim 1, wherein Y is a compound according to general structural formula (I), or a tautomer or salt thereof:

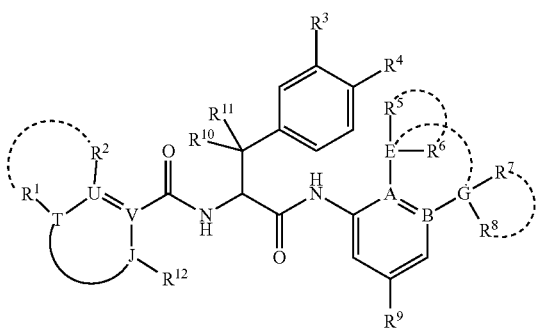

wherein:

T and U each is one of carbon and nitrogen;
V is carbon;
A and B each is one of carbon and nitrogen;
E is one of carbon (CH), nitrogen, oxygen, and sulfur;
G is absent or is one of hydrogen, halogen, carbon(CH), nitrogen, oxygen, and sulfur;
J is one of carbon and nitrogen, and J, together with T, U, V, and two additional atoms, forms a 6-membered cycle; or J is one of nitrogen, oxygen, sulfur, and selenium and J, together with T, U, V, and one additional atom, forms a 5-membered cycle;
$R^1$ and $R^2$ each independently is absent, hydrogen, hydroxy, or halogen, or is alkyl, alkoxy-substituted alkyl, amino-substituted alkyl, aryl-substituted alkyl, or alkoxy, each optionally substituted by halogen; or $R^1$ and $R^2$, together with T and U, form a cycle containing 4 to 9 atoms selected from carbon, nitrogen, oxygen, and sulfur;
$R^3$ and $R^4$ each independently is hydrogen, halogen, hydroxy, amine, amide, ester, phosphate, or O-methylphosphate; and
$R^5$, $R^6$, $R^7$, and $R^8$ each independently is absent, hydrogen, or halogen, or is alkyl, alkoxy-substituted alkyl, hydroxy-substituted alkyl, amino-substituted alkyl, aryl-substituted alkyl, or alkoxy, each optionally substituted by halogen; or $R^5$ and $R^6$, together with E, form a cycle containing 3 to 9 atoms selected from carbon, nitrogen, oxygen, and sulfur, said cycle optionally substituted with halogen, amino, alkyl, hydroxy-substituted alkyl, alkoxy-substituted alkyl, amino-substituted alkyl, aryl-substituted alkyl, alkoxy, acyl, or carbamidyl, each optionally substituted by halogen; or $R^7$ and $R^8$, together with G, form a cycle containing 3 to 9 atoms selected from carbon, nitrogen, oxygen, and sulfur, said cycle optionally substituted with halogen, amino, alkyl, hydroxy-substituted alkyl, alkoxy-substituted alkyl, amino-substituted alkyl, aryl-substituted alkyl, alkoxy, acyl, or carbamidyl, each optionally substituted by halogen;

or $R^6$ and $R^7$ are absent and E and G, together with A and B, form a cycle containing 4 to 9 atoms selected from carbon, nitrogen, oxygen, and sulfur, said cycle optionally substituted with halogen, amino, alkyl, hydroxy-substituted alkyl, alkoxy-substituted alkyl, amino-substituted alkyl, aryl-substituted alkyl, alkoxy, acyl, or carbamidyl, each optionally substituted by halogen;

$R^9$, is hydrogen or halogen;

$R^{10}$ and $R^{11}$ each independently is hydrogen, halogen, alkyl or alkoxy, said alkyl or alkoxy optionally substituted by halogen; or one of $R^{10}$ and $R^{11}$ is deuterium and the other is halogen, alkyl or alkoxy, said alkyl or alkoxy optionally substituted by halogen; or each of $R^{10}$ and $R^{11}$ is deuterium; and $R^{12}$ is absent, hydrogen, or halogen.

7. The compound of claim 6, wherein the compound of formula (I) is a compound of formula (Xa), or a tautomer or salt thereof:

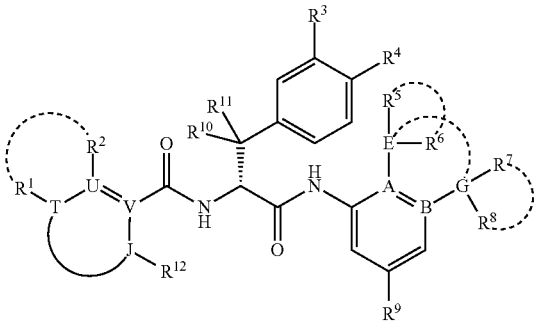

8. The compound of claim 6, wherein Y is connected to a through one of W, Y, $R^5$, and $R^6$.

9. The compound of claim 1, wherein α comprises a chain of 0 to about 12 consecutively bonded atoms.

10. The compound of claim 1, wherein α comprises a chain of 0 to about 8 consecutively bonded atoms.

11. A compound, or a salt thereof, selected from:

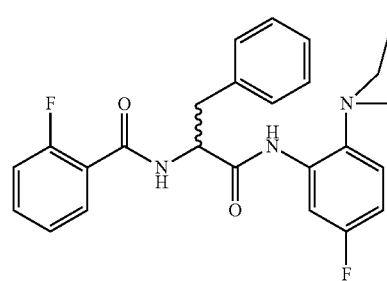

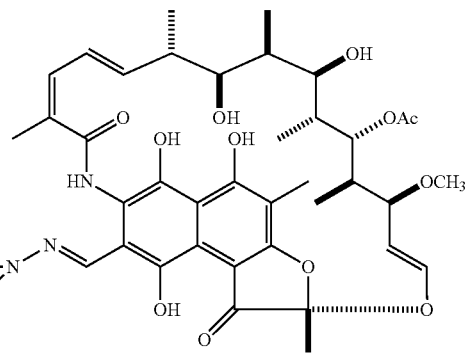

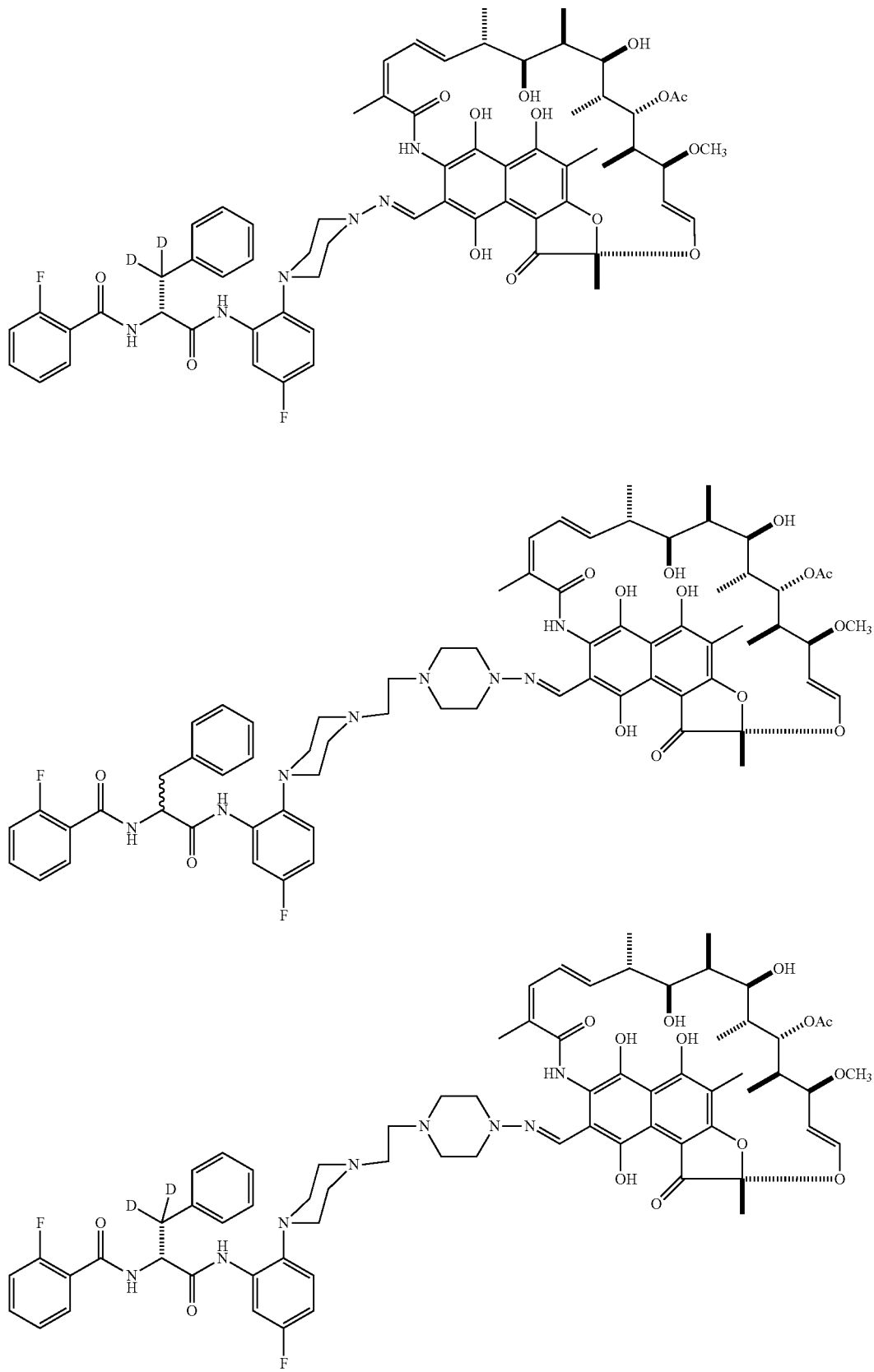

-continued
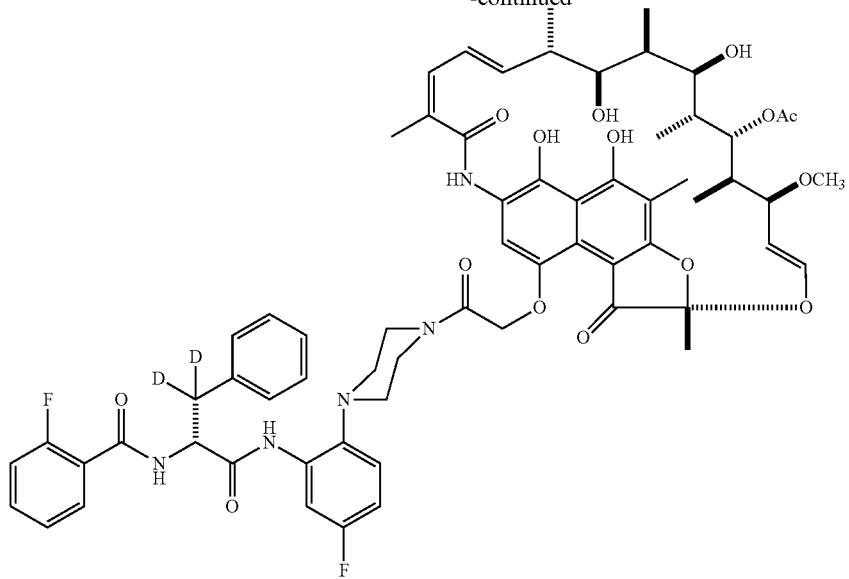
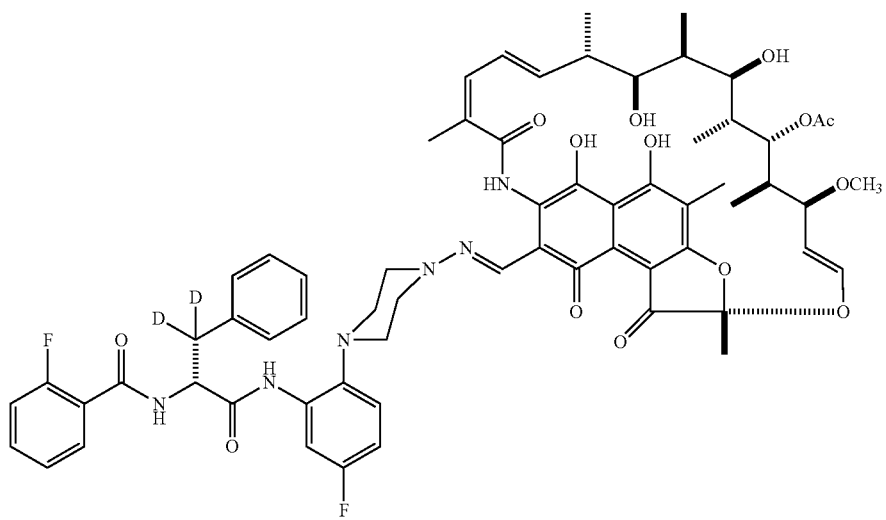
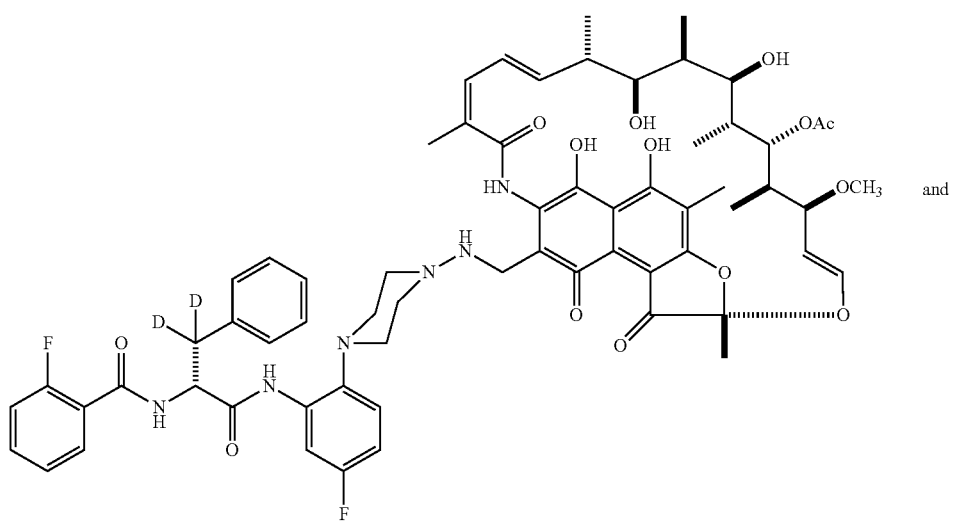
and

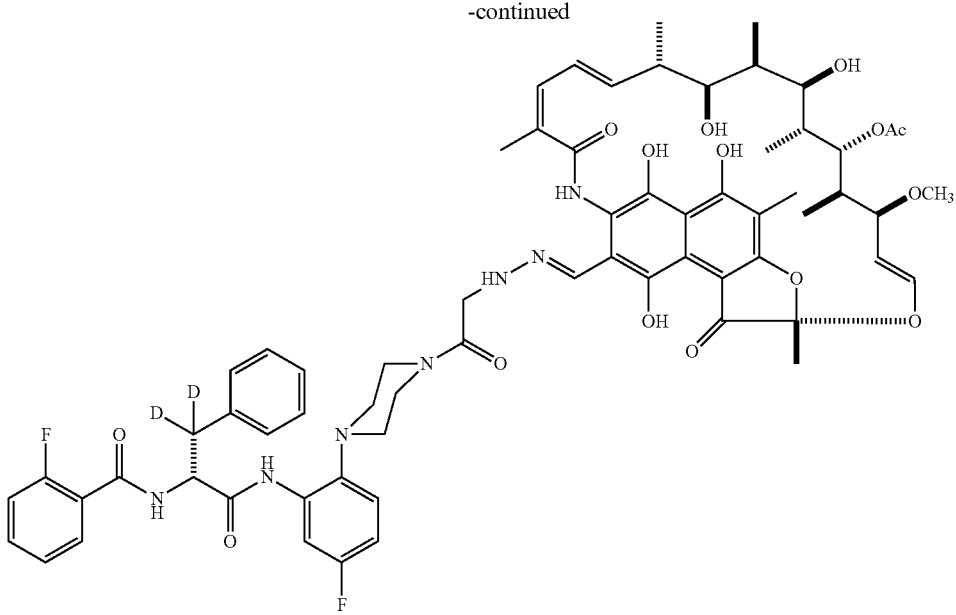

or a tautomer or salt thereof.

12. The compound of claim 1, wherein the compound inhibits a bacterial RNA polymerase with a potency higher than the potency of X and the potency of Y.

13. The compound of claim 1, wherein the compound inhibits a bacterial RNA polymerase resistant to at least one of X and Y.

14. The compound of claim 1, wherein the compound is prepared from precursors X-α' and 'α-Y, wherein α' and 'α are moieties that can react to form α.

15. A method for inhibiting a bacterial RNA polymerase comprising contacting the bacterial RNA polymerase with a compound as described in claim 1 or a salt thereof.

16. A method for inhibiting the growth of bacteria comprising contacting the bacteria with a compound as described in claim 1 or a salt thereof.

17. A method for treating a bacterial infection in a mammal comprising administering to the mammal an effective amount of a compound as described in claim 1 or a pharmaceutically acceptable salt thereof.

18. The compound,

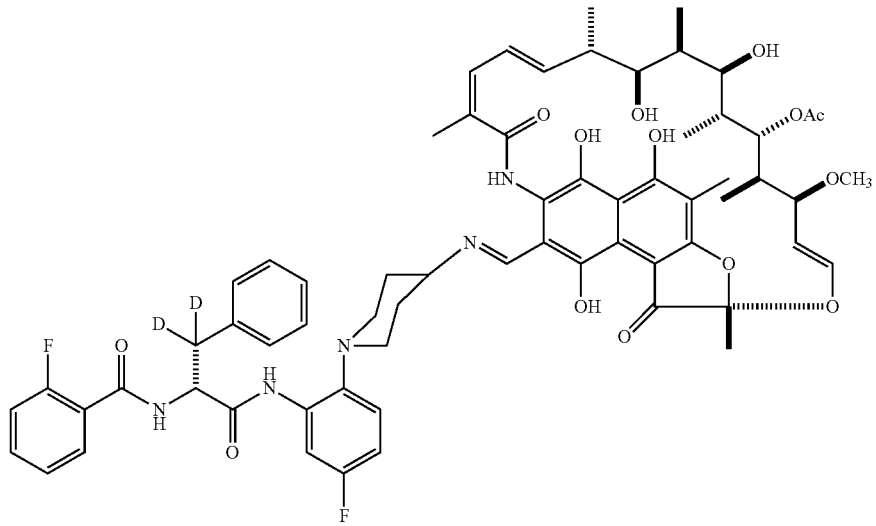

or a salt thereof.

* * * * *

UNITED STATES PATENT AND TRADEMARK OFFICE
CERTIFICATE OF CORRECTION

| | |
|---|---|
| PATENT NO. | : 11,447,502 B2 |
| APPLICATION NO. | : 17/058589 |
| DATED | : September 20, 2022 |
| INVENTOR(S) | : Ebright et al. |

It is certified that error appears in the above-identified patent and that said Letters Patent is hereby corrected as shown below:

In the Specification

Column 1, Lines 16-20, please delete "The invention described herein was made with United States Government support under Grant Number U19-AI109713 awarded by the National Institutes of Health. The United States Government has certain rights in the invention." and insert -- This invention was made with government support under grant number AI109713 awarded by the National Institutes of Health. The government has certain rights in the invention. --.

Signed and Sealed this
Thirteenth Day of June, 2023

Katherine Kelly Vidal
*Director of the United States Patent and Trademark Office*